US007438911B2

(12) United States Patent
Shitara et al.

(10) Patent No.: US 7,438,911 B2
(45) Date of Patent: Oct. 21, 2008

(54) ANTIBODY AGAINST HUMAN INSULIN-LIKE GROWTH FACTOR

(75) Inventors: Kenya Shitara, Fujisawa (JP); Kazuyasu Nakamura, Machida (JP); Akiko Furuya, Machida (JP); Rinpei Niwa, Machida (JP); Yuji Ohki, Machida (JP); Nobuo Hanai, Princeton, NJ (US)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 424 days.

(21) Appl. No.: 10/513,148

(22) PCT Filed: Apr. 30, 2003

(86) PCT No.: PCT/JP03/05505

§ 371 (c)(1),
(2), (4) Date: Oct. 29, 2004

(87) PCT Pub. No.: WO03/093317

PCT Pub. Date: Nov. 13, 2003

(65) Prior Publication Data

US 2006/0165695 A1    Jul. 27, 2006

(30) Foreign Application Priority Data

Apr. 30, 2002   (JP)   ............... 2002-129046

(51) Int. Cl.
| | |
|---|---|
| *A61K 39/395* | (2006.01) |
| *G01N 33/53* | (2006.01) |
| *C12N 5/06* | (2006.01) |
| *C12N 15/00* | (2006.01) |
| *C12P 21/08* | (2006.01) |
| *C07K 16/22* | (2006.01) |

(52) U.S. Cl. ............... 424/145.1; 530/388.25; 435/7.1; 435/69.1; 435/326; 435/320.1

(58) Field of Classification Search ............... None
See application file for complete search history.

(56) References Cited

U.S. PATENT DOCUMENTS

2006/0263362 A1* 11/2006 Ochiai et al. ............. 424/145.1

FOREIGN PATENT DOCUMENTS

| EP | 0 292 656 | 11/1988 |
|---|---|---|
| EP | 0 492 552 | 7/1992 |
| WO | WO 85/00831 | 2/1985 |

OTHER PUBLICATIONS

Laubli et al., FEBS Letters. Nov. 1982 149(1):109-112.*
Laubli et al., FEBS Letters. Nov. 1982; 149(1)109-112 (previously cited in the Office Action of Mar. 29, 2007).*
Nissley et al., (C.H. Li. Ed) Hormonal Proteins & Peptides, vol. XII. New YOrk: Academic. Press. 1984. pp. 127-203.*
Van Regenmortel. J. Immunol Methods. Jul. 1, 1998;216(1-2):37-48.*
Van Wyk et al., Endocrinology. 1997;138(10):4521-4532.*
Upstate Biotechnology, catalog #05-166, accessed Feb. 2, 2008.*
Millipore catalog #05-166, accessed Feb. 2, 2008.*
Tanaka et al., Endocrinology. Feb. 1989;124(2):870-7.*
Dai, et al., "Creation of an Autocrine Model of Insulin-Like Growth Factor-I Action in . . . ", *Endocrinology*, vol. 130, No. 6 (1992), pp. 3175-3183.
Laubli, et al., "Monoclonal antibodies directed to human insulin-like growth factor I (IGF I)", *FEBS Letters*, vol. 149, No. 1 (1982), pp. 109-112.
Enjoh, et al., "Characterization of New Monoclonal Antibodies to Human Insulin-Like Growth Factor-II and . . . ", *Journal of Clinical Endocrinology and Metabolism*, vol. 77, No. 2 (1993), pp. 510-517.
Lamonerie, et al., "IGF-2 Autocrine Stimulation in Tumorigenic Clones of A Human Colon-Carcinoma Cell Line", *Int. J. Cancer*, vol. 61, No. 4 (1995), pp. 587-592.
Riechmann, et al., "Reshaping human antibodies for therapy", *Nature*, vol. 332, No. 24 (1988), pp. 323-327.
Russell, et al., "Inhibition of the mitogenic effects of plasma by a monoclonal antibody to somatomedin C", *Proc. Natl. Acad. Sci.*, vol. 81 (1984), pp. 2389-2392.
Tamura, et al., "Enzyme-linked immunosorbent assay for human insulin-like growth factor-I using monoclonal and . . . " *Journal of Endocrinology*, vol. 125 (1990), pp. 327-335.
Tanaka, et al., "Identification of a Family of Insulin-Like Growth Factor II Secreted by Cultured . . . " *Endocrinology*, vol. 124, No. 2 (1989), pp. 870-877.
Harvey, et al., "Production of Monoclonal Antibodies Recognising Different Epitopes Present on Insulin-Like Growth Factor 1", *Hybridoma*, vol. 12, No. 6 (1993), pp. 737-744.
Su, et al., "Neutralizing IGF-1 Monoclonal Antibody With Cross-Species Reactivity", *Hybridoma*, vol. 16, No. 6 (1997), pp. 513-518.
Morrell, et al., "A monoclonal antibody to human insulin-like growth factor-I: characterization, use in . . . ", Journal of Molecular Endocrinology, vol. 2 (1989), pp. 201-206.

* cited by examiner

*Primary Examiner*—Gary B. Nickol
*Assistant Examiner*—Cherie Woodward
(74) *Attorney, Agent, or Firm*—Fitzpatrick, Cella, Harper & Scinto

(57) ABSTRACT

For the effective treatment of diseases such as cancer in which hIGF participates, there have been desired to be developed antibodies which strongly bind to both factors hIGF-I and hIGF-II and inhibit their functions and fragments of these antibodies. The present invention provides antibodies which have the ability to specifically bind to human IGF-I and IGF-II to thereby inhibit the functions of human IGF-I and IGF-II and have binding activity with a binding constant of $5 \times 10^9$ $M^{-1}$ or more measured with a biosensor BIACORE. In addition, the present invention provides diagnostics, preventives and remedies for an hIGF-mediated disease and a disease showing pathological progressing due to abnormally promoted hIGF production, which use said antibodies.

13 Claims, 17 Drawing Sheets

SEQUENCE LISTING

<160> NUMBER OF SEQ ID NOS: 28

<210> SEQ ID NO 1
<211> LENGTH: 411
<212> TYPE: DNA
<213> ORGANISM: Rattus norvegics
<220> FEATURE:
<221> NAME/KEY: CDS
<222> LOCATION: (1)..(411)

<400> SEQUENCE: 1

```
atg gac atc agg ctc agc ttg gtt ttc ctt gtc ctt ttc ata aaa ggt        48
Met Asp Ile Arg Leu Ser Leu Val Phe Leu Val Leu Phe Ile Lys Gly
  1               5                  10                  15 gtc cag tgt gag gta cac ctg gtg gaa tct ggg gga ggc tta gtg cag        96
Val Gln Cys Glu Val His Leu Val Glu Ser Gly Gly Gly Leu Val Gln
             20                  25                  30 cct gga agg tcc ctg aaa ctc tcc tgt gca gcc tca gga ttc act ttc       144
Pro Gly Arg Ser Leu Lys Leu Ser Cys Ala Ala Ser Gly Phe Thr Phe
         35                  40                  45 agt aac tat tac atg acc tgg gtc cgc cag gct cca acg aag ggt ctg       192
Ser Asn Tyr Tyr Met Thr Trp Val Arg Gln Ala Pro Thr Lys Gly Leu
     50                  55                  60 gag tgg gtc gca tac att agt agt ggt ggt ggt agc act tac tat cga       240
Glu Trp Val Ala Tyr Ile Ser Ser Gly Gly Gly Ser Thr Tyr Tyr Arg
 65                  70                  75                  80 gac tcc gtg aag ggc cga ttc act atc tcc aga gat aat gca aaa agc       288
Asp Ser Val Lys Gly Arg Phe Thr Ile Ser Arg Asp Asn Ala Lys Ser
                 85                  90                  95 acc ctg tac ctg caa atg gac agt ctg agg tct gag gac acg gcc act       336
Thr Leu Tyr Leu Gln Met Asp Ser Leu Arg Ser Glu Asp Thr Ala Thr
            100                 105                 110
```

-continued

```
tat tac tgt aca aca gag gac tat ggg tat tgg ttt gct tac tgg ggc    384
Tyr Tyr Cys Thr Thr Glu Asp Tyr Gly Tyr Trp Phe Ala Tyr Trp Gly
        115                 120                 125 caa ggc act ctg gtc act gtc tct tca                                411
Gln Gly Thr Leu Val Thr Val Ser Ser
130                 135
```

<210> SEQ ID NO 2
<211> LENGTH: 137
<212> TYPE: PRT
<213> ORGANISM: Rattus norvegics

<400> SEQUENCE: 2

```
Met Asp Ile Arg Leu Ser Leu Val Phe Leu Val Leu Phe Ile Lys Gly
1               5                   10                  15

Val Gln Cys Glu Val His Leu Val Glu Ser Gly Gly Gly Leu Val Gln
            20                  25                  30

Pro Gly Arg Ser Leu Lys Leu Ser Cys Ala Ala Ser Gly Phe Thr Phe
        35                  40                  45

Ser Asn Tyr Tyr Met Thr Trp Val Arg Gln Ala Pro Thr Lys Gly Leu
    50                  55                  60

Glu Trp Val Ala Tyr Ile Ser Ser Gly Gly Gly Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Thr Thr Glu Asp Tyr Gly Tyr Trp Phe Ala Tyr Trp Gly
        115                 120                 125

Gln Gly Thr Leu Val Thr Val Ser Ser
    130                 135
```

<210> SEQ ID NO 3
<211> LENGTH: 387
<212> TYPE: DNA
<213> ORGANISM: Rattus norvegics
<220> FEATURE:
<221> NAME/KEY: CDS
<222> LOCATION: (1)..(387)

<400> SEQUENCE: 3

```
atg gat ttt cag gtg cag agt ttc agc ctc ctg cta atc agt atc aca    48
Met Asp Phe Gln Val Gln Ser Phe Ser Leu Leu Leu Ile Ser Ile Thr
1               5                   10                  15 gtc ata gtg tcc agt gga gaa att gtg ctc acc cag tct cca aca acc    96
Val Ile Val Ser Ser Gly Glu Ile Val Leu Thr Gln Ser Pro Thr Thr
            20                  25                  30 atg gct gca tct cca gga gag aag gtc acc atc acc tgc cgt gcc agc    144
Met Ala Ala Ser Pro Gly Glu Lys Val Thr Ile Thr Cys Arg Ala Ser
        35                  40                  45 tca agt gta agc tac atg cac tgg ttc cag cag aag tca ggc acc tcc    192
Ser Ser Val Ser Tyr Met His Trp Phe Gln Gln Lys Ser Gly Thr Ser
    50                  55                  60 ccc aaa ccc tgg att tat ggc aca tcc aag ctg gct tct gga gtc cca    240
Pro Lys Pro Trp Ile Tyr Gly Thr Ser Lys Leu Ala Ser Gly Val Pro
65                  70                  75                  80 gat cgc ttc agt ggc agt ggg tct ggg acc tct tat tct ctc aca atc    288
Asp Arg Phe Ser Gly Ser Gly Ser Gly Thr Ser Tyr Ser Leu Thr Ile
                85                  90                  95
```

```
agc tcc atg gag gct gaa gat gct gct act tat tac tgt ctg cag agg    336
Ser Ser Met Glu Ala Glu Asp Ala Ala Thr Tyr Tyr Cys Leu Gln Arg
        100                 105                 110 agt agt tac cca ccc acg ttt gga gct ggg acc aag ctg gaa ctg aaa    384
Ser Ser Tyr Pro Pro Thr Phe Gly Ala Gly Thr Lys Leu Glu Leu Lys
            115                 120                 125 cgg                                                                387
Arg

<210> SEQ ID NO 4
<211> LENGTH: 129
<212> TYPE: PRT
<213> ORGANISM: Rattus norvegics

<400> SEQUENCE: 4

Met Asp Phe Gln Val Gln Ser Phe Ser Leu Leu Leu Ile Ser Ile Thr
 1               5                  10                  15

Val Ile Val Ser Ser Gly Glu Ile Val Leu Thr Gln Ser Pro Thr Thr
                20                  25                  30

Met Ala Ala Ser Pro Gly Glu Lys Val Thr Ile Thr Cys Arg Ala Ser
            35                  40                  45

Ser Ser Val Ser Tyr Met His Trp Phe Gln Gln Lys Ser Gly Thr Ser
        50                  55                  60

Pro Lys Pro Trp Ile Tyr Gly Thr Ser Lys Leu Ala Ser Gly Val Pro
65                  70                  75                  80

Asp Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Leu Gln Arg
            100                 105                 110

Ser Ser Tyr Pro Pro Thr Phe Gly Ala Gly Thr Lys Leu Glu Leu Lys
        115                 120                 125

Arg

<210> SEQ ID NO 5
<211> LENGTH: 5
<212> TYPE: PRT
<213> ORGANISM: Rattus norvegics

<400> SEQUENCE: 5

Asn Tyr Tyr Met Thr
 1               5

<210> SEQ ID NO 6
<211> LENGTH: 17
<212> TYPE: PRT
<213> ORGANISM: Rattus norvegics

<400> SEQUENCE: 6

Tyr Ile Ser Ser Gly Gly Gly Ser Thr Tyr Tyr Arg Asp Ser Val Lys
 1               5                  10                  15

Gly

<210> SEQ ID NO 7
<211> LENGTH: 9
<212> TYPE: PRT
<213> ORGANISM: Rattus norvegics

<400> SEQUENCE: 7

Glu Asp Tyr Gly Tyr Trp Phe Ala Tyr
```

<210> SEQ ID NO 8
<211> LENGTH: 10
<212> TYPE: PRT
<213> ORGANISM: Rattus norvegics

<400> SEQUENCE: 8

Arg Ala Ser Ser Ser Val Ser Tyr Met His
1               5                   10

<210> SEQ ID NO 9
<211> LENGTH: 7
<212> TYPE: PRT
<213> ORGANISM: Rattus norvegics

<400> SEQUENCE: 9

Gly Thr Ser Lys Leu Ala Ser
1               5

<210> SEQ ID NO 10
<211> LENGTH: 9
<212> TYPE: PRT
<213> ORGANISM: Rattus norvegics

<400> SEQUENCE: 10

Leu Gln Arg Ser Ser Tyr Pro Pro Thr
 1               5

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 11
taaagaattc gcggccgctc tccc                                          24

<210> SEQ ID NO 12
<211> LENGTH: 49
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 12
taaagtcgac gggcccttgg tggaggctga agagacagtg accagagtg               49

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 13
taaagaattc tccaaacttc aagtacacaa tgg                                33

<210> SEQ ID NO 14
<211> LENGTH: 35
<212> TYPE: DNA
<213> ORGANISM: Artificial Sequence

```
<220> FEATURE:
<223> OTHER INFORMATION: Description of Artificial Sequence: synthetic
      DNA

<400> SEQUENCE: 14
taaagtcgac cgtacgtttc agttccagct tggtc                                35

<210> SEQ ID NO 15
<211> LENGTH: 118
<212> TYPE: PRT
<213> ORGANISM: Artificial Sequence
<220> FEATURE:
<223> OTHER INFORMATION: Description of artificial sequence: synthetic
      protein

<400> SEQUENCE: 15
```

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Asn Tyr
             20                  25                  30

Tyr Met Thr Trp Val Arg Gln Ala Pro Gly Lys Gly Leu Glu Trp Val
         35                  40                  45

Ala Tyr Ile Ser Ser Gly Gly Gly Ser Thr Tyr Tyr Arg Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Asp Tyr Gly Tyr Trp Phe Ala Tyr Trp Gly Gln Gly Thr
            100                 105                 110

Leu Val Thr Val Ser Ser
            115

```
<210> SEQ ID NO 16
<211> LENGTH: 107
<212> TYPE: PRT
<213> ORGANISM: Artificial Sequence
<220> FEATURE:
<223> OTHER INFORMATION: Description of artificial sequence: synthetic
      protein

<400> SEQUENCE: 16
```

Asp Ile Val Met Thr Gln Ser Pro Asp Ser Leu Ala Val Ser Leu Gly
  1               5                  10                  15

Glu Arg Ala Thr Ile Asn Cys Arg Ala Ser Ser Ser Val Ser Tyr Met
             20                  25                  30

His Trp Tyr Gln Gln Lys Pro Gly Gln Pro Lys Leu Leu Ile Tyr
         35                  40                  45

Gly Thr Ser Lys Leu Ala Ser Gly Val Pro Asp Arg Phe Ser Gly Ser
     50                  55                  60

Gly Ser Gly Thr Asp Phe Thr Leu Thr Ile Ser Ser Leu Gln Ala Glu
 65                  70                  75                  80

Asp Val Ala Val Tyr Tyr Cys Leu Gln Arg Ser Ser Tyr Pro Pro Thr
                 85                  90                  95

Phe Gly Gln Gly Thr Lys Val Glu Ile Lys Arg
            100                 105

```
<210> SEQ ID NO 17
<211> LENGTH: 18
<212> TYPE: PRT
```

-continued

<213> ORGANISM: Homo sapiens

<400> SEQUENCE: 17

Gly Pro Glu Thr Leu Ser Gly Ala Glu Leu Val Asp Ala Leu Gln Phe
1               5                   10                  15

Val Cys

<210> SEQ ID NO 18
<211> LENGTH: 18
<212> TYPE: PRT
<213> ORGANISM: Homo sapiens

<400> SEQUENCE: 18

Cys Leu Gln Phe Val Ala Gly Asp Arg Gly Phe Tyr Phe Asn Lys Pro
1               5                   10                  15

Thr Gly

<210> SEQ ID NO 19
<211> LENGTH: 13
<212> TYPE: PRT
<213> ORGANISM: Homo sapiens

<400> SEQUENCE: 19

Cys Tyr Phe Asn Lys Pro Thr Gly Tyr Gly Ser Ser Ser
1               5                   10

<210> SEQ ID NO 20
<211> LENGTH: 14
<212> TYPE: PRT
<213> ORGANISM: Homo sapiens

<400> SEQUENCE: 20

Cys Thr Gly Tyr Gly Ser Ser Ser Arg Arg Ala Pro Gln Thr
1               5                   10

<210> SEQ ID NO 21
<211> LENGTH: 12
<212> TYPE: PRT
<213> ORGANISM: Homo sapiens

<400> SEQUENCE: 21

Arg Arg Ala Pro Gln Thr Gly Ile Val Asp Glu Cys
1               5                   10

<210> SEQ ID NO 22
<211> LENGTH: 17
<212> TYPE: PRT
<213> ORGANISM: Homo sapiens

<400> SEQUENCE: 22

Cys Thr Gly Ile Val Asp Glu Ala Ala Phe Arg Ser Ala Asp Leu Arg
1               5                   10                  15

Arg

<210> SEQ ID NO 23
<211> LENGTH: 19
<212> TYPE: PRT
<213> ORGANISM: Homo sapiens

<400> SEQUENCE: 23

Cys Asp Leu Arg Arg Leu Glu Met Tyr Ala Ala Pro Leu Lys Pro Ala
1               5                   10                  15

```
<210> SEQ ID NO 24
<211> LENGTH: 9
<212> TYPE: PRT
<213> ORGANISM: Homo sapiens

<400> SEQUENCE: 24

Asp Leu Arg Arg Leu Glu Met Tyr Cys
1               5

<210> SEQ ID NO 25
<211> LENGTH: 10
<212> TYPE: PRT
<213> ORGANISM: Homo sapiens

<400> SEQUENCE: 25

Cys Ala Pro Leu Lys Pro Ala Lys Ser Ala
1               5                   10

<210> SEQ ID NO 26
<211> LENGTH: 17
<212> TYPE: PRT
<213> ORGANISM: Homo sapiens

<400> SEQUENCE: 26

Cys Thr Gly Ile Val Asp Glu Cys Cys Phe Arg Ser Cys Asp Leu Arg
1               5                   10                  15

Arg

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 27
gatgaattca gaagcaatgg gaaaaatcag cagtc                          35

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 28
cattgtcgac gcatgtcact cttcactcct ca                             32
```

ANTIBODY AGAINST HUMAN INSULIN-LIKE GROWTH FACTOR

TECHNICAL FIELD

The present invention relates to an antibody to insulin-like growth factor (hereinafter referred to as IGF) and an antibody fragment derived from the antibody. The present invention further relates to a DNA coding for said antibody and antibody fragment. The present invention relates to recombinant vector comprising said DNA and transformant obtained by introducing said recombinant vector into a host cell. The present invention further relates to methods for producing said antibody and antibody fragment using said transformant, and diagnostic, preventive and therapeutic uses of said antibody and antibody fragment.

BACKGROUND ART

IGF is a factor which takes a very important role in controlling proliferation, differentiation and cell death (apoptosis) of epithelial cells of the breast, prostate, lung, colon and the like organs, and its action is carried out via an IGF receptor (hereinafter referred to as IGF-IR) existing on the cell surface (*Endocrine Reviews*, 16, 3-34, 1995). Also, it is known that a protein called IGF-binding protein (hereinafter referred to as IGFBP) is existing and regulating the activity of IGF promotively or inhibitively (*Endocrine Reviews*, 16, 3-34, 1995).

As the IGF, two types of IGF-I and IGF-II exist, and each of them comprises a single chain polypeptide and has about 40% homology with an insulin precursor proinsulin at the amino acid level (*Advances in Cancer Research*, 68, 183-223, 1996). As the IGF-R three types of insulin receptor exist, IGF-I receptor (hereinafter referred to as IGF-IR) and IGF-II receptor (hereinafter referred to as IGF-IIR). Each of the insulin receptor and IGF-IR belongs to the tyrosine kinase type receptor family and exists on the cell membrane as an $\alpha_2\beta_2$ hetero tetramer, after forming S—S bond of a 135 kDa $\alpha$ subunit and 95 kDa of $\beta$ subunit formed from a single chain precursor as a result of its digestion with a protease (*Endocrine Reviews*, 16, 143-163, 1995, *Breast Cancer Research & Treatment*, 47, 235-253, 1998). The insulin receptor and IGF-IR have about 60% homology, and insulin and IGF-IR, and IGF and insulin receptor, binds to each other though weak and act (*Journal of Biological Chemistry*, 263, 11486-11492, 1988, *Journal of Biological Chemistry*, 268, 7393-7400, 1993). The exististance of a hybrid receptor comprising the $\alpha\beta$ subunit of insulin receptor and the $\alpha\beta$ subunit of IGF-IR has been proved, and it is considered that the hybrid receptor has high binding affinity for IGF-I than for insulin and acts as IGF-IR, but its role in intravital is unclear (*Endocrine Reviews*, 16, 3-34, 1995, *Endocrine Reviews*, 16, 143-163, 1995). The IGF-IIR has a single chain structure, and there are three ligand-binding regions in its extracellular region. One of the ligand-binding regions is an IGF-II-binding region, and the other two are regions which bind to mannose-6-phosphate-containing proteins [renin, proliferin, thyroglobulin, endogenous transforming growth factor-$\beta$ (TGF-$\beta$) and the like] (*Endocrine Reviews*, 16, 3-34, 1995). It has been reported that the endogenous TGF-$\beta$ is activated by its binding to IGF-IIR (*Breast Cancer Research & Treatment*, 52, 175-184, 1998, *Hormone & Metabolic Research*, 31, 242-246, 1999). The IGF-IIR does not have tyrosine kinase activity and binds to only IGF-II among IGF. Since IGF-II is degraded by its binding to IGF-IIR, it is considered that IGF-IIR acts as an antagonist of IGF-II (*Breast Cancer Research & Treatment*, 52, 175-184, 1998).

Ten types of IGFBP (IGFBP-1 to IGFBP-10) have so far been known, and six types among them (IGFBP-1 to IGFBP-6) have high binding affinity for IGF (*Proceeding of the National Academy of Sciences of the United States of America*, 94, 12981-12986, 1997). IGFBP-1 to IGFBP-6 have a high homology of 40 to 60% at the amino acid level. It has been revealed that IGFBP regulates the function of IGF by undergoing various post-translation modifications such as degradation and phosphorylation and thereby exerting influences upon the transfer of IGF, inhibition of degradation and binding to receptor (*International Journal of Biochemistry & Cell Biology*, 28, 619-637, 1996, *Endocrine Reviews*, 18, 801-831, 1997). IGFBP-1, IGFBP-2, IGFBP-3 and IGFBP-5 have a case of promoting the action of IGF and a case of inhibiting the same, and the actions of IGFBP-2, IGFBP-3 and IGFBP-5 upon IGF are regulated by the degradation of IGFBP, and the action of IGFBP-1 by the phosphorylation of IGFBP-1, respectively (*Endocrine Reviews*, 16, 3-34, 1995, *International Journal of Biochemistry & Cell Biology*, 28, 619-637, 1996, *Endocrinology & Metabolism Clinics of North America*, 25,591-614, 1996). In addition, the binding affinity of IGFBP-1, IGFBP-2, IGFBP-3 and IGFBP-5 for IGF is reduced when they bind to a specific receptor existing on the cell membrane. As a result, IGFBP and IGF are dissociated to form free IGF (*Endocrine Reviews*, 16, 3-34, 1995, *International Journal of Biochemistry & Cell Biology*, 28, 619-637, 1996, *Endocrinology & Metabolism Clinics of North America*, 25, 591-614, 1996). On the other hand, IGFBP-4 and IGFBP-6 have the activity to inhibit the action of IGF (*Endocrine Reviews*, 16, 3-34, 1995, *Endocrinology & Metabolism Clinics of North America*, 25, 591-614, 1996). In intravital, 90% or more of the blood IGF binds to IGFBP-3 and an acid-labile subunit, and exists in the form of a high molecular weight complex of about 150 kDa, thereby inhibiting degradation of IGF and its drain into the extra vascular region (*Journal of Biological Chemistry*, 264, 11843-11848, 1989).

Both of the IGF-I and IGF-II show strong promoting proliferation activity to a large number of cancer cells (sarcoma, leukemia, prostate cancer, breast cancer, lung cancer, colon cancer, gastric cancer, esophageal cancer, hepatic cancer, pancreatic cancer, renal carcinoma, thyroid gland cancer, brain tumor, ovarian cancer, uterine cancer) (*British Journal of Cancer* 65, 311-320, 1992, *Anticancer Research*, 11, 1591-1595, 1991, *Annals of Internal Medicine*, 122, 54-59, 1995, *Oncology*, 54, 502-507, 1997, *Endocrinology*, 137, 1764-1774, 1996, *European Journal of Haematology*, 62, 191-198, 1999), and over-expression of IGF has been identified in a large number of cancer cells (*British Journal of Cancer*, 65,311-320, 1992). Also, it has been reported that expression amounts of IGF-II and IGF-IR are more those in higher metastatic cancer cells than those in lower metastatic cancer cells (*International Journal of Cancer*, 65, 812-820, 1996). It has been revealed that such functions of IGF occur mainly via IGF-IR (*Endocrinology* 136, 4298-4303, 1995, *Oncogene*, 28, 6071-6077, 1999), but IGF-II also acts via the insulin receptor in breast cancer cells (*Oncogene* 18, 2471-2479, 1999).

It has been reported that, in the case of transgenic mice which over-express IGF-I in prostate epithelial cells, about 50% of them develop prostate cancer after about 6 months (*Proceedings of the National Academy of Science of the United States of America*, 97, 3455-3460, 2000). Also, it has been shown that expression of IGF-I and IGF-IR is increased by the acquirement of androgen-independent proliferation ability in a human prostate cancer cell transplantation model mice (*Cancer Research*, 61, 6276-6280, 2001).

IGF is also concerned in the proliferation of cancer cells by mutually reacting with other factors. It has been reported that the activity of IGF-I is increased and expression of IGF-I and IGF-IR is induced by estrogen in breast cancer cells (*Endocrinology*, 136, 1296-1302, 1995, *Journal of Biological Chemistry*, 265, 21172-21178, 1990, *Journal of Steroid Biochemistry & Molecular Biology*, 41, 537-540, 1992, *British Journal of Cancer*, 75, 251-257, 1997). In addition, it is known that estrogen inhibits production of IGFBP, reduces expression of IGF-IIR, and increases expression of IGFBP degrading enzyme in breast cancer cells (*Biochemical & Biophysical Research Communications*, 193, 467-473, 1993, *Molecular Endocrinology*, 5, 815-822, 1991).

On the contrary, it has also been reported that IGF-I increases expression of estrogen receptor (*Endocrinology*, 127, 2679-2686, 1990, *Journal of Cellular Biochemistry*, 52, 196-205, 1993), and that IGF-I and IGF-II increase the activity of estrone sulfatase which hydrolyses estrone sulfate into estrone, in breast cancer cells (*International Journal of Molecular Medicine*, 4, 175-178, 1999).

In addition, IGF cooperatively acts with an epithelial cell growth factor (epidermal growth factor; hereinafter referred to as EGF). In cervical cancer cells, EGF increases expression of IGF-II, and IGF increases the growth activity of EGF (*Proceedings of the National Academy of Sciences of the United States of America*, 92, 11970-11974, 1995, *Cancer Research*, 2, 56, 1761-1765, 1996). It is also known that EGF increases the amount of free IGF by inhibiting expression of IGFBP-3 and thereby has a synergistic effect on cell growth activity (*Cancer Research*, 54, 3160-3166, 1994).

It is known that the function of several factors having anti-cell proliferation activity is exerted by inhibition of the IGF promoting activity to proliferation. The function of TGF-β and retinoic acid to inhibit proliferation of breast cancer cells is exerted by the inhibition of the IGF function as a result of the induction of IGFBP-3 expression (*Journal of Biological Chemistry*, 270, 13589-13592, 1995, *Cancer Research*, 56, 1545-1550, 1996, *Endocrinology*, 136, 1219-1226, 1995). In addition, vitamin D and its synthetic derivatives inhibit the function of IGF to promote proliferation of beast cancer cells and prostate cancer cells, and the action is based on the increase of IGFBP expression and inhibition of IGF-IR and IGF-II expression (*Journal of the National Cancer Institute*, 89, 652-656, 1997, *Journal of Molecular Endocrinology*, 20, 157-162, 1998, *Journal of Endocrinology*, 154, 495-504, 1997, *International Journal of Oncology*, 13, 137-143, 1998).

It has been reported that tumor suppressor gene products also have influence upon the function of IGF. For example, in sarcoma cells and the like, the wild type p53 protein induces IGFBP-3 expression and inhibits IGF-II and IGF-IR expression (*Nature*, 377, 646-649, 1995, *Cancer Research*, 56, 1367-1373, 1996, *DNA & Cell Biology*, 17, 125-131, 1998, *Proceedings of the National Academy of Sciences of the United States of America*, 93, 8318-8323, 1996, *Endocrinology*, 139, 1101-1107, 1998). In breast cancer cells, on the contrary, it is known that the p53 protein is phosphorylated by the function of IGF-I and is transported from the nucleus into cytoplasm, thereby losing the function of p53 protein (*International Journal of Cancer*, 55, 453-458, 1993). In addition to these, it has been reported that it is inhibited IGF-IR expression by a Wilms' tumor suppressor gene product WT1 (*Journal of Biological Chemistry*, 269, 12577-12582, 1994, 140, 4713-4724, 1999), and it is inhibited a mammary-derived growth inhibitor (MDGI) expression by IGF-I (*International Journal of Oncology*, 13, 577-582, 1998).

Relationship between life style such as energy intake and oncogenesis has been drawing attention from old times, and it is now partially revealed based on various animal tests that energy intake and expression of IGF, further oncogenesis, have a close relationship. In rats transplanted with prostate cancer, proliferation of the cancer is inhibited and apoptosis is induced when energy intake is restricted. This effect is correlated with the reduction of IGF-I concentration in blood (*Journal of the National Cancer Institute*, 91, 512-523, 1999). Similar result has been reported on breast cancer-transplanted mouse, and since the proliferation inhibitory function becomes un-observable by the administration of IGF-I, it is suggested that IGF-I is taking a main role in the proliferation inhibition of cancer by the restriction of energy intake (*Cancer Research*, 57, 4667-4672, 1997).

Relevancy of IGF to cancer has been examined also by clinical and epidemiological studies. It has been reported that IGF-I concentration in blood plasma and serum is high in breast cancer patients in comparison with healthy persons (*European Journal of Cancer*, 29A, 492-497, 1993, *Tumori*, 80, 212-215, 1994), and the amount of IGF-IR in breast cancer tissue is 10 times-higher than that in normal tissue (*Cancer Research*, 53, 3736-3740, 1993). Also, since the loss of heterozygosity in IGF-IIR gene was found in about 30% of breast cancer patients, it was suggested that the IGF-IIR gene has a function as a cancer suppressor gene (*Breast Cancer Research & Treatment*, 47, 269-281, 1998). It has been reported that concentrations of IGF-II, IGFBP-2 and IGFBP-3 in sera are high in colon cancer patients in comparison with those of healthy persons (*International Journal of Cancer*, 57, 491-497, 1994). In addition, it has been shown that serum concentrations of IGF-II and IGFBP-2 are high in patients of colon adenoma known to progress to be colon cancer, but these concentrations are reduced by the excision of adenoma (*Journal of Clinical Endocrinology & Metabolism*, 85, 3402-3408, 2000). Over-expression of IGF-II in gastric cancer tissue has been reported (*European Journal of Cancer*, 37, 2257-2263, 2001). It has been reported that, in patients of endometrial cancer after menopause, serum IGF-I concentration is high and the IGFBP-1 concentration is low in comparison with those of healthy persons. On the other hand, a difference was not found regarding the IGFBP-3 concentration (*Endocrine Journal*, 44, 419-424, 1997). It has been reported that, in patients of prostate cancer, IGF-I and IGFBP-2 concentrations are high and IGFBP-3 concentration is low in sera (*British Journal of Cancer*, 76, 1115-1118, 1997, *Urology*, 54, 603-606, 1999, *Journal of Clinical Endocrinology & Metabolism*, 76, 1031-1035, 1993, *Journal of Clinical Endocrinology & Metabolism*, 77, 299-233, 1993), and production of IGF-II, IGFBP-2, IGFBP-4 and IGFBP-5 is accelerated and production of IGFBP-3 is inhibited in the cancer tissue (*Journal of Clinical Endocrinology & Metabolism*, 81, 3774-3782, 1996, *Journal of Clinical Endocrinology & Metabolism*, 81, 411-420, 1996, *Journal of Clinical Endocrinology & Metabolism*, 81, 3783-3792, 1996). Similar changes in the expression of IGF-I and IGFBP have been observed also in sera and cancer tissues of ovarian cancer patients (*Journal of Clinical Endocrinology & Metabolism*, 78, 271-276, 1994, *Journal of Clinical Endocrinology & Metabolism*, 82, 2308-2313, 1997, *British Journal of Cancer*, 73, 1069-1073, 1996).

It has been revealed based on several epidemiological studies that there is a relevancy between the IGF and IGFBP, and the morbidity risk of cancer. It has been reported that highness of morbidity risk and highness of IGF-I concentration in blood and lowness of IGFBP-3 concentration in blood show a positive correlation in solid cancers such as breast cancer, colon cancer, rectum cancer, prostate cancer and lung cancer, that highness of morbidity risk and lowness of IGFBP-3 concentration show a positive correlation in infantile leukemia, and that highness of morbidity risk and highness of the concentration ratio of IGF-I and IGFBP-3 (IGF-I/IGFBP-3) show a positive correlation in breast cancer (*Lancet*, 351, 1393-1396, 1998, *Science*, 279, 563-566, 1998, *Journal of the National Cancer Institute*, 91, 620-625, 1999, *Journal of the National Cancer Institute*, 91, 151-156, 1999, *International Journal of Cancer*, 62, 266-270, 1995, *Epidemiology* 9, 570-573, 1998, *Breast Cancer Research & Treatment*, 47, 111-120, 1998, *International Journal of Cancer*, 83, 15-17, 1999, *International Journal of Cancer*, 80, 494-496, 1999, *British Journal of Cancer*, 76, 1115-1118, 1997).

There are reports also on the relevancy of IGF to prognosis of cancer. In the case of breast cancer, it has been reported that expression of IGF-IR is increased in an estrogen receptor- or progesterone receptor-positive tissue (*Cancer Research*, 52, 1036-1039, 1992). Also, there are cases reporting that the prognosis is getting poor by the expression of IGF-IR (*Cancer Research*, 57, 3079-3083, 1997, *Cancer*, 58, 1159-1164, 1998). It has also been reported that expression of estrogen receptor and expression of IGFBP-3 in the tissue have an inverse correlation (*Cancer Research*, 52, 5100-5103, 1992, *Journal of Cellular Biochemistry*, 52, 196-205, 1993).

Also, abnormal promotion of IGF function has been found in diabetic complications such as diabetic retinopathy and diabetic nephropathy (*Science*, 276, 1706-1709, 1997, *American Journal of Physiology*, 274, F1045-F1053, 1998).

In addition, it has been reported that local expression of IGF-I is observed in rheumatic synovial membrane and also that IGF-I is concerned in the formation of morbid state of reumatoid arthritis (*Arthritis & Rheumatism*, 32, 66-71, 1989, *Journal of Rheumatology*, 22, 275-281, 1995, *Journal of Clinical Endocrinology & Metabolism*, 81, 150-155, 1996, *Arthritis & Rheumatism*, 39, 1556-1565, 1996).

As described above, the IGF family proteins (IGF, IGF-R, IGFBP) including IGF-I and IGF-II are taking important roles in the oncogenesis and proliferation of cancer and also in diabetic complications and rheumatic arthritis. These facts suggest a possibility of effecting diagnosis, prevention and treatment of cancers, diabetic complications, rheumtoid arthritis and the like using IGF family proteins as the target.

Actually, antitumor effects by inhibiting IGF functions have been reported (*Biochimica et Biophysica Acta*, 1332, F105-F126, 1997), for example that tumorigenicity and metastacity of high metastatic human breast cancer cells in mice are reduced and prolongation of survival period is recognized by expressing antisense RNA for IGF-IR (*Cancer Gene Therapy*, 7, 384-395, 2000), and a report that proliferation of human rhabdomyosarcoma cell and human breast cancer cell transplanted into mice is inhibited by an anti-IGF-IR antibody (*Cancer Research*, 54, 5531-5534, 1994, *Journal of Clinical Investigation*, 84, 1418-1423, 1989, *Breast Cancer Research & Treatment*, 22, 101-106, 1992). On the other hand, it has been shown that the anti-IGF-IR antibody inhibits engraftment of a human breast cancer cell showing estrogen-independent growth transplanted into mice, but dose not inhibit engraftment of a human breast cancer cell showing estrogen-dependent growth or proliferation of the engrafted human breast cancer cell, indicating that sufficient antitumor effect cannot be obtained by the inhibition of IGF-IR function alone (*Breast Cancer Research & Treatment*, 22, 101-106, 1992).

Several antibodies are already known as the antibody to IGF (hereinafter referred to as anti-hIGF antibody). As a typical antibody to human IGF-I (hereinafter referred to as anti-hIGF-I antibody), sm1.2 has been reported (*Proceedings of the National Academy of Sciences of the United States of America*, Vol. 81 (1984) 2389-92. It has been revealed that sm1.2 has about 5% cross reactivity with hIGF-II, can detect 100 ng of hIGF-I by western blotting at a concentration of 1 to 2 µg/ml, and inhibits proliferation of a mouse fibroblast cell line BALB/c3T3 by 20 ng/ml of hIGF-I at a concentration of 10 to 30 µg/ml (*Proceedings of the National Academy of Sciences of the United Slates of America*, Vol. 81 (1984) 2389-92, *Journal of Clinical Investigation*, Vol. 99 (1997) 296 1-70.

$Val^{59}$-SmC121 is another anti-hIGF-I antibody, and it has been reported that said antibody does not react with human insulin and hIGF-II, recognizes a peptide containing 10th to 12th position Leu-Val-Asp of hIGF-I, and shows 1 ng/ml of hIGF-I detection sensitivity by a radioimmunoassay using $^{125}$I-hIGF-I (*Journal of endocrinology*, 125, 327-335, 1990).

It has been reported that an anti-hIGF-I antibody 41/81 has 3% cross reactivity with hIGF-II, and shows 1 ng/ml of hIGF-I detection sensitivity by a radioimmunoassay using $^{125}$I-hIGF-I (*FEBS Letters*, 149, 109-112, 1982).

It has been reported that an anti-hIGF-I antibody 35117 has about 0.5% cross reactivity with hIGF-II, can detect 1 µg of hIGF-I by western blotting at a concentration of 1 µg/ml, entirely inhibits proliferation of a mouse fibroblast cell line BALB/c3T3 by hIGF-I at a concentration of 12 µg/ml or more, inhibits auto-phosphorylation of hIGF-IR by 1 µg/ml of hIGF-I at a concentration of 30 µg/ml, and shows 0.1 nM of hIGF-I detection sensitivity by a radioimmunoassay using $^{125}$I-hIGF-I (*Hybridoma*, 16, 513-518, 1997).

It has been reported that an anti-hIGF-I antibody BPL-M23 shows a binding activity of $10.5 \times 10^9$ $M^{-1}$ for hIGF-I, on the other hand, shows respective cross reactivity of 0.8% and 0.0001% with hIGF-II and human insulin, shows reactivity with the IGF of goat, pig, sheep, cattle and rabbit but does not react with the IGF of rat and mouse, and inhibits fat formation for rat adipocyte by hIGF-I (*Journal of Molecular Endocrinology*, 2, 201-206, 1989).

It has been reported that anti-hIGF-I antibodies 7A1, 1B3, 4C1 and 5A7 recognize different epitopes of the C and D domains of hIGF-I, and show respective cross reactivity of 6.6%, 0.83%, 12% and 1.2% with hIGF-II (*Hybridoma*, 12, 737-744, 1993).

It has been reported that 3D1/2/1 reacts with the IGF-I of human and guinea pig but does not react with the IGF-I of rabbit, rat and mouse, and shows a cross reactivity of 7% with hIGF-II (*Journal of Clinical of Metabolism*, 54, 474-476, 1982).

As a typical antibody to human IGF-II (hereinafter referred to as anti-hIGF-II antibody), an S1F2 has been reported. It has been revealed that the S1F2 has a cross reactivity of about 10% with hIGF-I, can detect 10 to 100 ng of hIGF-II by western blotting at a concentration of 1 µg/ml, and inhibits the DNA synthesis promoting function of human fibroblast by 100 ng/ml of hIGF-II at a concentration of 100 µg/ml (*Diabetes Research and Clinical Practice*, 7, S21-S27, 1989, *Endocrinology*, 124, 870-877, 1989).

It has been reported that anti-hIGF-II antibodies 2H11, 2B11, ID5 and ID9 react with hIGF-II but do not react with hIGF-I, and can determine 1 ng/ml of hIGF-II by competitive enzyme immunoassay (hereinafter referred to as ELISA) (Japanese published unexamined application No. 252987/93).

In addition, it is known that when an antibody of a non-human animal, for example a mouse antibody, is administered to human, the administered mouse antibody is recognized as a foreign body, which induces in the human body a human antibody to the mouse antibody (human anti-mouse antibody: hereinafter referred to as HAMA). It is known that the HAMA reacting with the administered mouse antibody to induce side effects (*Journal of Clinical Oncology*, 2, 881-891, 1984; *Blood*, 65, 1349-1363, 1985; *Journal of the National Cancer Institute*, 80, 932-936, 1988; *Proceedings of the National Academy of Sciences of the United States of America*, 82, 1242-1246, 1985), promotes disappearance of the administered mouse antibody from the body (*Journal of Nuclear Medicine*, 26, 1011-1023, 1985; *Blood*, 65, 1349-1363, 1985; *Journal of the National Cancer Institute*, 80, 937-942, 1988) and reduces therapeutic effect of the mouse antibody (*Journal of Immunology*, 135, 1530-1535, 1985; *Cancer Research* 46, 6489-6493, 1986).

In order to solve these problems, attempts have been made to convert antibodies of non-human animals into humanized antibodies such as human chimeric antibodies and human complementarity determining region (hereinafter referred to as CDR)-grafted antibodies by using gene recombination techniques. The human chimeric antibody is an antibody wherein variable region (hereinafter referred to as V region) of the antibody is an antibody of a non-human animal and constant region (hereinafter referred to as C region) is a human antibody (*Proceedings of the National Academy of Sciences of the United States of America*, 81, 6851-6855, 1984), and the human CDR-grafted antibody is an antibody wherein amino acid sequence of CDR in the V region of an antibody of a non-human animal is grafted to an appropriate position of a human antibody (*Nature*, 321, 522-525, 1986). In comparison with antibodies of non-human animals such as mouse antibody, these humanized antibodies are more advantageous in clinical applications to human. For example, regarding immunogenicity and stability in blood, it has been reported that blood half-life of a human chimeric antibody was extended about 6 times in comparison with a mouse antibody when administered to human (*Proceeding of the National Academy of Sciences of the United States of America*, 86, 4220-4224, 1989). As to a human CDR-grafted antibody, it has been reported that its immunogenicity was reduced and blood half-life was extended in comparison with a mouse antibody in a study using a monkey (*Cancer Research*, 56, 1118-1125, 1996; *Immunology*, 85, 668-674, 1995). Thus, it is expected that humanized antibodies have less side effects in comparison with antibodies of non-human animals, and their-therapeutic effects are maintained for a long period of time. Further, humanized antibodies are prepared by using gene recombination techniques, and they can be prepared as various forms of molecules. For example, when a γ-1 subclass is used as the heavy chain (hereinafter referred to as H chain) C region of a human antibody, a humanized antibody which is stable in blood and has high effector activities such as antibody-dependent cellular cytotoxicity and the like can be prepared (*Cancer Research*, 56, 1118-1125, 1996). A humanized antibody having high effector activity is markedly useful when destruction of targets such as cancer is desired. On the other hand, in the case that merely a target-neutralizing function alone is required, or in the case that there is a possibility of causing a side effect due to destruction of a target by an effector activity, a γ4 subclass is suitably used as the H chain C region of a human antibody, because γ4 subclass generally has low effector activity (*Journal of Experimental Medicine*, 166, 1351-1361, 1987; *Journal of Experimental Medicine*, 168, 127-142, 1988), and side effects can be avoided, and further extension of blood half-life in comparison with a mouse antibody can be expected (*Immunology*, 85, 668-674, 1995). In addition, with the recent advances in protein engineering and genetic engineering, it became possible to prepare antibody fragments having more smaller molecular weight such as Fab, Fab', F(ab')$_2$, scFv (*Science*, 242, 423-426, 1988), dsFv (*Molecular Immunology*, 32, 249-258, 1995) and CDR-containing peptide (*Journal of Biological Chemistry*, 271, 2966-2971, 1996) from antibodies including humanized antibodies. Since these antibody fragments have smaller molecular weight in comparison with whole antibody molecules, they have superior transferring property to target tissues (*Cancer Research*, 52, 3402-3408, 1992).

Based on the above, the IGF family proteins which take important roles in the oncogenesis and proliferation of cancer and also in diabetic complications and rheumatoid arthritis are controlling these diseases through complicated entanglement of growth factors including insulin, IGF-I and IGF-II, receptors including insulin receptor, IGF-IR and IGF-IIR and IGFBP. Accordingly, it is difficult to suppress these diseases completely by inhibiting a part of these interactions. Though there are many reports on antibodies which recognize IGF-I and/or IGF-II considered to be useful as medicament, there are no reports on antibodies which can simultaneously inhibit functions of IGF-I and IGF-II by strongly binding to IGF-I and IGF-II.

In addition, as antibodies to be used for the clinical application to human, humanized antibodies are desirable than antibodies of a non-human animal such as mouse antibody. However, there are no reports on the preparation of recombinant antibodies such as humanized antibody as an anti-hIGF antibody, and also on antibody fragments thereof.

DISCLOSURE OF THE INVENTION

It is known that hIGF family-mediated cell-growth is working in variou kinds of cancer cells, and it is expected that inhibition of hIGF-mediated signal transduction, in the case it is attainable, is effective for treating diseases such as proliferation and metastasis of solid cancers, diabetic complications and rheumatoid arthritis in human.

An object of the present invention is to obtain a substance which inhibits cell growth via IGF by blocking hIGF family-mediated signal transduction, and to further provide application methods of said substance.

The present invention relates to the following (1) to (24).

(1) An antibody or an antibody fragment thereof, which specifically binds to IGF-I and IGF-II to inhibit functions of human IGF-I and human IGF-II and has the binding activity with a binding constant of $5\times10^9$ $M^{-1}$ or more measured with a biosensor BIACORE.

(2) The antibody or the antibody fragment thereof according to the above (1), wherein the binding activity to human IGF-I and the binding activity to human IGF-II are the same degree.

(3) The antibody or the antibody fragment thereof according to the above (1) or (2), wherein CDR1, CDR2 and CDR3 of heavy chain variable region (VH) of an antibody or an antibody fragment thereof comprise amino acid sequences represented by SEQ ID NOS: 5, 6 and 7 respectively, and/or CDR1, CDR2 and CDR3 of light chain variable region (VL) of the antibody or an antibody fragment comprise amino acid sequences represented by SEQ ID NOS: 8, 9 and 10 respectively.

(4) The antibody or the antibody fragment thereof according to any one of the above (1) to (3), wherein the antibody is an antibody of a non-human animal or a recombinant antibody.

(5) The antibody or the antibody fragment thereof according to the above (4), wherein the recombinant antibody is selected from the group consisting of a human chimeric antibody, a human CDR-grafted antibody and a human antibody.

(6) The antibody or the antibody fragment thereof according to the above (4), wherein VH of the antibody of a non-human animal comprises the amino acid sequence represented by SEQ ID NO: 2, and/or VL of the antibody of a non-human animal somprises the amino acid sequence represented by SEQ ID NO: 4.

(7) The antibody or the antibody fragment thereof according to the above (3) or (6), wherein the antibody of a non-human animal is produced by a hybridoma KM1468 (FERM BP-7978).

(8) The antibody or the antibody fragment thereof according to the above (5), wherein VH of the human chimeric antibody comprises the amino acid sequence represented by SEQ ID NO: 2, and/or VL of the human chimeric antibody comprises the amino acid sequence represented by SEQ ID NO: 4.

(9) The antibody or the antibody fragment thereof according to the above (5) or (8), wherein the human chimeric antibody comprises VH and/or VL of the antibody produced by KM1468 (FERM BP-7978).

(10) The antibody or the antibody fragment thereof according to any one of the above (5), (8) and (9), wherein the human chimeric antibody comprises a constant region of a human antibody.

(11) The antibody or the antibody fragment thereof according to the above (10), wherein the constant region of a human antibody comprises the constant region of a human antibody IgG1 class and/or κ class.

(12) The antibody or the antibody fragment thereof according to any one of the above (5) and (8) to (11), wherein the human chimeric antibody is produced by a transformant KM3002 (FERM BP-7996).

(13) The antibody or the antibody fragment thereof according to the above (4), wherein CDR1, CDR2 and CDR3 of VH of the human CDR-grafted antibody comprises the amino acid sequences represented by SEQ ID NOS: 5, 6 and 7 respectively, and/or CDR1, CDR2 and CDR3 of VL of the human CDR-grafted antibody comprises the amino acid sequences of SEQ ID NOS: 8, 9 and 10 respectively.

(14) The antibody or the antibody fragment thereof according to the above (5) or (13), wherein the human CDR-grafted antibody comprises CDR of VH of the antibody produced by KM1468 (FERM BP-7978) and/or CDR of VL of the antibody produced by KM1468 (FERM BP-7978).

(15) The antibody or the antibody fragment thereof according to any one of the above (4), (13) and (14), wherein the human CDR-grafted antibody comprises a constant region of a human antibody.

(16) The antibody or the antibody fragment thereof according to the above (15), wherein the constant region of a human antibody comprises the constant region of a human antibody IgG1 class and/or κ class.

(17) The antibody fragment according to any one of the above (1) to (16), wherein the antibody fragment is selected from the group consisting of Fab, Fab', F(ab')$_2$, single chain antibody (scFv), dimerized V region (diabody), disulfide-stabilized V region (dsFv) and a CDR-containing peptide.

(18) A DNA coding for the antibody or antibody fragment thereof according to any one of the above (1) to (17).

(19) A recombinant vector which contains the DNA according to the above (18).

(20) A transformant which is obtained by introducing the recombinant vector according to the above (19) into a host cell.

(21) A method for producing an antibody or the antibody fragment thereof, which comprises culturing the transformant according to the above (20) in a medium to produce and accumulate the antibody or the antibody fragment thereof according to any one of the above (1) to (16) in a culture, and recovering the antibody or the antibody fragment thereof from the culture.

(22) A medicament which comprises at least one of the antibody and the antibody fragment thereof according to any one of the above (1) to (17) as the active ingredient.

(23) A therapeutic agent against a human IGF-related disease or a disease whose morbid state progresses by abnormal promotion of human IGF production, which comprises at least one of the antibody and the antibody fragment thereof according to any one of the above (1) to (17) as the active ingredient.

(24) A diagnostic agent for a human IGF-related disease or a disease whose morbid state progresses by abnormal promotion of human IGF production, which comprises at least one of the antibody and an antibody fragment thereof according to any one of the above (1) to (17).

Examples of the anti-hIGF antibody of the present invention include an antibody specifically binds to human IGF-I and human IGF-II to inhibit functions of human IGF-I and human IGF-II which has the binding activity with a binding constant of $5 \times 10^9$ M$^{-1}$ or more measured with a biosensor BIACORE, and particularly desirable is an antibody in which the binding activity to hIGF-I and the binding activity to hIGF-II are almost the same and which inhibits functions of hIGF-I and hIGF-II.

The term "the binding activity to hIGF-I and the binding activity to hIGF-II are almost the same" means that the antibody can bind to both hIGF-I and hIGF-II equivalently. The equivalent binding can be represented as the relative value by numerating binding activity of the antibody to hIGF-I or hIGF-II. The equivalent binding activity means that when the binding activity of the antibody to hIGF-I is defined as 1, the binding activity to hIGF-II is 0.1 to 10, preferably 0.2 to 5, more preferably 0.5 to 2, most preferably 1. Examples of the index of the binding activity include a binding constant (hereinafter referred also to as $K_A$) measured by a biosensor method which uses the principle of surface plasmon resonance or the like (hereinafter referred to as biosensor BIACORE).

Examples of the antibody of the present invention include an antibody which recognizes an epitope existing in natural type hIGF-I and hIGF-II and an antibody which recognizes the three-dimensional structure of natural type hIGF-I and hIGF-II. The examples further include an antibody which show cross reactivity with IGF of non-human organism.

Regarding the function of hIGF-I and hIGF-II, it may be any function in which hIGF-I and hIGF-II are concerned, such as control of proliferation, differentiation or apoptosis of epithelial cells of the breast, prostate, lungs, colon and the like.

Examples of the anti-hIGF antibody of the present invention include an antibody of a non-human animal, a recombinant antibody and an antibody fragment thereof.

Examples of the antibody of a non-human animal include a polyclonal antibody and a monoclonal antibody, preferable is a monoclonal antibody.

The monoclonal antibody of a non-human animal according to the present invention can be obtained by immunizing a non-human animal with hIGF, preparing hybridomas from an antibody-producing cell of the immunized animal and a myeloma cell, selecting a monoclonal hybridoma, culturing the monoclonal hybridoma and then purifying it from the culture supernatant. As the non-human animal, any one of mouse, rat, hamster, rabbit and the like can be used with the proviso that hybridomas can be prepared therefrom.

Preferred examples of the antibody of the present invention include antibodies in which CDR1, CDR2 and CDR3 of VH comprise amino acid sequences of SEQ ID NOS: 5, 6 and 7 respectively, and/or CDR1, CDR2 and CDR3 of VL comprise the sequences of SEQ ID NOS: 8, 9 and 10 respectively.

Specific examples of the monoclonal antibody of a non-human animal according to the present invention include a rat antibody KM1468 which is produced by a hybridoma KM1468 (FERM BP-7978).

Examples of the recombinant antibody of the present invention include a humanized antibody, a human antibody and the like.

Examples of the humanized antibody include a human chimeric antibody, a human CDR-grafted antibody and the like.

The human chimeric antibody is an antibody which comprises VH and VL of an antibody of a non-human animal and CH and CL of a human antibody.

The human chimeric antibody of the present invention can be produced by preparing cDNAs coding for VH and VL from a hybridoma capable of producing a monoclonal antibody which has the ability to inhibit functions of human IGF-I and human IGF-II by specifically binding to human IGF-I and human IGF-II and has the binding activity with a binding constant of $5 \times 10^9$ $M^{-1}$ or more measured with a biosensor BIACORE, constructing a human chimeric antibody expression vector by respectively inserting the cDNAs into an expression vector for animal cell use having genes coding for CH and CL of a human antibody, and then expressing by introducing the vector into an animal cell.

The CH of the human chimeric antibody may be any region with the proviso that it belongs to human immunoglobulin (hereinafter referred to as hIg), but preferably an hIgG class, and anyone of hIgG1, hIgG2, hIgG3 and hIgG4 subclasses belonging to the hIgG class can be used. Also, the CL of the human chimeric antibody may be any region with the proviso that it belongs to the hIg, and those of κ class or λ class can be used.

Examples of the human chimeric antibody which binds to hIGF-I and hIGF-II according to the present invention (to be referred to as anti-hIGF chimeric antibody hereinafter) include an anti-hIGF chimeric antibody containing antibody VH CDR1, CDR2 and CDR3, respectively comprising the amino acid sequences represented by SEQ ID NOS: 5, 6 and 7 and/or VL CDR1, CDR2 and CDR3, respectively comprising the amino acid sequences represented by SEQ ID NOS: 8, 9 and 10, an anti-hIGF chimeric antibody containing VH and/or VL of the monoclonal antibody produced by the hybridoma KM1468, an anti-hIGF chimeric antibody in which the antibody VH contains the 1st to 118th positions of the amino acid sequence represented by SEQ ID NO: 2 and/or the VL contains the 1st to 107th positions of the amino acid sequence represented by SEQ ID NO: 4, and an anti-hIGF chimeric antibody in which the antibody VH comprises the amino acid sequence represented by SEQ ID NO: 2, the human antibody CH comprises an amino acid sequence of hIgG1 subclass, the antibody VL comprises the amino acid sequence represented by SEQ ID NO: 4 and the human antibody CL comprises an amino acid sequence of κ class, and specifically, the anti-hIGF chimeric antibody KM3002 produced by a transformant KM3002 (FERM BP-7996) is mentioned. Antibodies in which one or more amino acids of these amino acid sequences are deleted, added, substituted or inserted, and which have the ability to inhibit functions of human IGF-I and human IGF-II by specifically binding to human IGF-I and human IGF-II and have the binding activity with a binding constant of $5 \times 10^9$ $M^{-1}$ or more measured with a biosensor BIACORE are also included in the antibody of the invention.

The human CDR-grafted antibody is an antibody in which CDR amino acid sequences of VH and VL of an antibody of a non-human animal are grafted to appropriate positions of VH and VL of a human antibody.

The human CDR-grafted antibody of the present invention can be produced by constructing cDNAs coding for V regions prepared by grafting CDR amino acid sequences of VH and VL of an antibody of a non-human animal, which has the ability to inhibit functions of human IGF-I and human IGF-II by specifically binding to human IGF-I and human IGF-II and has the binding activity with a binding constant of $5 \times 10^9$ $M^{-1}$ or more measured with a biosensor BIACORE, to the FR of VH and VL of an optional human antibody, constructing a human CDR-grafted antibody expression vector by respectively inserting the cDNAs into an expression vector for animal cell use having a gene coding for CH and CL of a human antibody, and then expressing by introducing the vector into an animal cell.

The CH of the human CDR-grafted antibody may be any region with the proviso that it belongs to hIg, but preferably an hIgG class, and any one of hIgG1, hIgG2, hIgG3 and hIgG4 subclasses belonging to the hIgG class can be used. Also, the CL of the human CDR-grafted antibody may be any region with the proviso that it belongs to the hIg, and those of κ class or λ class can be used.

Examples of the human CDR-grafted antibody which binds to hIGF-I and hIGF-II according to the present invention (hereinafter referred to as anti-hIGF CDR-grafted antibody) include an anti-hIGF CDR-grafted antibody containing antibody VH CDR1, CDR2 and CDR3, respectively comprising the amino acid sequences represented by SEQ ID NOS: 5, 6 and 7 and/or VL CDR1, CDR2 and CDR3, respectively comprising the amino acid sequences represented by SEQ ID NOS: 8, 9 and 10, an anti-hIGF CDR-grafted antibody containing VH CDR and/or VL CDR of the monoclonal antibody produced by the hybridoma KM1468, an anti-hIGF CDR-grafted antibody in which the antibody VH contains the 1st to 118th positions of the amino acid sequence represented by SEQ ID NO: 15 and/or the VL contains the 1st to 107th positions of the amino acid sequence represented by SEQ ID NO: 16, and an anti-hIGF CDR-grafted antibody in which the antibody VH comprises the amino acid sequence represented by SEQ ID NO: 15, the human antibody CH comprises an amino acid sequence of hIgG1 subclass, the antibody VL comprises the amino acid sequence represented by SEQ ID NO: 16 and the human antibody CL comprises an amino acid sequence of κ class. Antibodies in which one or more amino acids of these amino acid sequences are deleted, added, substituted or inserted, and which have the ability to inhibit functions of human IGF-I and human IGF-II by specifically binding to human IGF-I and human IGF-II and have the binding activity with a binding constant of $5 \times 10^9$ $M^{-1}$ or more measured with a biosensor BIACORE are also included in the antibody of the present invention.

Though the human antibody generally means an antibody naturally existed in the human body, it also includes antibodies obtained from a human antibody phage library and a human antibody-producing transgenic animal prepared based on the recent advance in the genetic engineering, cell engineering and embryo engineering techniques.

Regarding the antibody existed in the human body, for example, a lymphocyte capable of producing said antibody can be cultured by isolating a human peripheral lymphocyte, immortalizing by infecting with EB virus or the like and then cloning, and said antibody can be purified from the culture supernatant.

The human antibody phage library is a library in which antibody fragments of Fab, scFv and the like are expressed on the phage surface by inserting an antibody gene prepared from human B cell into a phage gene. A phage expressing antibody, fragments having desired antigen binding activity on the surface can be recovered from said library using the binding activity to an antigen-immobilized substrate as an index. Said antibody fragments can be further converted into a human antibody molecule comprising two full length H chains and two full length L chains by genetic engineering techniques.

The human antibody-producing transgenic animal means an animal in which a human antibody gene is integrated into its cells. For example, a human antibody-producing transgenic mouse can be prepared by introducing a human antibody gene into a mouse ES cell, transplanting said ES cell into early embryo of a mouse and then developing. Regarding the method for preparing a human antibody from a human antibody-producing transgenic animal, the human antibody can be produced and accumulated in a culture supernatant by culturing a human antibody-producing hybridoma obtained by a hybridoma preparation method generally carried out in non-human animals.

As the antibody fragments of the present invention, Fab, Fab', F(ab')$_2$, scFv, diabody, dsFv, a CDR-containing peptide and the like can be exemplified.

Among fragments obtained by treating IgG with a protease papain (digested at the 224th amino acid residue of H chain), Fab is an antibody fragment of about 50,000 in molecular weight having an antigen binding activity in which about half of the H chain N-terminal side and full length L chain are bonded through disulfide bond.

The Fab of the present invention can be prepared by treating an antibody which binds to hIGF-I and hIGF-II with a protease papain. Alternatively, Fab can be produced by inserting a DNA coding for the Fab of said antibody into an expression vector for prokaryote or an expression vector for eucaryote and expressing by introducing said vector into a prokaryote or a eucaryote.

Among fragments obtained by treating IgG with a protease pepsin (digested at the 234th amino acid residue of H chain), F(ab')$_2$ is an antibody fragment of about 100,000 in molecular weight having an antigen binding activity, which is slightly larger than a product in which Fab fragments are bonded via disulfide bond of the hinge region.

The F(ab')$_2$ of the present invention can be prepared by treating an antibody which binds to hIGF-I and hIGF-II with a protease pepsin. Alternatively, it can be prepared by carrying out thioether bonding or disulfide bonding of the Fab' fragments described below.

Fab' is an antibody fragment of about 50,000 in molecular weight having an antigen binding activity obtained by digesting the hinge region disulfide bond of the aforementioned F(ab')$_2$.

The Fab' of the present invention can be obtained by treating the F(ab')$_2$ of the present invention which binds to hIGF-I and hIGF-II with a reducing agent dithiothreitol. Alternatively, Fab' can be produced by inserting a DNA coding for the Fab' fragment of said antibody into an expression vector for prokaryote or an expression vector for eucaryote and expressing by introducing said vector into a prokaryote or a eucaryote.

The scFv is an antibody fragment having an antigen binding activity, which is a VH-P-VL or VL-P-VH polypeptide prepared by connecting one VH and one VL using an appropriate peptide linker (to be referred to as P hereinafter).

The scFv of the present invention can be obtained by preparing cDNAs coding for VH and VL of the antibody of the present invention which binds to hIGF-I and hIGF-II, thereby constructing a DNA coding for scFv, inserting said DNA into an expression vector for prokaryote or an expression vector for eucaryote and expressing by introducing said expression vector into a prokaryote or a eucaryote.

Diabody is an antibody fragment in which scFv is dimerized and which has divalent antigen binding activities. The divalent antigen binding activities may be the same, or one of them can be used as a different antigen binding activity.

The diabody of the present invention can be obtained by preparing cDNAs coding for VH and VL of the antibody of the present invention which binds to hIGF-I and hIGF-II, constructing a DNA coding for scFv in such a manner that length of the amino acid sequence of P becomes 8 residues or less, inserting said DNA into an expression vector for prokaryote or an expression vector for eucaryote and expressing by introducing said expression vector into a prokaryote or a eucaryote.

The dsFv is a product in which polypeptides prepared by replacing one amino acid residue in VH and one in VL by cysteine residues are bonded via the disulfide bond between said cysteine residues. The amino acid residues to be replaced by cysteine residues can be selected based on the estimation of three-dimensional structure of the antibody in accordance with the method shown by Reiter et al. (*Protein Engineering*, 7, 697-704, 1994).

The dsFv of the present invention can be obtained by preparing cDNAs coding for VH and VL of the antibody of the present invention which binds to hIGF-I hIGF-II, constructing a DNA coding for dsFv, inserting said DNA into an expression vector for prokaryote or an expression vector for eucaryote and expressing by introducing said expression vector into a prokaryote or a eucaryote.

A CDR-containing peptide comprises at least one or more of CDR of VH or VL. Peptides containing plural of CDRs can be linked directly or via an appropriate peptide linker.

The CDR-containing peptide of the present invention can be obtained by constructing a DNA coding for CDRs of VH and VL of the antibody of the invention which binds to hIGF-I and hIGF-II, inserting said DNA into an expression vector for prokaryote or an expression vector for eucaryote and expressing by introducing said expression vector into a prokaryote or a eucaryote.

The CDR-containing peptide can also be produced by chemical synthesis method such as Fmoc method (fluorenylmethoxycarbonyl method) and tBoc method (t-butyloxycarbonyl method.

Antibody derivatives prepared by binding a radioisotope, a low molecular drug, a high molecular drug, a protein and the like, chemically or by a genetic engineering technique, to the antibody of the invention which binds to hIGF-I and hIGF-II and antibody fragments thereof are included in the antibody of the present invention.

Derivatives of the antibody of the present invention can be produced by binding a radioisotope, a low molecular drug, a high molecular drug, a protein and the like to H chain or L chain N-terminal side or C-terminal side of the antibody of the present invention which binds to hIGF-I and hIGF-II and antibody fragments thereof, an appropriate substituent group or side chain of the antibody and antibody fragments or a sugar chain in the antibody and antibody fragments, by chemical techniques (Introduction to Antibody Engineering, written by O. Kanemitsu, published by Chijin Shokan, 1994).

They can also be produced by connecting a DNA coding for the antibody of the present invention which binds to hIGF-I and hIGF-II or an antibody fragment thereof and a DNA coding for a protein to be bonded and inserting into an expression vector, and expressing by introducing said expression vector into an appropriate host cell.

As the radioisotope, $^{131}$I, $^{125}$I and the like can be exemplified, and they can be connected to the antibody for example by the chloramine T method.

Examples of the low molecular drug include antitumor agents such as alkylating agents including nitrogen mustard, cyclophosphamide and the like, metabolic antagonists including 5-fluorouracil, methotrexate and the like, antibiotics including daunomycin, bleomycin, mitomycin C, daunorubicin, doxorubicin and the like, plant alkaloids including vincristine, vinblastine, vindesine and the like, and hormone agents including tamoxifen, dexamethasone and the like (Clinical Tumor Science, edited by Japan Clinical Tumor Research Association, published by Gan to Kagaku Ryohosha, 1996), or anti-inflammatory agents such as steroid agents including hydrocortisone, prednisone and the like, non-steroidal agents including aspirin, indometacin and the like, immunomodulators including aurothiomalate, penicillamine and the like, immunosuppressants including cyclophosphamide, azathioprine and the like, and anti-inflammatory such as antihistaminics including chlorpheniramine maleate, clemastine and the like (Inflammation and Anti-inflammation Therapy, published by Ishiyaku Shuppan, 1982). For example, as a method for connecting daunomycin and an antibody, a method in which amino groups of daunomycin and the antibody are connected via glutaraldehyde and a method in which amino group of daunomycin and carboxyl group of the antibody are connected via a water-soluble carbodiimide can be exemplified.

Examples of the high molecular drug include polyethylene glycol (to be referred to as PEG hereinafter), albumin, dextran, polyoxyethylene, styrene maleic acid copolymer, polyvinyl pyrrolidone, pyran copolymer, hydroxypropylmethacrylamide and the like. By connecting these high molecular compounds to antibodies and antibody fragments, various effects can be expected, for example, (1) improvement of stability for various chemical, physical or biological factors, (2) significant extension of blood half-life, (3) disappearance of immunogenicity and suppression of antibody production (Bioconjugate Medicaments, published by Hirokawa Shoten, 1993). For example, as a method for connecting PEG to an antibody, a method in which they are allowed to undergo the reaction with a PEG modifying agent can be exemplified (Bioconjugate Medicaments, published by Hirokawa Shoten, 1993). Examples of the PEG modifying agent include an agent for modifying ϵ-amino group of lysine (Japanese published unexamined application No. 178926/86), an agent for modifying carboxyl group of aspartic acid and glutamic acid (Japanese published unexamined application No. 23587/81), an agent for modifying guanidino group of arginine (Japanese published unexamined application No. 117920/90) and the like.

Examples of the protein include cytokines which activate immunocompetent cells such as human interleukin 2 (hereinafter referred to as hIL-2), human granulocyte macrophage colony-stimulating factor (hereinafter referred to as hGM-CSF), human macrophage colony-stimulating factor (to be referred to as hM-CSF hereinafter), human interleukin 12 (hereinafter referred to as hIL-12) and the like. In addition, toxins having the activity to directly damage cancer cells such as ricin and diphtheria toxin can also be used. For example, in the case of a fusion antibody with a protein, the fusion antibody can be produced by connecting a cDNA coding for a protein to another cDNA coding for an antibody or antibody fragment, thereby constructing a DNA coding for a fusion antibody, inserting said DNA into an expression vector for prokaryote or an expression vector for eucaryote and expressing by introducing said expression vector into a prokaryote or a eucaryote.

Regarding the antibody of the present invention to hIGF-I and hIGF-II and antibody fragments thereof, their binding activity to hIGF-I and hIGF-II and activity to inhibit functions of hIGF-I and hIGF-II can be evaluated by measuring ELISA (Antibodies: A Laboratory Manual, Cold Spring Harbor Laboratory, Chapter 14, 1988; Monoclonal Antibodies: Principles and Practice, Academic Press Limited, 1996), $K_A$ measured with a biosensor BIACORE (*Journal of Immunological Methods,* 145, 229-240, 1991), inhibitory activity for cell proliferation by hIGF-I and hIGF-II (*Cancer Research,* 48, 4083-4092, 1988) and the like.

As the diseases in which the hIGF of the present invention is concerned and diseases in which their morbid states progress by abnormal promotion of hIGF production, any disease is included with the proviso that it is a disease in which its morbid state progresses by abnormal cell proliferation caused by hIGF, regardless of mild or serious-illness, and the specific examples include cancer, diabetic complication, rheumatoid arthritis and the like.

The following describes preparation method and activity evaluation of an antibody or an antibody fragment thereof which specifically binds to human IGF-I and human IGF-II, has the ability to inhibit functions of human IGF-I and human IGF-II and has binding activity with a binding constant of $5 \times 10^9$ M$^{-1}$ or more measured with a biosensor BIACORE.

1. Preparation of Anti-hIGF Monoclonal Antibody of a Non-Human Animal (1) Preparation of Antigen A recombinant hIGF protein is obtained by introducing an expression vector containing a cDNA coding for hIGF into *Escherichia coli,* a yeast, an insect cell, an animal cell or the like and expressing the protein therein. Alternatively, a synthetic peptide having an hIGF partial sequence can also be used as the antigen.

As the partial peptide for antigen, a protein partial sequence of approximately 5 to 30 residues is selected. For obtaining an antibody which recognizes said protein under a state of having non-denatured natural structure, it is necessary to select, as an antigen peptide, a partial sequence existing on the protein surface in view of three-dimensional structure. The moiety existing on the protein surface in view of three-dimensional structure can be assumed by estimating a partial sequence being high hydrophilic using a commercially available protein sequence analyzing software such as Genetyx Mac. That is, this is because generally a low hydrophilic region is present in inner part of protein in view of three-dimensional structure in many cases, while a high hydrophilic region is present on the protein surface. In addition, N-terminus and C-terminus of a protein are present on the protein surface in many cases. However, the partial peptide selected in this manner is not always used as an antigen which establishes desired antibody.

Cysteine is added to a terminus of the partial peptide to crosslink with a protein. When an inner sequence of the protein is selected, N-terminus of the peptide is acetylated and the C-terminus is subjected to amidation as required.

The partial peptide can be synthesized by a general liquid phase and solid phase peptide synthesis methods, a method in which these are optionally combined or a method in accordance therewith (The Peptides, Analysis, Synthesis, Biology, Vol. 1, 1979; Vol. 2, 1980; Vol. 3, 1981, Academic Press; Basics and Experimentations of Peptide Synthesis, Maruzen, 1985; Development of Medicaments, a second series, Vol. 14, Peptide Synthesis, Hirokawa Shoten, 1991; *International Journal of Peptide & Protein Research*, 35, 161-214, 1990).

In addition, an automatic peptide synthesizer can also be used. Synthesis of a peptide by a peptide synthesizer can be carried out on a commercially available peptide synthesizer such as a peptide synthesizer manufactured by Shimadzu, a peptide synthesizer manufactured by Applied Biosystems, Inc. (hereinafter referred to as ABI), a peptide synthesizer manufactured by Advanced ChemTech Inc. (hereinafter referred to as ACT) or the like, in accordance with each synthesis program using Nα-Fmoc-amino acids, Nα-Boc-amino acids or the like whose side chains are properly protected.

The protected amino acids to be used as the material and carrier resins can be purchased from ABI, Shimadzu, Kokusan Kagaku, Nova Biochem, Watanabe Kagaku, ACT, Peptide Research Laboratory, etc. In addition, the protected amino acids to be used as the material, protected organic acids and protected organic amines can be synthesized by reported synthesizing methods or in accordance therewith (The Peptides, Analysis, Synthesis, Biology, Vol. 1, 1979; Vol. 2, 1980; Vol. 3, 1981, Academic Press; Basics and Experimentations of Peptide Synthesis, Maruzen, 1985; Development of Medicaments, a second series, Vol. 14, Peptide Synthesis, Hirokawa Shoten, 1991; *International Journal of Peptide & Protein Research*, 35, 161-214, 1990).

(2) Immunization of Animal and Preparation of Antibody Producing Cells

Any one of mouse, rat, hamster, rabbit ant the like can be used as the animal to be used in the immunization, with the proviso that a hybridoma can be prepared therefrom. An example which uses mouse and rat is described below.

Mice or rats of 3 to 20 weeks of age are immunized with the antigen prepared in the above 1(1), and antibody producing cells are collected from the spleen, lymph node or peripheral blood of the animals. The immunization is carried out several times by administering the antigen together with an appropriate adjuvant to the animals subcutaneously, intravenously or intraperitoneally. Examples of the adjuvant include Freund's complete adjuvant and aluminum hydroxide gel plus pertussis vaccine can be cited. Also, a conjugate with carrier protein such as bovine serum albumin (hereinafter referred to as BSA) and keyhole limpet hemocyanin (hereinafter referred to as KLH) can be prepared and used as the immunogen. Three to seven days after each administration of antigen, a blood sample is taken from the venous plexus of the fundus of the eye or from the tail vein of each immunized animal, the sample is tested as to whether it is reactive with the hIGF used as the antigen by ELISA or the like, and a mouse or rat whose serum shows a sufficient antibody titer is used as a supply source of antibody producing cells. On the 3rd to 7th day after final administration of the antigen, the spleen or the like is excised from the immunized mouse or rat in accordance with a known method (Antibodies—A Laboratory Manual, Cold Spring Harbor Laboratory, 1988), and the antibody producing cells are fused with myeloma cells.

(3) Preparation of Myeloma Cells

As the myeloma cells, any myeloma cell which can proliferate in vitro can be used, such as the 8-azaguanine-resistant mouse derived myeloma cell lines P3-X63Ag8-U1 (P3-U1) (*European Journal of Immunology*, 6, 511-519, 1976), SP2/O-Ag14 (SP-2) (*Nature*, 276, 269-270, 1978), P3-X63-Ag8653 (653) (*Journal of Immunology*, 123, 1548-1550, 1979) or P3-X63-Ag8 (X63) (*Nature*, 256, 495-497, 1975). Regarding culturing and sub-culturing of these cell strains, $2 \times 10^7$ or more of the cells are prepared until the time of cell fusion in accordance with a known method (Antibodies—A Laboratory Manual, Cold Spring Harbor Laboratory, 1988).

(4) Cell Fusion

The antibody producing cells and myeloma cells obtained in the above are washed, mixed with cell aggregating medium such as polyethylene glycol-1000 (to be referred to as PEG-1000 hereinafter) to effect fusion of the cells and then suspended in a medium. Modified Eagle's medium (hereinafter referred to as MEM), phosphate buffered saline (hereinafter referred to as PBS) or the like is used for the washing of cells. Also, in order to selectively obtain a fused cell of interest, HAT medium {normal medium [a medium prepared by adding 1.5 mM glutamine, 50 μM 2-mercaptoethanol, 10 μg/ml gentamicin and 10% fetal calf serum (hereinafter referred to as FCS) to RPMI-1640 medium] further supplemented with 0.1 mM hypoxanthine, 15 μM thymidine and 0.4 μM aminopterin} is used as the medium in which fused cells are to be suspended.

After the culturing, a portion of the culture supernatant is taken, and a sample which reacts with the antigen protein but does not react with non-antigen proteins is selected by ELISA. Next, single cell cloning is carried out by limiting dilution method, and a cell showing stably high antibody titer by ELISA is selected as a monoclonal antibody producing hybridoma.

(5) Selection of Hybridoma

Selection of a hybridoma which produces an anti-hIGF monoclonal antibody is carried out in accordance with a known method (Antibodies—A Laboratory Manual, Cold Spring Harbor Laboratory, 1988) by the ELISA described in the following. These methods render possible measurement of the binding activity of antibodies contained in the culture supernatants of transformants which produce the anti-hIGF chimeric antibody, anti-hIGF CDR-grafted antibody or an antibody fragment thereof which will be described later, or of all of purified antibodies.

ELISA

An antigen is immobilized on a 96 well ELISA plate and allowed to react with a culture supernatant of a hybridoma or a purified antibody as a primary antibody.

After the reaction with the primary antibody, the plate is washed and a secondary antibody is added thereto. As the secondary antibody, an antibody capable of recognizing the primary antibody and labeled with biotin, an enzyme, a chemiluminescence substance, a radioisotope or the like is used. Specifically, an antibody capable of recognizing a mouse antibody is used as the secondary antibody when mouse was used in preparing hybridoma, or an antibody capable of recognizing a rat antibody is used as the secondary antibody when rat was used in preparing hybridoma.

After the reaction, a reaction is carried out in response to the labeling agent of the secondary antibody, and a sample which specifically reacts with the antigen is selected as a monoclonal antibody producing hybridoma.

Hybridoma KM1468 and the like can be cited as specific examples of said hybridoma. The hybridoma KM1468 was deposited on Mar. 26, 2002, as FERM BP-7978 in International Patent Organism Depositary, National Institute of Advanced Industrial Science and Technology (postal code 305-8566; Central 6, 1-1-1 Higashi, Tsukuba, Ibaraki, Japan).

(6) Purification of Monoclonal Antibody

The anti-hIGF monoclonal antibody producing hybridoma cells obtained in 1(4) are intraperitoneally injected into 8 to 10-week-old mice or nude mice which are treated with pristane (2,6,10,14-tetramethylpentadecane) by its intraperitoneal administration and reared for 2 weeks, at a dose of $5 \times 10^6$ to $2 \times 10^7$ cells per animal. The hybridoma becomes ascites tumor in 10 to 21 days. The ascitic fluid is collected from the mice or the nude mice and centrifuged, and then an IgG or IgM fraction is recovered by salting out with 40 to 50% saturated ammonium sulfate or caprylic acid precipitation method, or using a DEAE-Sepharose column, a protein A column, a Cellulofine GSL 2000 (Seikagaku Corp.) column or the like to give a purified monoclonal antibody.

Determination of the subclass of the purified monoclonal antibody can be carried out using a mouse monoclonal antibody typing kit, a rat monoclonal antibody typing kit or the like. The protein concentration can be calculated by the Lowry method or from the absorbance at 280 nm.

The antibody subclass is an isotype within a class, and IgG1, IgG2a, IgG2b and IgG3 can be cited in the case of mouse, and IgG1, IgG2, IgG3 and IgG4 in the case of human.

(7) Activity Evaluation of Monoclonal Antibody

Binding activity of a culture supernatant or purified anti-hIGF monoclonal antibody to hIGF can be measured by the binding ELISA described above 1(5), competitive ELISA, biosensor BIACORE and the like.

The binding ELISA is a method in which binding activity of an antigen and an antibody is measured by immobilizing an antigen on a 96 well ELISA plate, allowing it to react with a primary antibody, allowing a labeled secondary antibody capable of recognizing the primary antibody to react therewith, and then detecting the label. Examples of the antigen to be immobilized include, purified proteins of hIGF-I and hIGF-II, peptides having partial sequences thereof and the like. Examples of the primary antibody include substances to be measured such as hybridoma culture supernatants, and purified antibodies. Examples of the secondary antibody include antibodies which can recognize the primary antibody and are labeled with biotin, an enzyme, a chemiluminescence substance, a radioisotope or the like. Specifically, a horseradish peroxidase-labeled anti-rat immunoglobulin (hereinafter referred to as rIg) mouse antibody and the like can be exemplified.

The competitive ELISA is a method in which hIGF-I or hIGF-II is immobilized in advance on the ELISA plate, an antibody as the substance to be measured and hIGF-I or hIGF-II are simultaneously added thereto and allowed to react, and the reactivity of another or the same antigen added to the reaction solution to inhibit the reaction of the antigen immobilized on the plate with the antibody to be measured is measured based on the changes in the amount of the primary antibody binding to the plate. Changes in the binding amount of the antibody are detected by the secondary antibody to the antibody. Also, reactivity with a natural type hIGF and antigen epitope can be analyzed by the competitive ELISA using the natural type hIGF and a partial peptide of the hIGF. Whether or not the antibody is recognizing three-dimensional structure of the hIGF can be examined by a conventional structural analysis. As the structural analysis, x-ray crystallographic analysis, magnetic nuclear resonance analysis and the like can, for example, be exemplified.

According to the measurement with a biosensor BIACORE, a very small quantity of change in mass generated on the surface of a sensor tip accompanied by the association and dissociation between two molecules is detected as SPR signal by an optical phenomenon. From the association constant (hereinafter referred to as Kass) and dissociation constant (hereinafter referred to as Kdiss) obtained from the measurement by this method, a binding constant (hereinafter referred to as $K_A$) of $K_A$=Kass/Kdiss is calculated. $K_A$ is expressed by a unit of $M^{-1}$. The measurement with a biosensor BIOCORE can be carried out under optimum measuring conditions in accordance with the instructions attached thereto. Regarding the optimum measuring conditions, it is desirable that amount of the ligand to be immobilized on the sensor tip is within the range between the minimum value calculated by formula 1 and the maximum value calculated by formula 2. Also, it is desirable that binding amount of the analyte is equal to or smaller than the maximum binding amount calculated by formula 3. In formulae 1, 2 and 3, ligand means a molecule to be immobilized on the sensor tip, analyte means a molecule to be added via a channel system, and S means the number of ligand binding site. RU is abbreviation of resonance unit which indicates changed amount of mass per unit area on the sensor tip surface, wherein 1 RU=1 pg/mm². According to the measurement with a biosensor BIACORE, analysis of the binding constant based on the binding mode of each protein can be carried out by setting flow rate and washing condition such that the maximum binding amount can be maintained.

Minimum immobilized amount $(RU)$=200×1/S×(molecular weight of ligand/molecular weight of analyte)        Formula 1

Maximum immobilized amount $(RU)$=1000×1/S× (molecular weight of ligand/molecular weight of analyte)        Formula 2

Maximum binding amount=molecular weight of analyte×immobilized amount of ligand $(RU)$/molecular weight of ligand×S        Formula 3

In addition, the activity of the antibody of the present invention to inhibit functions of hIGF can be measured by examining influence of the antibody upon in Vivo or in vitro growth of a cell strain showing hIGF-dependent growth.

The influence upon the growth of a cell strain showing hIGF-dependent growth means influence of the antibody of the present invention or an antibody fragment thereof upon Anvil cell growth of a cell strain showing hIGF-dependent growth, in the presence of hIGF, or upon in vivo cell growth of a cell strain showing hIGF-dependent growth, which is transplanted into an animal such as mouse.

As the in vitro cell growth of a cell strain showing hIGF-dependent growth in the presence of hIGF, cell growth when a cell is cultured using a medium prepared by adding hIGF to an hIGF-free basal medium or the like can be examplified. As the hIGF-free basal medium, TF/BSA medium [a medium prepared by adding 10 µg/ml of human transferrin (manufactured by Gibco BRL) and 200 µg/ml of BSA to D-MEM/F-12 (manufactured by Gibco BRL)] and the like can be exemplified. Regarding the method for measuring cell growth, it can be measured using a cell growth reagent WST-1 (manufactured by Roche).

Regarding the in vivo cell growth of a cell strain showing hIGF-dependent growth, growth of a cell in the animal body when the cell is transplanted into an animal such as mouse can be exemplified. Regarding the method for measuring cell growth, for example, when the cell is developed in the body of a mouse as a tumor mass, it is possible to measure volume of the tumor mass and use the value as an index of the cell growth.

As the cell strain showing hIGF-dependent growth, a human breast cancer cell line MCF7 (ATCC HTB-22), a human colon cancer cell line HT-29 (ATCC HTB-38), a human osteosarcoma cell line MG63 (ATCC CRL-1427) and the like can be exemplified. In addition, a transformant introduced with an hIGF-I gene can also be exemplified.

Examples of the transformant introduced with an hIGF-I gene include a cell strain into which a cloned hIGF-I gene is introduced so that expressed amount of hIGF-I is increased in comparison with the case of not introducing the hIGF-I gene. Specific examples include a transformant which is prepared by introducing the hIGF-I gene into a human lung cancer cell strain A549 cell (ATCC CCL-185). Regarding the hIGF-I gene, the sequence described in a reference (*Molecular Endocrinology*, 4, 1914-1920, 1990) can be cloned by a method such as PCR.

2. Preparation of Humanized Antibody (1) Construction of Vector for Expression of Humanized Antibody As the vector for expression of humanized antibody, it may be any expression vector for animal cell use into which a gene coding for CH and/or CL of a human antibody is integrated. The vector for expression of humanized antibody can be constructed by respectively cloning genes coding for CH and CL of a human antibody into expression vector for animal cell use.

The C region of a human antibody can be CH and CL of an optional human antibody, and its examples include a C region of IgG1 subclass of human antibody H chain (hereinafter referred to as hCγ1), a C region of κ class of human antibody L chain (hereinafter referred to as hCκ) and the like. As the genes coding for CH and CL of a human antibody, a chromosomal DNA comprising exons and introns can be used, and cDNAs can also be used.

As the expression vector for animal cell use, any vector can be used with the proviso that it can integrate and express a gene coding for the C region of a human antibody. For example, pAGE107 (*Cytotechnology*, 3, 133-140, 1990), pAGE103 (*Journal of Biochemistry*, 101, 1307-1310, 1987), pHSG274 (*Gene*, 27, 223-232, 1984), pKCR (*Proceedings of the National Academy of Sciences of the Untied States of America*, 78, 1527-1531, 1981), pSG1βd2-4 (*Cytotechnology*, 4, 173-180, 1990) and the like can be exemplified. As the promoter and enhancer to be used in the expression vector for animal cell use, SV40 early promoter and enhancer (*Journal of Biochemistry*, 101, 1307-1310, 1987), LTR promoter and enhancer of Moloney mouse leukemia virus (*Biochemical & Biophysical Research Communications*, 149, 960-968, 1987), promoter (*Cell*, 41, 479-487, 1985) and enhancer (*Cell*, 33, 717-728, 1983) of immunoglobulin H chain and the like can be exemplified.

As the vector for expression of humanized antibody, either of a type in which the antibody H chain and L chain are present in different vectors or a type in which they are present in the same vector (hereinafter referred to as tandem-type) can be used, a tandem-type vector for expression of humanized antibody is preferable in view of easiness for construction a humanized antibody expression vector, easiness for introducion into animal cells and easiness for equality of the amount of the expressed antibody H chain and L chain in an animal (*Journal of Immunological Methods*, 167, 271-278, 1994). Examples of the tandem-type vector for expression of humanized antibody include pKANTEX93 (WO 97/10354), pEE18 (*Hybridoma*, 17, 559-567, 1998) and the like.

The constructed vector for expression of humanized antibody can be used for the expression of human chimeric antibodies and human CDR-grafted antibodies in animal cells.

(2) Preparation of cDNAs Coding for Antibody V Region of a Non-Human Animal and Analysis of Amino Acid Sequence cDNAs coding for VH and VL of an antibody of a non-human animal, such as a mouse antibody, for example, are obtained in the following manner.

mRNA is extracted from a hybridoma which produces a mouse antibody or the like, and then cDNAs are synthsized. The synthesized cDNAs are cloned into a vector such as a phage, plasmid or the like to prepare a cDNA library. A recombinant phage or recombinant plasmid having a cDNA coding for VH or a recombinant phage or recombinant plasmid having a cDNA coding for VL are respectively isolated from said library using a C region moiety or V region moiety of a mouse antibody as a probe. The full length nucleotide sequences for the intended VH and VL of the mouse antibody on the recombinant phage or recombinant plasmid is determined, and the full length amino acid sequences of VH and VL are deduced from the nucleotide sequence.

As a non-human animal, any of animals capable of producing a hybridoma, such as mouse, rat, hamster, rabbit and the like.

A guanidine thiocyanate-cesium trifluoroacetate method (*Method in Enzymology*, 154, 3-28, 1987) can be exemplified as the method for preparing total RNA from a hybridoma, and an oligo(dT) immobilized cellulose column method (Molecular Cloning: A Laboratory Manual, Cold Spring Harbor Lab. Press New York, 1989) as the method for preparing mRNA from total RNA. Also, as the kit for preparing mRNA from a hybridoma, Fast Track mRNA Isolation Kit (manufactured by Invitrogen), Quick Prep mRNA Purification Kit (manufactured by Amersham Pharmacia) and the like can be exemplified.

Examples of the methods for synthesizing cDNA and preparing a cDNA library include conventional methods (Molecular Cloning: A Laboratory Manual, Cold Spring Harbor Lab. Press New York, 1989; Current Protocols in Molecular Biology, Supplement 1-34), or methods using commercially available kits such as Super Script™ Plasmid System for cDNA Synthesis and Plasmid Cloning (manufactured by GIBCO BRL), ZAP-cDNA Synthesis Kit (manufactured by Stratagene) and TimeSaver cDNA Synthesis Kit (manufactured by Amersham-Pharmacia).

In preparing a cDNA library, as the vector to be used for the integration of cDNA synthesized using mRNA extracted from a hybridoma as the template, any vector capable of integrating said cDNA can be used. The examples include phage and plasmid such as ZAP Express (*Strategies*, 5, 58-61, 1992), pBluescript II SK(+) (*Nucleic Acid Research*, 17, 9494, 1989), λZAP II (manufactured by Stratagene), λgt10 and λgt11 (DNA Cloning: A practical Approach, 1, 49, 1985), Lambda BlueMid (manufactured by Clontech), % λExCell and pT7T318U (manufactured by Amersham-Pharmacia), pcD2 (*Molecular & Cellular Biology*, 3, 280-289, 1983) and pUC18 (*Gene*, 33, 103-119, 1985).

As the *Escherichia coli* into which a cDNA library constructed by a phage or plasmid vector is introduced, any strain can be used with the proviso that said cDNA library can be introduced, expressed and maintained. The examples include XL1-Blue MRF' (*Journal of Biotechnology*, 23, 271-289, 1992), C600 (*Genetics*, 59, 177-190, 1968), Y1088 and Y1090 (*Science*, 222, 778-782, 1983), NM522 (*Journal of Molecular Biology*, 166, 1-19, 1983), K802 (*Journal of Molecular Biology*, 16, 118-133, 1966) and JM105 (*Gene*, 38, 275-276, 1985).

As the method for selecting a cDNA clone coding for VH and VL of an antibody of a non-human animal from a cDNA library, it can be selected by a colony hybridization method or plaque hybridization method (Molecular Cloning: A Laboratory Manual, Cold Spring Harbor Lab. Press New York, 1989) which uses probe labeled with a radioisotope, a fluorescent substance or an enzyme. In addition, a cDNA coding for VH and VL can also be prepared by carrying out the polymerase chain reaction (hereinafter referred to as PCR method; Molecular Cloning: A Laboratory Manual, Cold Spring Harbor Lab. Press New York, 1989; Current Protocols in Molecular Biology, Supplement 1-34) by preparing primers and using a cDNA synthesized from mRNA, or a cDNA library, as the template.

Nucleotide sequence of said cDNA can be determined by digesting the cDNA selected by the above method with appropriate restriction enzymes, cloning the digests into a plasmid vector such as pBluescript SK(−) (manufactured by Stratagene), and then carrying out a reaction such as a conventionally used nucleotide sequence analyzing method, for example, the dideoxy method (*Proceedings of the National Academy of Sciences of the Untied States of America*, 74, 5463-5467, 1977) and analyzing the results using an automatic nucleotide sequence analyzer such as an automatic nucleotide sequence analyzer ABI PRISM 377 (manufactured by Applied Biosystems) or the like.

By deducing full length amino acid sequence of VH and VL from the determined nucleotide sequence and comparing the result with full length amino acid sequences of VH and VL of known antibodies (Sequences of Proteins of Immunological Interest, US Dept. Health and Human Services, 1991), whether or not the thus obtained cDNA encodes full length amino acid sequence of VH and VL of the antibody containing secretion signal sequence can be verified. Regarding the full length amino acid sequence of VH and VL of the antibody containing secretion signal sequence, length of the secretion signal sequence and the N terminal sequence can be deduced and subgroups to which they belong can be alarified by comparison with full length amino acid sequences of VH and VL of known antibodies (Sequences of Proteins of Immunological Interest, US Dept. Health and Human Services, 1991). In addition, amino acid sequence of each CDRs of VH and VL can also be found by comparing with amino acid sequences of VH and VL of known antibodies (Sequences of Proteins of Immunological Interest, US Dept. Health and Human Services, 1991).

Also, novelty of the sequences can be examined by carrying out sequence homology retrieval such as BLAST method (Journal of Molecular Biology, 215, 403-410, 1990) on an optional data base, for example, SWISS-PROT, PIR-Protein or the like, using the full length amino acid sequence of VH and VL.

(3) Construction of Human Chimeric Antibody Expression Vector

A human chimeric antibody expression vector can be constructed by cloning cDNAs coding for VH and VL of an antibody of a non-human animal into upstream of the gene coding for CH and CL of a human antibody in the vector for expression of humanized antibody described in the above 2(1). For example, a human chimeric antibody expression vector can be constructed by respectively ligating cDNAs coding for VH and VL of an antibody of a non-human animal to a synthetic DNA which comprises 3′-terminal side nucleotide sequences of VH and VL of an antibody of a non-human animal and 5′-terminal side nucleotide sequences of CH and CL of a human antibody and also has appropriate restriction enzyme recognizing sequences on both termini, and by respectively cloning them into upstream of the gene coding for CH and CL of a human antibody in the vector for expression of humanized antibody described in the above 2(1) in such a manner that they are expressed in appropriate forms. In addition, a human chimeric antibody expression vector can be constructed by amplifying cDNAs coding for VH and VL of an antibody of a non-human animal by PCR method using plasmids containing cDNAs coding for the VH and VL as templates and using primers having appropriate restriction enzyme recognizing sequences on 5′-termini, and respectively cloning them into upstream of the gene coding for CH and CL of a human antibody in the vector for expression of humanized antibody described in the above 2(1) in such a manner that they are expressed in suatable forms.

(4) Construction of cDNAs Coding for V Region of a Human CDR-Grafted Antibody cDNAs coding for VH and VL of a human CDR-grafted antibody can be constructed in the following manner. Firstly, FR amino acid sequences of VH and VL of a human antibody are selected for grafting the intended CDR amino acid sequences of VH and VL of an antibody of a non-human. As the FR amino acid sequences of VH and VL of a human antibody, any sequences can be used with the proviso that they are derived from a human antibody. The examples include the FR amino acid sequences of VH and VL of human antibodies registered in data bases such as Protein Data Bank and consensus amino acid sequences of FR VH and VL of subgroups of human antibodies (Sequences of Proteins of Immunological Interest, US Dept. Health and Human Services, 1991) and the like, but for the purpose of preparing a human CDR-grafted antibody having sufficient activity, it is desirable to select amino acid sequences having a homology of as high as possible (at least 60% or more) with the intended FR amino acid sequences of VH and VL of an antibody of a non-human animal. Next, amino acid sequences of VH and VL of a human CDR-grafted antibody are designed by grafting the intended CDR amino acid sequences of VH and VL of an antibody of a non-human animal to the thus selected FR amino acid sequences of VH and VL of a human antibody. The designed amino acid sequences are converted into nucleotide sequences in consideration of the codon frequency found in nucleotide sequences of antibody genes (Sequences of Proteins of Immunological Interest, US Dept. Health and Human Services, 1991). Based on the nucleotide sequences thus designed, several synthetic DNA fragments having a length of about 100 bases are synthesized, and PCR is carried out using them. In this case, it is prefarable to design six synthesized DNAs for each of VH and VL in view of the PCR efficiency and the length of DNA to be synthesized.

In addition, DNAs can be easily cloned into the vector for expression of humanized antibody constructed in the above 2(1) by introducing appropriate restriction enzyme recognizing sequences into both 5′ termini of the synthetic DNA. After the PCR, the amplified products are cloned into plasmids such as pBluescript SK(−) (manufactured by Stratagene) and their nucleotide sequences are determined by the method described in the above 2(2) to obtain plasmids having nucleotide sequences coding for the intended amino acid sequences of VH and VL of the human CDR-grafted antibody.

(5) Modification of V Region Amino Acid Sequences of Human CDR-Grafted Antibody

It is known that antigen binding activity of a human CDR-grafted antibody is reduced in comparison with the case of the original antibody of a non-human animal, when only the desired CDRs of VH and VL of an antibody of a non-human animal are grafted to the FRs of VH and VL of a human antibody (*BIO/TECHNOLOGY*, 9, 266-271, 1991). As the cause of this, it is considered that some amino acid residues of not only CDRs but also FRs are involved in the antigen binding activity directly or indirectly in the VH of VL of the original antibody of a non-human animal, concerned in the antigen binding activity, and these amino acid residues are considered to be changed to another amino acid residues of the FRs of VH and VL of human antibody according to the grafting of CDRs. With the aim of solving this problem, in the case of a human CDR-grafted antibody, an attempt has been made to identify certain amino acid residues in the amino acid sequences of FRs of VH and VL of the human antibody, which are directly concerned in the binding with the antigen or which are indirectly concerned in the binding with the antigen by interacting with amino acid residue of CDR or maintaining three-dimensional structure of the antibody, and to increase the once reduced antigen binding activity by modifying them into the amino acid residues which are found in the original antibody of a non-human animal (*BIO/TECH-NOLOGY*, 9, 266-271, 1991). In preparing a human CDR-grafted antibody, it is the most important point to efficiently identify such FR amino acid residues concerned in the antigen binding activity, and construction and analysis of the three-dimensional structure of antibodies by an X-ray crystallographic analysis (*Journal of Molecular Biology*, 112, 535-542, 1977), a computer modeling (*Protein Engineering*, 7, 1501-1507, 1994) or the like have been carried out for this purpose. Information of the three-dimensional structure of these antibodies have produced many useful information for the preparation of human CDR-grafted antibodies, but on the other hand, a method for preparing a human CDR-grafted antibody which is applicable to every antibody has not been established yet, and it is necessary at present to carry out various try and error efforts, for example by preparing several modified bodies from each antibody and examining their correlation to respective antigen binding activities.

Modification of FR amino acid residues of VH and VL of a human antibody can be achieved by carrying out the PCR method described in the above 2(4) using a synthetic DNAs for mutagenesis. Nucleotide sequence of the amplified product by PCR is determined by the method described in the above 2(2) to confirm that the desired modification was attained.

(6) Construction of Human CDR-Grafted Antibody Expression Vector

A human CDR-grafted antibody expression vector can be constructed by cloning cDNAs coding for the VH and VL of human CDR-grafted antibody constructed in the above 2(4) and (5) into upstream of the genes coding for human antibody CH and CL contained in the vector for expression of humanized antibody described in the above 2(1).

For example, by introducing appropriate restriction enzyme recognizing sequences into both 5' termini of the synthetic DNA which is used for constructing the VH and VL of a human CDR-grafted antibody in the above 2(4) and (5), they can be cloned into upstream of the genes coding for CH and CL of a human antibody contained in the vector for expression of humanized antibody described in the above 2(1) in such a manner that they are expressed in suitable forms.

(7) Transient Expression of Humanized Antibody

In order to efficiently evaluate the antigen binding activity of many types of the prepared humanized antibodies, transient expression of the humanized antibodies can be carried out using the humanized antibody expression vectors described in the above 2(3) and (6) or using expression vectors mutated. As the host cell into which the expression vector is introduced, any cell can be used with the proviso that it is a host cell which can express the humanized antibody, and a monkey kidney-derived cell strain COS-7 cell (ATCC CRL 1651) is generally used (Methods in Nucleic Acids Research, CRC Press, 283, 1991) in consideration of its large amount of expression. Examples of the method for introducing expression vector into COS-7 cell include the DEAE-dextran method (Methods in Nucleic Acids Research, CRC Press, 283, 1991), the lipofection method (*Proceedings of the National Academy of Sciences of the United States of America*, 84, 7413-7417, 1987) and the like.

After introduction of the expression vector, amount of expression and antigen binding activity of the humanized antibody in the culture supernatant can be measured by ELISA (Antibodies: A Laboratory Manual, Cold Spring Harbor Laboratory, Chapter 14, 1988; Monoclonal Antibodies: Principles and Practice, Academic Press Limited, 1996) and the like.

(8) Stable Expression of Humanized Antibody

A transformant capable of stably expressing a humanized antibody can be obtained by introducing the humanized antibody expression vector described in the above 2(3) or (6) into an appropriate host cell.

As the method for introducing the expression vector into a host cell, the electroporation method (*Cytotechnology*, 3, 133-140, 1990) and the like can be exemplified.

As the host cell into which the humanized antibody expression vector is introduced, any cell can be used with the proviso, that it is a host cell which can express the humanized antibody, and the examples include mouse SP2/0-Ag14 cell (ATCC CRL 1581), mouse P3X63-Ag8.653 cell (ATCC CRL 1580), a dihydrofolate reductase gene (hereinafter referred to as dhfr)-deficient CHO cell (*Proceedings of the National Academy of Sciences of the United States of America*, 77, 4216-4220, 1980), rat YB2/3HL.P2.G11.16Ag.20 cell (ATCC CRL 1662, hereinafter referred to as YB2/0 cell) and the like.

After introduction of the expression vector, the obtained transformant is cultured using a medium for animal cell containing drugs such as G418 sulfate (hereinafter referred to as G418) in accordance with the method disclosed in Japanese published unexamined application No. 257891/90, and a transformant which stably expresses the humanized antibody can be selected. Examples of the medium for animal cell includes RPMI 1640 medium (manufactured by Nissui Pharmaceutical), GIT medium (manufactured by Nihon Seiyaku), EX-CELL 302 medium (manufactured by JRH), IMDM (manufactured by GIBCO BRL) and Hybridoma-SFM (manufactured by GIBCO BRL), or media prepared by adding various additives such as FCS to these media. The obtained transformant is cultured in a medium, and the humanized antibody can be expressed and accumulated in a culture supernatant. The amount of expression and antigen binding activity of the humanized antibody in the culture supernatant can be measured by ELISA. In addition, amount of expression of the humanized antibody by the transformant can be increased by utilizing of a dhfr amplification system or the like in accordance with the method disclosed in Japanese published unexamined application No. 257891/90.

The humanized antibody can be purified from the culture supernatant of transformant cell using a protein A column (Antibodies: A Laboratory Manual, Cold Spring Harbor Laboratory, Chapter 8, 1988; Monoclonal Antibodies: Principles and Practice, Academic Press Limited, 1996). In addition, purification methods generally used for the purification of protein can also be used. For example, the purification can be carried out by employing a combination of gel filtration, ion exchange chromatography, ultrafiltration and the like. Molecular weight of the H chain, L chain or the whole antibody molecule of the purified humanized antibody can be measured by polyacrylamide gel electrophoresis (hereinafter referred to as PAGE: Nature, 227, 680-685, 1970), western blotting method (Antibodies: A Laboratory Manual, Cold Spring Harbor Laboratory, Chapter 12, 1988; Monoclonal Antibodies: Principles and Practice, Academic Press Limited, 1996) and the like.

(9) Activity Evaluation of Humanized Antibody

Binding activity of anti-IGF humanized antibody in a culture supernatant or purified anti-hIGF humanized antibody to hIGF can be measured by the ELISA, biosensor BIACORE or the like shown in the above 1(7). In addition, the activity of the antibody of the present invention to inhibit functions of hIGF can be measured by examining influence of the antibody upon in Vivo or in vitro growth of cell strains showing hIGF-dependent growth, as shown in the above 1(7).

3. Preparation of Antibody Fragments

The antibody fragments can be prepared from the anti-hIGF antibodies described in the above 1 and 2. by genetic engineering techniques or protein chemistry techniques based.

As the genetic engineering techniques, mentioned are a method in which a gene coding for the antibody fragment of interest is constructed, and expression and purification is carried out using an appropriate host such as an animal cell, plant cell, insect cell, and Escherichia coli.

As the protein chemistry techniques, mentioned are methods including site-specific digestion using protease such as pepsin and papain and purification.

As the antibody fragments, Fab, F(ab')$_2$, Fab' scFv, diabody, dsFv, a CDR-containing peptide and the like can be exemplified.

(1) Preparation of Fab

According to a protein chemistry techniques, Fab can be prepared by treating IgG with a protease papain. After the papain treatment, when the original antibody is an IgG subclass having protein A binding ability, uniform Fab can be recovered by separating it from IgG molecules and Fc fragments by passing through a protein A column (Monoclonal Antibodies: Principles and Practice, third edition, 1995). In the case of an antibody of IgG subclass having no protein A binding ability, Fab can be recovered by an ion exchange chromatography in a fraction eluted with a low salt concentration (Monoclonal Antibodies: Principles and Practice, third edition, 1995). In addition, Fab can also be prepared by genetic engineering techniques using Escherichia coli in most cases or using an insect cell, animal cell or the like. For example, an Fab expression vector can be prepared by cloning the DNA coding for antibody V region obtained in the above 2(2), 2(4) or 2(5) into a vector for expression of Fab. As the vector for expression of Fab, any vector can be used with the proviso that it can effect intergration and expression of a DNA of Fab. For example, pIT106 (Science, 240, 1041-1043, 1988) and the like can be examplified. Fab can be produced and accumulated in an inclusion body or periplasmic space by introducing the Fab expression vector into an appropriate Escherichia coli. Active Fab can be obtained from the inclusion body by a refolding method commonly used for protein, and when it is expressed in the periplasmic space, active Fab is leaked in the culture supernatant. Uniform Fab can be purified after the refolding or from the culture supernatant using a column immobilized with an antigen (Antibody Engineering, A Practical Guide, W.H. Freeman and Company, 1992).

(2) Preparation of F(ab')$_2$

According to a protein chemistry techniques, F (ab')$_2$ can be prepared by treating IgG with a protease pepsin. After the pepsin treatment, it can be recovered as uniform F(ab')$_2$ by carrying out a purification procedure similar to the case of Fab (Monoclonal Antibodies: Principles and Practice, third edition, Academic Press, 1995). In addition, F(ab')$_2$ can also be prepared by the method described in the following 3(3) in which Fab' is treated with maleimide such as o-PDM and bismaleimide hexane to effect thioether bonding, or a method in which it is treated with DTNB [5,5'-dithiobis (2-nitrobenzoic acid)] to effect S—S bonding (Antibody Engineering, A Practical Approach, IRL PRESS, 1996).

(3) Preparation of Fab'

Fab' can be obtained by treating the F(ab')$_2$ described in above 3(2) with a reducing agent such as dithiothreitol. Also, Fab' can be prepared by genetic engineering techniques using Escherichia coli in most cases or using an insect cell, animal cell or the like. For example, an Fab' expression vector can be prepared by cloning the DNA coding for antibody V region obtained in the above 2(2), 2(4) or 2(5) into a vector for expression of Fab'. As the vector for expression of Fab', any vector can be used with the proviso that it can effect intergration and expression of a DNA for Fab' use. For example, pAK19 (BIO/TECHNOLOGY, 10, 163-167, 1992) and the like can be examplified. Fab' can be produced and accumulated in an inclusion body or periplasmic space by introducing the Fab' expression vector into an appropriate Escherichia coli. Active Fab' can be obtained from the inclusion body by a refolding method commonly used for protein, and when it is expressed in the periplasmic space, it can be recovered into extracellulary by disrupting the cells by a treatment such as lysozyme partial digestion, osmotic shock and ultra sonication. Uniform Fab' can be purified after the refolding or from the disrupted cell suspension using a protein G column or the like (Antibody Engineering, A Practical Approach, IRL PRESS, 1996).

(4) Preparation of scFv

According to genetic engineering techniques, scFv can be prepared using a phage or Escherichia coli, or an insect cell, animal cell or the like. For example, an scFv expression vector can be prepared by cloning DNAs coding for the V region of the antibody described in the above 2(2), 2(4) or 2(5) into a vector for expression of scFv. As the vector for expression of scFv, any vector can be used with the proviso that it can effect intergration and expression of a DNA of scFv. For example, pCANTAB5E (manufactured by Amersham-Pharmacia), pHFA (Human Antibodies & Hybridomas, 5, 48-56, 1994) and the like can be examplified. By introducing the scFv expression vector into an appropriate Escherichia coli and infecting the cells with a helper phage, a phage which expresses scFv on the phage surface in a fused form with the phage surface protein can be obtained. Also, scFv can be produced and accumulated in the inclusion body or periplasmic space of scFv expression vector-introduced Escherichia coli. Active scFv can be obtained from the inclusion body by a refolding method commonly used for protein, and when it is expressed in the periplasmic space, it can be recovered into extracellulary by disrupting the cells by a treatment such as lysozyme partial digestion, osmotic shock and ultra sonication. Uniform scFv can be purified after the refolding or from the disrupted cell suspension using a cation exchange chromatography or the like (Antibody Engineering, A Practical Approach, IRL PRESS, 1996).

(5) Preparation of Diabody

By genetic engineering techniques, diabody can be prepared using Escherichia coli in most cases or using an insect cell, animal cell or the like. For example, a diabody expression vector can be prepared by preparing DNAs coding for the VH and VL of the antibody described in the above 2(2), 2(4)

or 2(5) are linked to each other in such a manner that the number of amino acid residues encoded by the linker becomes 8 residues or less, and cloning it into a vector for expression of diabody. As the vector for expression of diabody, any vector can be used with the proviso that it can effect intergration and expression of a DNA of diabody. For example, pCANTAB5E (manufactured. by Amersham-Pharmacia), pHFA (*Human Antibodies Hybridomas*, 5, 48, 1994) and the like can be exemplified. Diabody can be produced and accumulated in the inclusion body or periplasmic space of diabody expression vector-introduced *Escherichia coli*. Active diabody can be obtained from the inclusion body by a refolding method commonly used for protein, and when it is expressed in the periplasmic space, it can be recovered into extracellulary by disrupting the cells by a treatment such as lysozyme partial digestion, osmotic shock and ultra sonication. Uniform scFv can be purified after the refolding or from the disrupted cell suspension using a cation exchange chromatography or the like (Antibody Engineering, A Practical Approach, IRL PRESS, 1996).

(6) Preparation of dsFv

According to genetic engineering techniques, dsFv can be prepared using *Escherichia coli* in most cases, or using an insect cell, animal cell or the like. Firstly, DNAs in which an encoded amino acid residue is replaced by cysteine are prepared by introducing mutation into appropriate positions of the DNAs coding for antibody VH and VL described in the above 2(2), 2(4) or 2(5). VH and VL expression vectors can be prepared by cloning each of the DNA thus prepared into a vector for expression of dsFv. AS the vector for expression of dsFv, any vector can be used with the proviso that it can effect intergration and expression of a DNA of dsFv. For example, pULI9 (*Protein Engineering*, 7, 697-704, 1994) and the like can be exemplified. By introducing the VH and VL expression vectors into an appropriate *Escherichia coli*, they can be produced and accumulated in the inclusion body or periplasmic space. By obtaining the VH and VL from the inclusion body or periplasmic space and mixing them, active dsFv can be obtained by a refolding method commonly used for protein. After the refolding, it can be further purified by an ion exchange chromatography, gel filtration and the like (*Protein Engineering*, 7, 697-704, 1994).

(7) Preparation of CDR Peptide

A peptide containing CDR can be prepared by chemical synthesis method such as Fmoc method and tBoc method. A CDR peptide expression vector can be prepared by preparing a DNA coding for a CDR-containing peptide, and cloning the DNA thus prepared into an appropriate vector for expression. As the vector for expression, any vector can be used with the proviso that it can effect integration and expression of a DNA coding for CDR-containing peptide. For example, pLEX (manufactured by Invitrogen), pAX4a+ (manufactured by Invitrogen) and the like can be exemplified. By introducing the expression vector into an appropriate *Escherichia coli*, the peptide can be produced and accumulated in the inclusion body or periplasmic space. By obtaining the CDR peptide from the inclusion body or periplasmic space, it can be purified by an ion exchange chromatography, gel filtration and the like (*Protein Engineering*, 7, 697-704, 1994).

(8) Activity Evaluation of Antibody Fragments

Binding activity of the purified antibody fragments to hIGF can be measured by the ELISA, biosensor BIACORE and the like shown in the above 1(7). In addition, the activity of the antibody of the invention to inhibit functions of hIGF can be measured by examining influence of the antibody upon in vivo or in vitro growth of the cell strains showing hIGF-dependent growth, as shown in the above 1(7).

4. Methods for Detecting and Determining hIGF Using Anti-hIGF Antibody

The present invention relates to methods for immunologically detecting and determining hIGF using the antibody of the present invention. Accordingly, the antibody of the present invention can be used for the diagnosis of hIGF-mediated diseases and diseases showing pathological progressing due to abnormally accelerated hIGF production, which will be described later.

Regarding the method for immunologically detecting or determining hIGF using the antibody of the present invention, fluorescent antibody technique, ELISA, radioimmunoassay (hereinafter referred to as RIA), immunohistochemical staining methods such as immune tissue staining method and immunocyte staining method (ABC method, CSA method and the like), sandwich ELISA (Monoclonal Antibody Experimentation Manual, Kodansha Scientific, 1987; Second Series Biochemistry Experimentation Course 5, Immunobiochemistry studies, Tokyo Kagaku Dojin, 1986) and the like can be exemplified.

The fluorescent antibody technique is a method in which the antibody of the present invention is allowed to react with an isolated cell or tissue and further allowed to react with an anti-Ig antibody or antibody fragment labeled with a fluorescent substance such as fluorescein isothiocyanate (hereinafter referred to as FITC) and then the fluorescence dye is measured using a flow cytometer.

The RIA is a method in which the antibody of the present invention is allowed to react with a cell or disrupted solution thereof, a tissue or disrupted solution thereof, a cell culture supernatant, serum, pleural effusion, ascites, ophthalmic fluid or the like and further allowed to react with an anti-Ig antibody or antibody fragment treated with a radioisotope labeling and then the isotope is measured using a scintillation counter or the like.

The immunocyte staining method or immune tissue staining method is a method in which the antibody of the present invention is allowed to react with an isolated cell or tissue and further allowed to react with an anti-Ig antibody or antibody fragment treated with a fluorescent material such as FITC and an enzyme label such as peroxidase and biotin and then the sample is observed under a microscope.

The sandwich ELISA is a method in which one of two antibodies of the present invention having different antigen recognizing sites first is immobilized to an ELISA plate, the other antibody is labeled with a fluorescent substance such as FITC or an enzyme such as peroxidase and biotin, the antibody-immobilized plate is allowed to react with an isolated cell or disrupted solution thereof, a tissue or disrupted solution thereof, a cell culture supernatant, serum, pleural effusion, ascites, ophthalmic fluid or the like, and then the labeled antibody is allowed to react therewith and a reaction corresponding to each label is carried out.

5. Diagnosis and Treatment of hIGF-Mediated Diseases and Diseases Showing Pathological Progressing Due to Abnormally Promoted hIGF Production Since the anti-hIGF antibody of the present invention and antibody fragments thereof specifically bind to hIGF-I and hIGF-II and inhibit their functions, it is considered that they are useful for diagnosing and treating hIGF-mediated diseases and diseases showing pathological progressing due to abnormally promoted hIGF production. In addition most part of a humanized antibody is derived from an amino acid sequence of a human antibody in comparison with an antibody of a non-human animal, it does not show immunogenicity in the human body, and its repeated administration is possible and long-term persistency of its effect is expected.

As the method for diagnosing hIGF-mediated diseases and diseases showing pathological progressing due to abnormally promoted hIGF production, the method described in the above 4 in which hIGF existing in a biological sample of a person to be tested such as cell, tissue and serum is immunologically detected can be exemplified.

The anti-hIGF antibody of the present invention or an antibody fragment thereof can be administered as it is, but it is desirable in general to provide it as a pharmaceutical preparation produced by an optional method well known in the technical field of manufacturing pharmacy, by mixing it with one or more pharmacologically acceptable carriers.

As the administration route, it is advisable to use the most effective route in the treatment. Examples thereof can include oral administration and parenteral administrations such as intraoral, intratracheal, intrarectal, subcutaneous, intramuscular, intraarticular and intravenous administrations. In case of the antibody or peptide preparations, intraarticular and intravenous administrations are preferable.

Examples of the administration form include sprays, capsules, tablets, granules, syrups, emulsions, suppositories, injections, ointments, tapes and the like.

Examples of appropriate preparations for oral administration include emulsions, syrups, capsules, tablets, powders, granules and the like.

Liquid preparations such as emulsions and syrups can be produced by using, as additives, water, saccharides such as sucrose, sorbitol and fructose, glycols such as polyethylene glycol and propylene glycol, oils such as sesame oil, olive oil and soybean oil, antiseptics such as p-hydroxybenzoic acid esters, and flavors such as strawberry flavor and peppermint.

Capsules, tablets, powders, granules and the like can be produced by using, as additives, excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid esters, and plasticizers such as glycerin.

Examples of preparations appropriate for parenteral administration include injections, suppositories, sprays and the like.

Injections are prepared by using a carrier comprising a salt solution, a glucose solution or a mixture of both, and the like.

Suppositories are prepared using a carrier such as cacao butter, hydrogenated fat or carboxylic acid.

Sprays are prepared by using the antibody or the peptide as such or in combination with a carrier which facilitates dispersion and absorption of the antibody or the peptide in the form of fine particles without stimulating the mouth and the airway mucous membrane of a recipient.

Specific examples of the carrier include lactose, glycerin and the like. Preparations such as aerosol and dry powder can be formed depending on properties of the antibody or the peptide and the carrier used. These parenteral preparations may comprise the ingredients listed as additives in the oral preparations.

The dose or the number of administrations varies with the desired therapeutic effects, the administration method, the therapeutic period, the age, the body weight and the like. It is usually from 10 μg/kg to 10 mg/kg per day for an adult.

Figure 1:
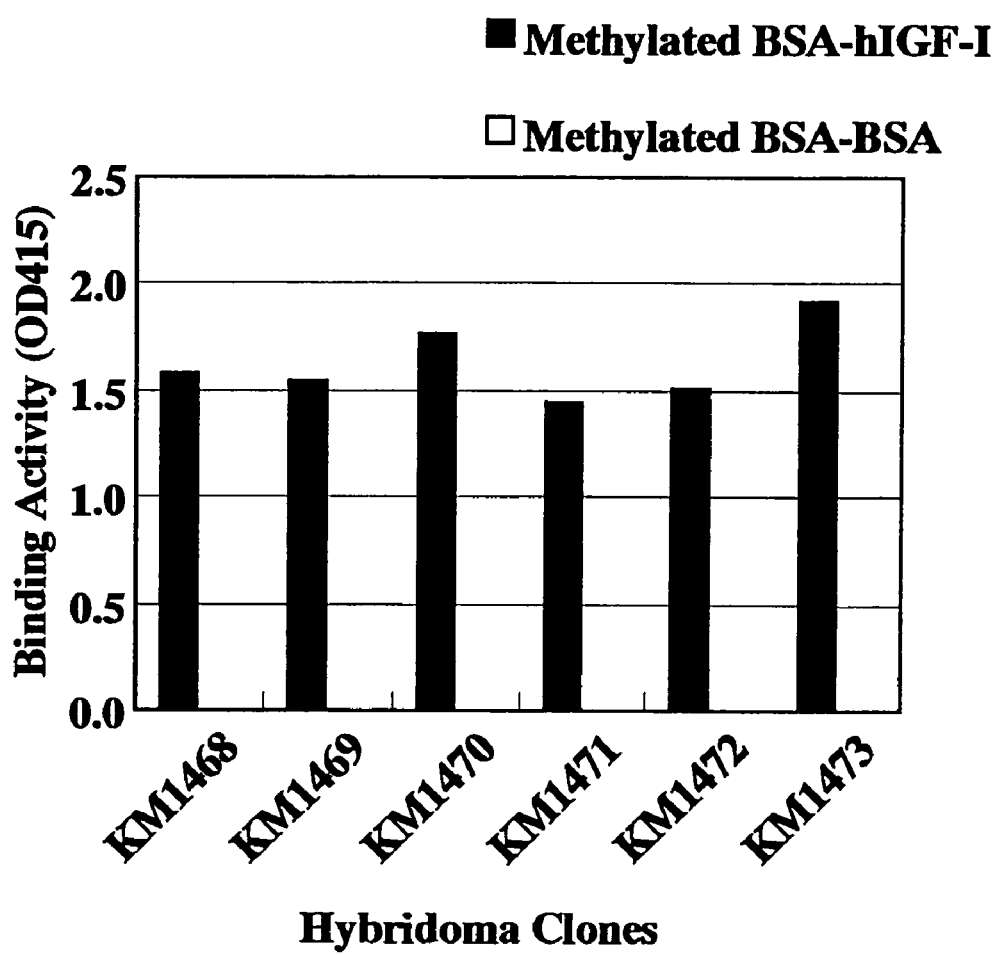
FIG. 1 shows reactivity of anti-hIGF rat monoclonal antibody specific for hIGF-I (binding ELISA).

The abscissa shows concentration of respective peptides (μg/ml), and the ordinate shows binding activity (%). The various peptides used are shown in the drawing.

Figure 4:
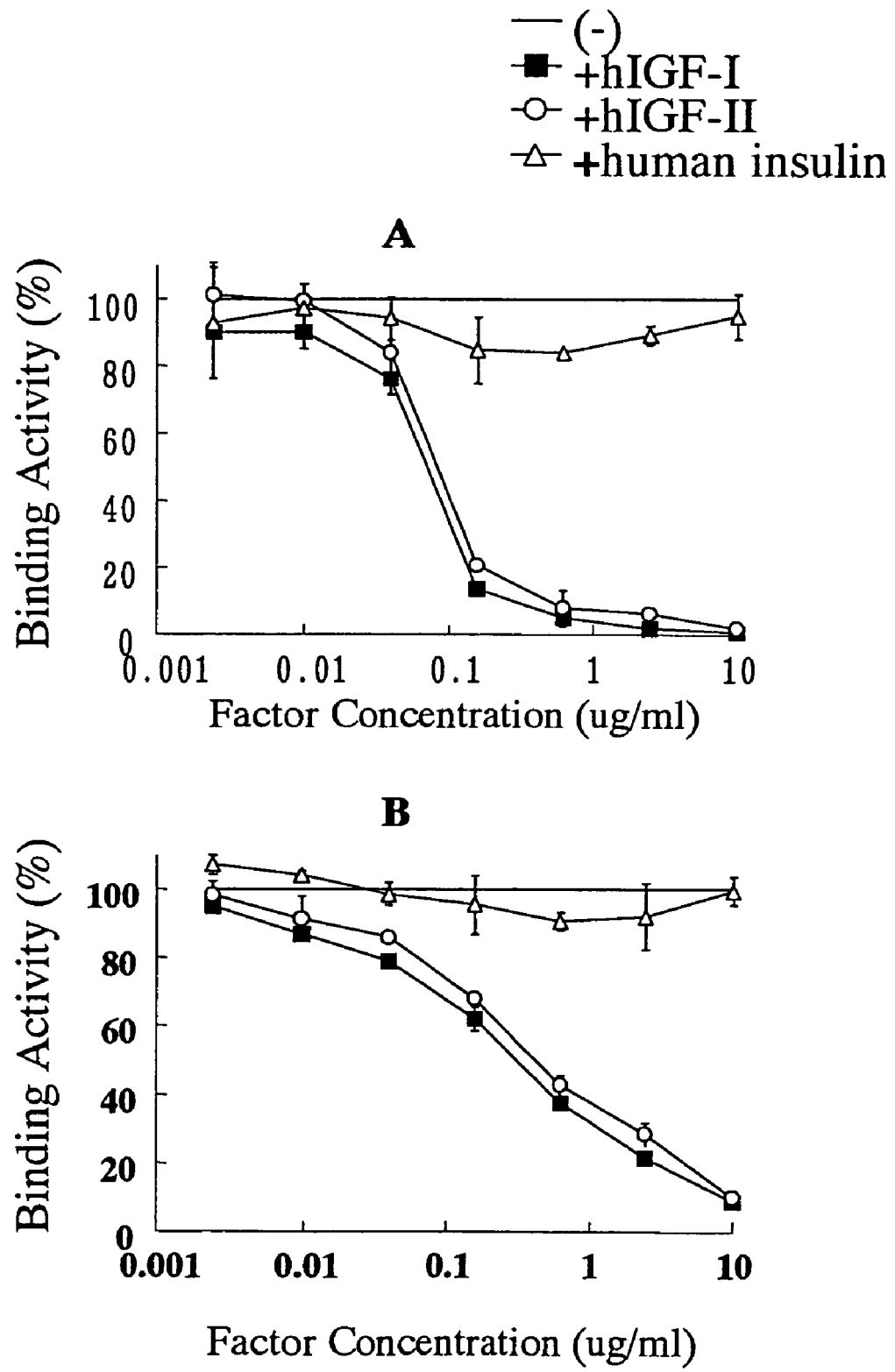

FIG. 4 shows activities of hIGF-I, hIGF-II and human insulin to inhibit binding of anti-hIGF antibody KM1468 to hIGF-I and hIGF-II. A shows inhibition by respective factors upon binding of KM1468 to hIGF-I, and B upon binding of KM1468 to hIGF-II. The abscissa shows concentration of respective factors (μg/ml), and the ordinate shows binding activity (%) wherein the value with no addition of factors is defined as 100%. ■ shows the reactivity when hIGF-I was added, and ○ shows the reactivity when hIGF-II was added and Δ shows the reactivity when human insulin was added.

Figure 5:
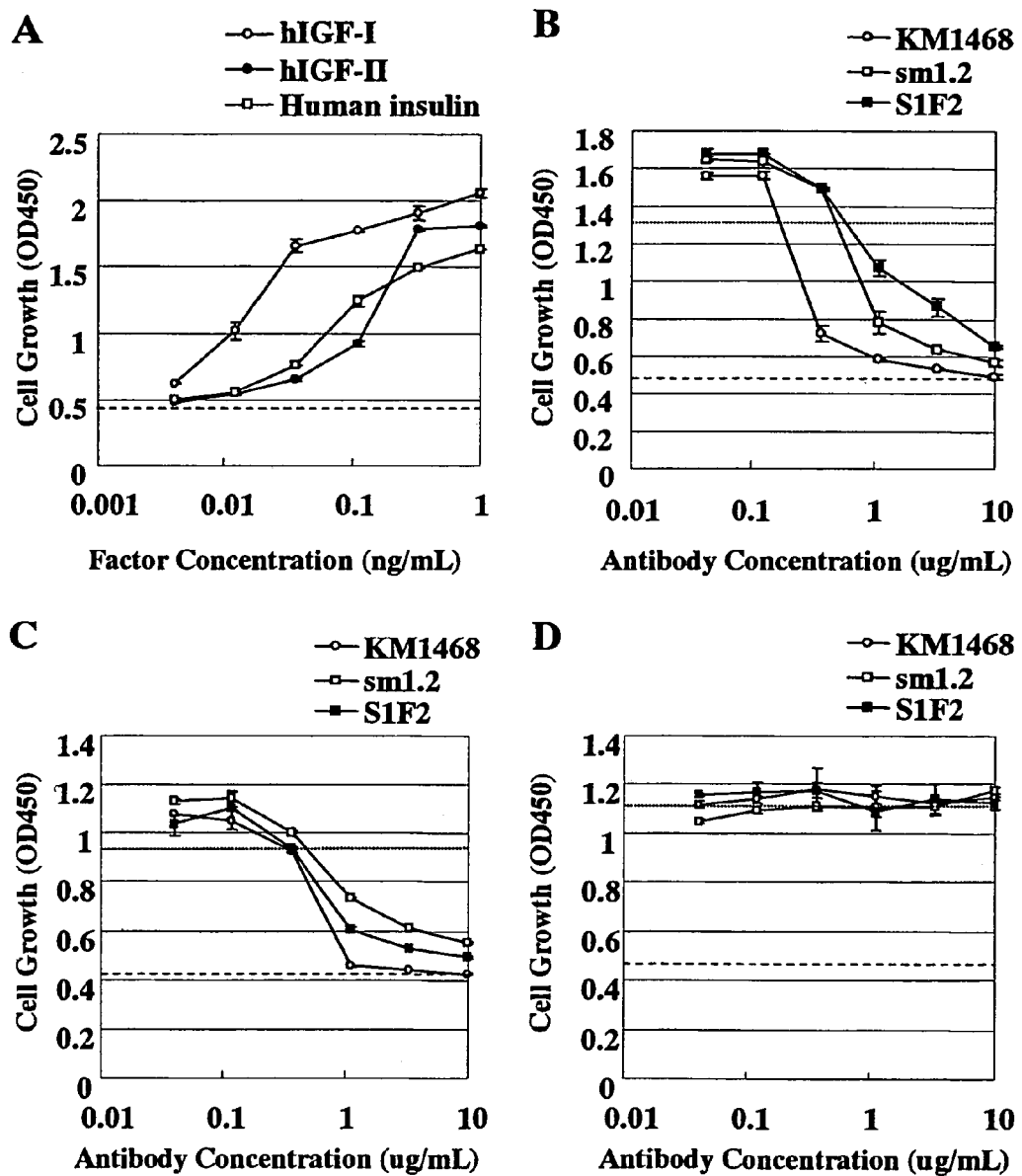

FIG. 5 shows influence of anti-hIGF antibody KM1468, sm1.2 and S1F2 upon the growth of a human breast cancer cell strain MCF7 by hIGF and human insulin. A shows cell growth activity by respective factors. The abscissa shows concentration of respective factors (μg/ml), and the ordinate shows growth (OD450). ○ shows activity of hIGF-I, ■ shows activity of hIGF-II and □ shows activity of human insulin. B, C and D show influence of respective antibodies upon growth activity by hIGF-I, and by hIGF-II and by human insulin, respectively. The abscissa shows antibody concentration (μg/ml), and the ordinate shows growth (OD450). Fine dotted line shows growth with no addition of antibodies, and dotted line shows growth with no addition of respective factors. ○ shows the activity of KM1468, □ shows the activity of sm1.2 and ■ shows the activity of S1F2.

Figure 6:
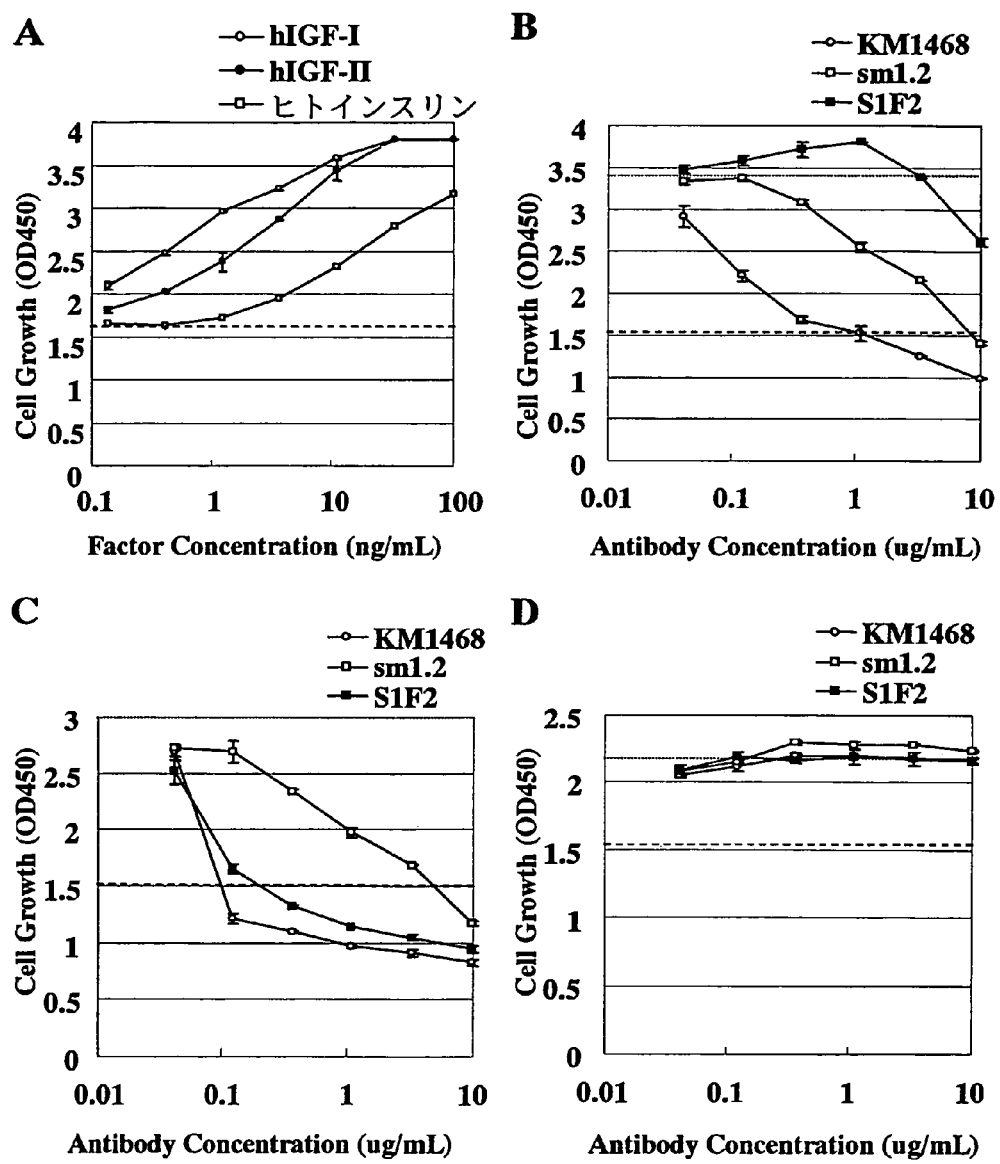

FIG. 6 shows influence of anti-hIGF antibody KM1468, sm1.2 and S1F2 upon the growth of a human colon cancer cell strain HT-29 by hIGF and human insulin. A shows cell growth activity by respective factors. The abscissa shows concentration of respective factors (ng/ml), and the ordinate shows growth (OD450). ○ shows activity of hIGF-I, ● shows the activity of hIGF-II and □ shows the activity of human insulin. B, C and D show influence of respective antibodies upon growth activity by hIGF-I, by hIGF-II by human insulin, respectively. The abscissa shows antibody concentration (μg/ml), and the ordinate shows growth (OD450). Fine dotted line shows growth with no addition of antibodies, and dotted line shows growth with no addition of respective factors. ○ shows the activity of KM1468, open square shows the activity of sm1.2 and ● shows the activity of S1F2.

Figure 7:
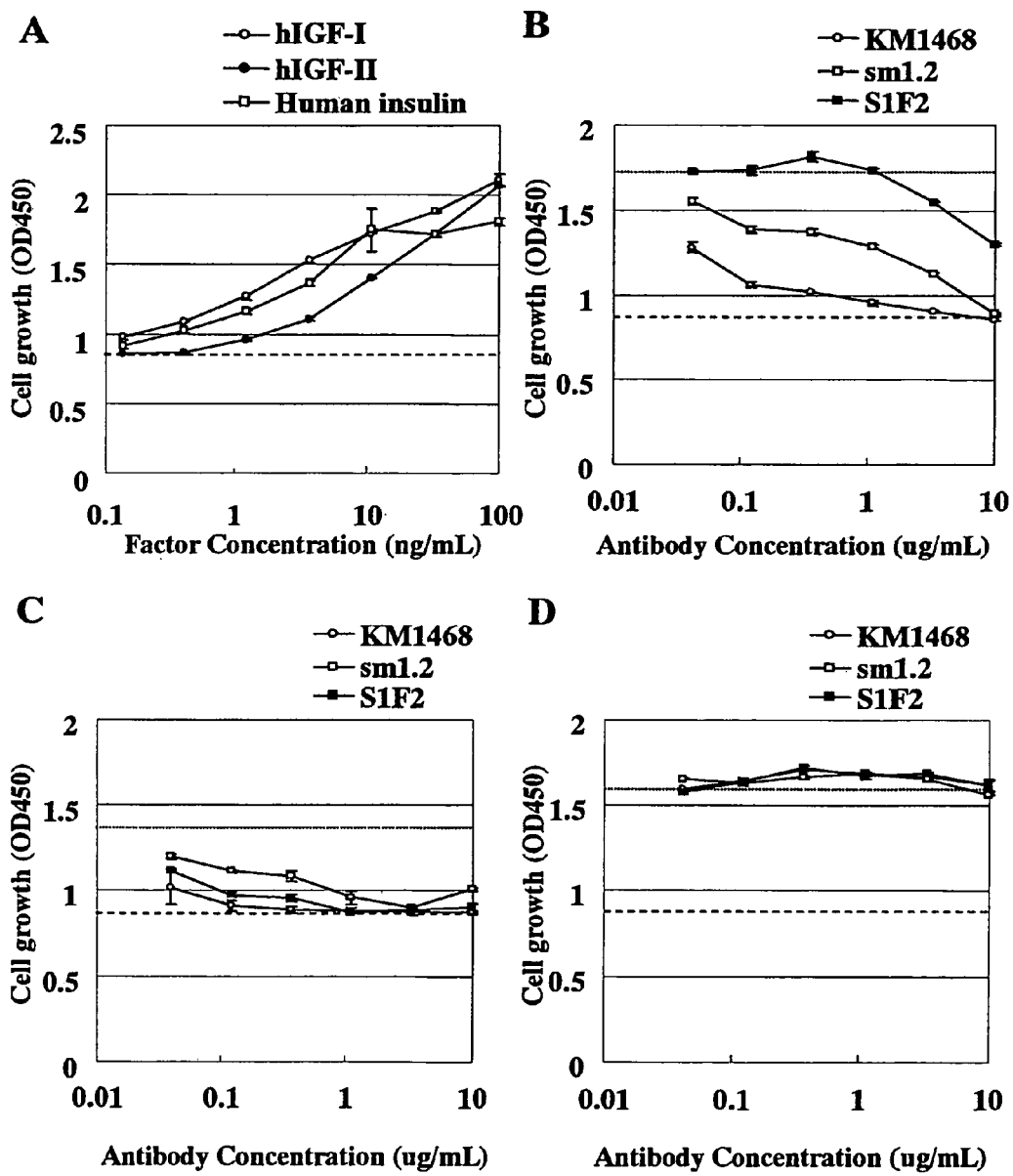

FIG. 7 shows influence of anti-hIGF antibody KM1468, sm1.2 and S1F2 upon the growth of a human osteosarcoma cell strain MG63 by hIGF and human insulin. A shows cell growth activity by respective factors. The abscissa shows concentration of respective factors (ng/ml), and the ordinate shows growth (OD450). ○ shows activity of hIGF-I, ● shows the activity of hIGF-II and □ shows the activity of human insulin. B, C and D show influence of respective antibodies upon growth activity by hIGF-I, by hIGF-II and by of human insulin, respectively. The abscissa shows antibody concentration (μg/ml), and the ordinate shows growth (OD450). Fine dotted line shows growth with no addition of antibodies, and dotted line shows growth with no addition of respective factors. ○ shows the activity of KM1468, □ shows the activity of sm1.2 and ■ shows the activity of S1F2.

Figure 8:
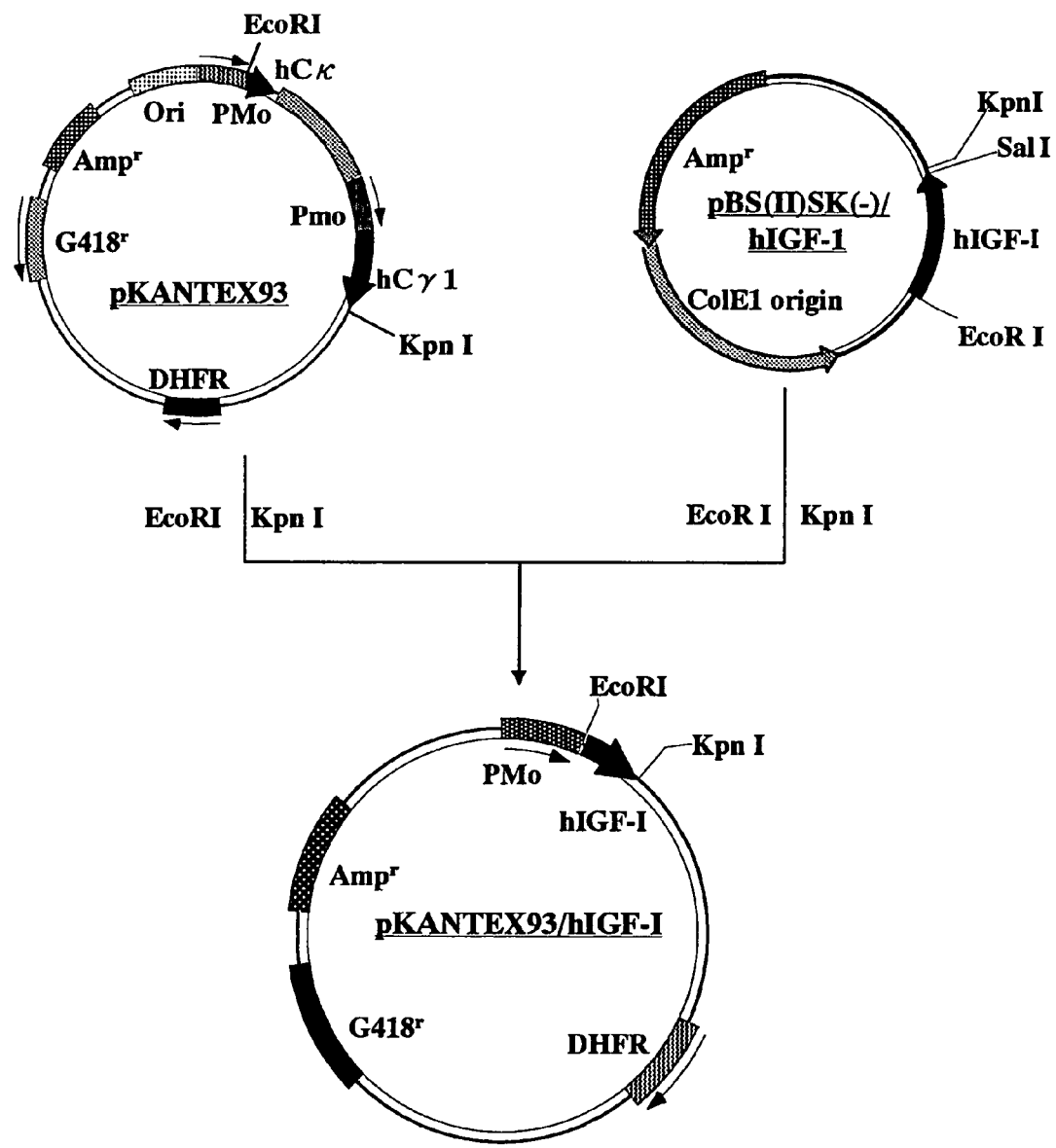

FIG. 8 is a graph showing construction steps of plasmids PBS(II)SK(−)/hIGF-I and pKANTEX93/hIGF-I.

Figure 9:
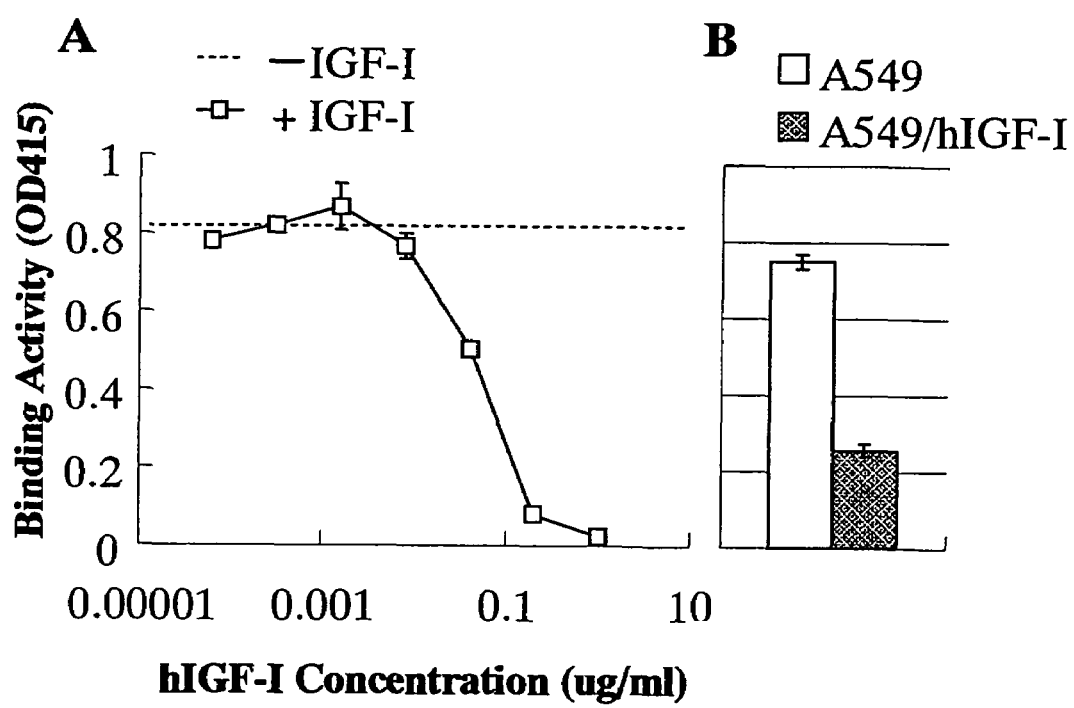

FIG. 9 is a drawing showing expression of hIGF-I in A549/hIGF-I cell. A shows inhibition by a recombinant hIGF-I protein. The abscissa shows concentration of the added recombinant hIGF-I protein, and the ordinate shows color development (OD415). B shows hIGF-I contained in culture supernatants of A549 cell and A549/hIGF-I cell. Void shows A549 cell and netting shows A549/hIGF-I cell.

Figure 10:
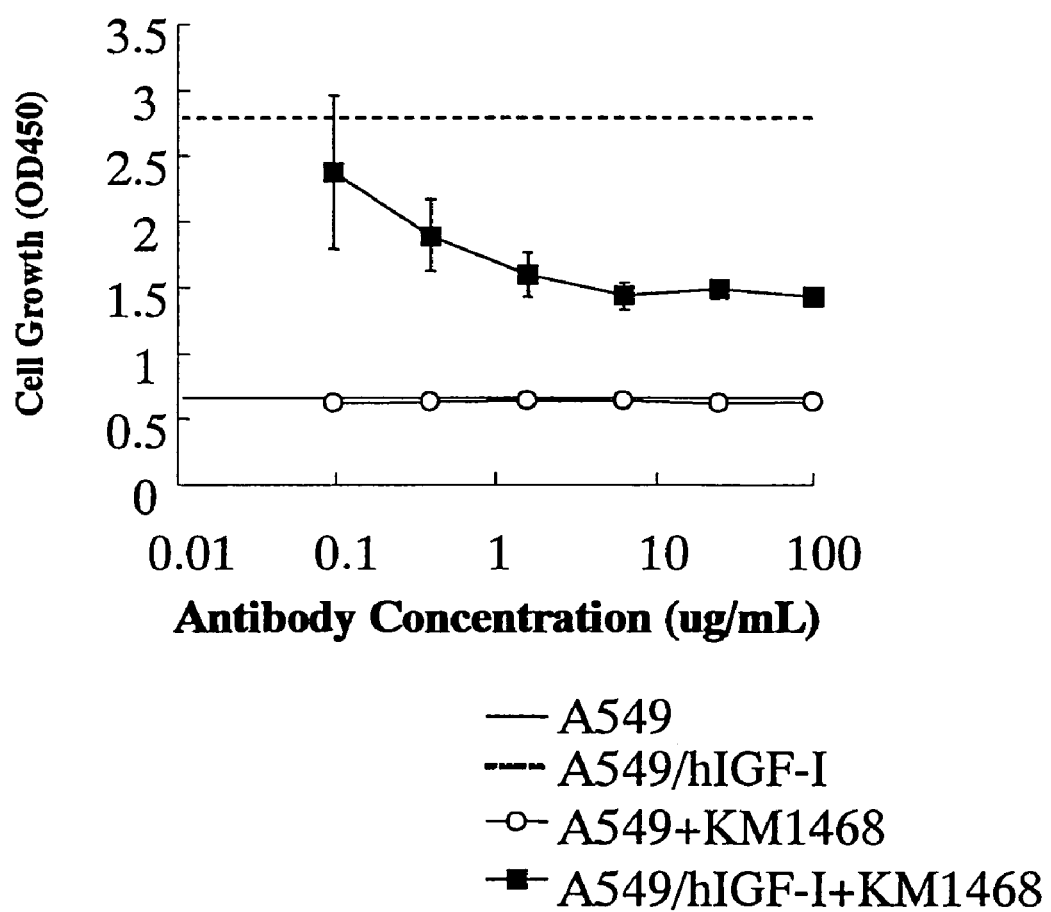

FIG. 10 shows cell growth inhibitory effect of KM1468 upon hIGF-I expressing cells. Broken like shows growth of A549/hIGF-I cell in the absence of anti-hIGF antibody KM1468, and solid line shows growth of A549 cell in the absence of anti-hIGF antibody KM1468. ■ shows growth of A549/hIGF-I cell in the presence of anti-hIGF antibody KM1468, and ○ shows growth of A549 cell in the presence of anti-hIGF antibody KM1468.

Figure 11:
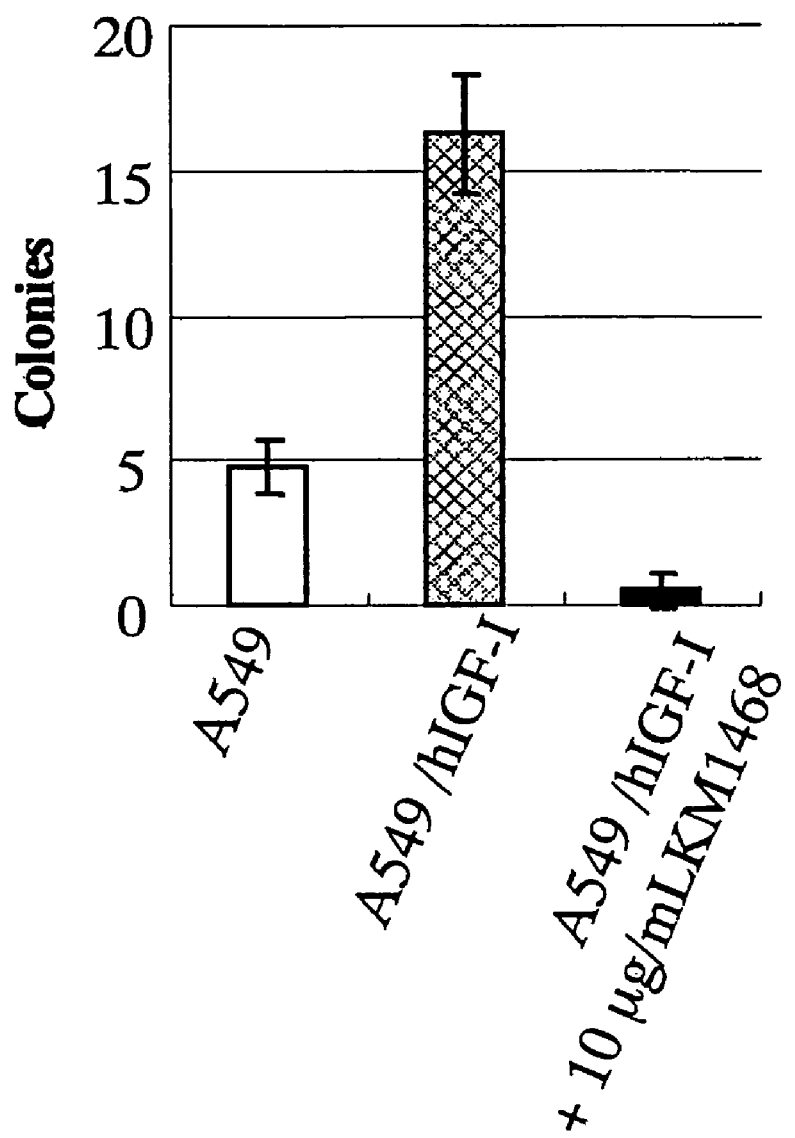

FIG. 11 is a graph showing anchorage independent growth inhibitory effect of KM1468. In the drawing, voided column shows the number of formed colonies of A549 cell, netted column shows the number of formed A549/hIGF-I cells, and black-finished column shows the number of formed A549/hIGF-I cells in the presence of anti-hIGF antibody KM1468.

Figure 12:
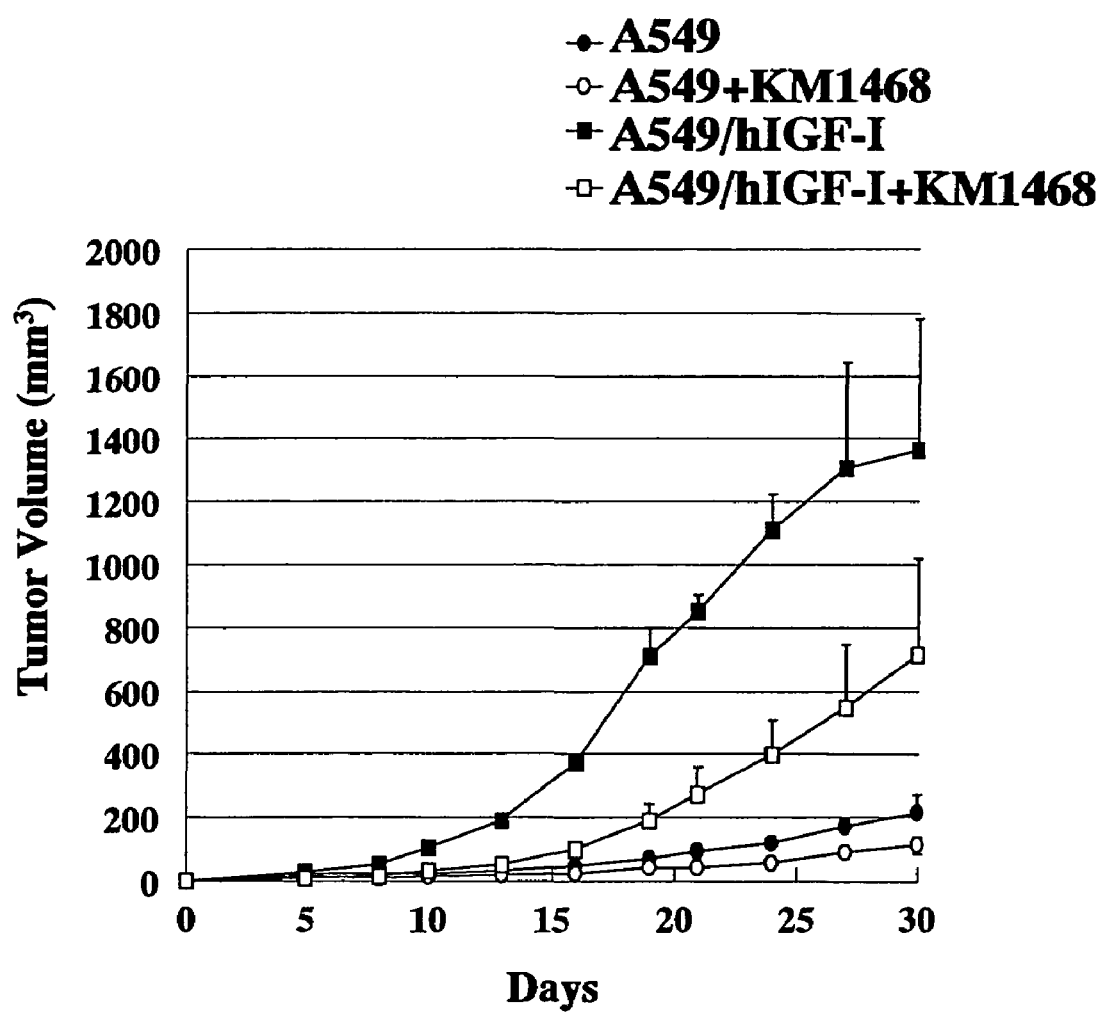

FIG. 12 is a graph showing antitumor effect of anti-hIGF antibody KM1468. The abscissa shows the number of elapsed days after tumor transplantation, and the ordinate shows tumor volume. Among the mice transplanted with A549 cell, ● shows effect in the absence of anti-hIGF antibody KM1468, and ○ shows effect in the presence of anti-hIGF antibody KM1468. Among the mice transplanted with A549/hIGF-I cell, ■ shows effect in the absence of anti-hIGF antibody KM1468, and ■ shows effect in the presence of anti-hIGF antibody KM1468.

Figure 13:
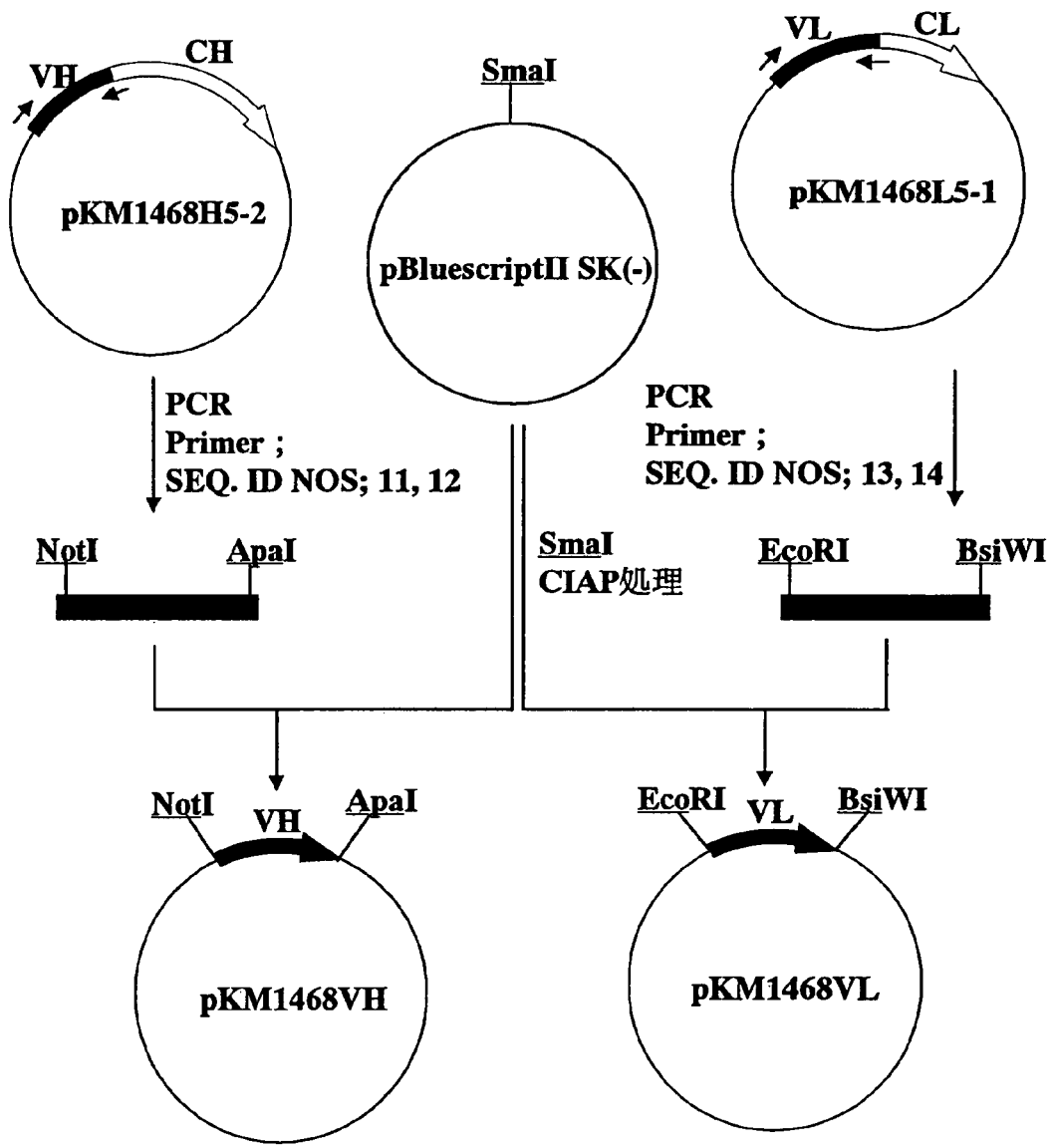

FIG. 13 is a drawing showing construction steps of plasmids pKM1468VH and pKM1468VL.

Figure 14:
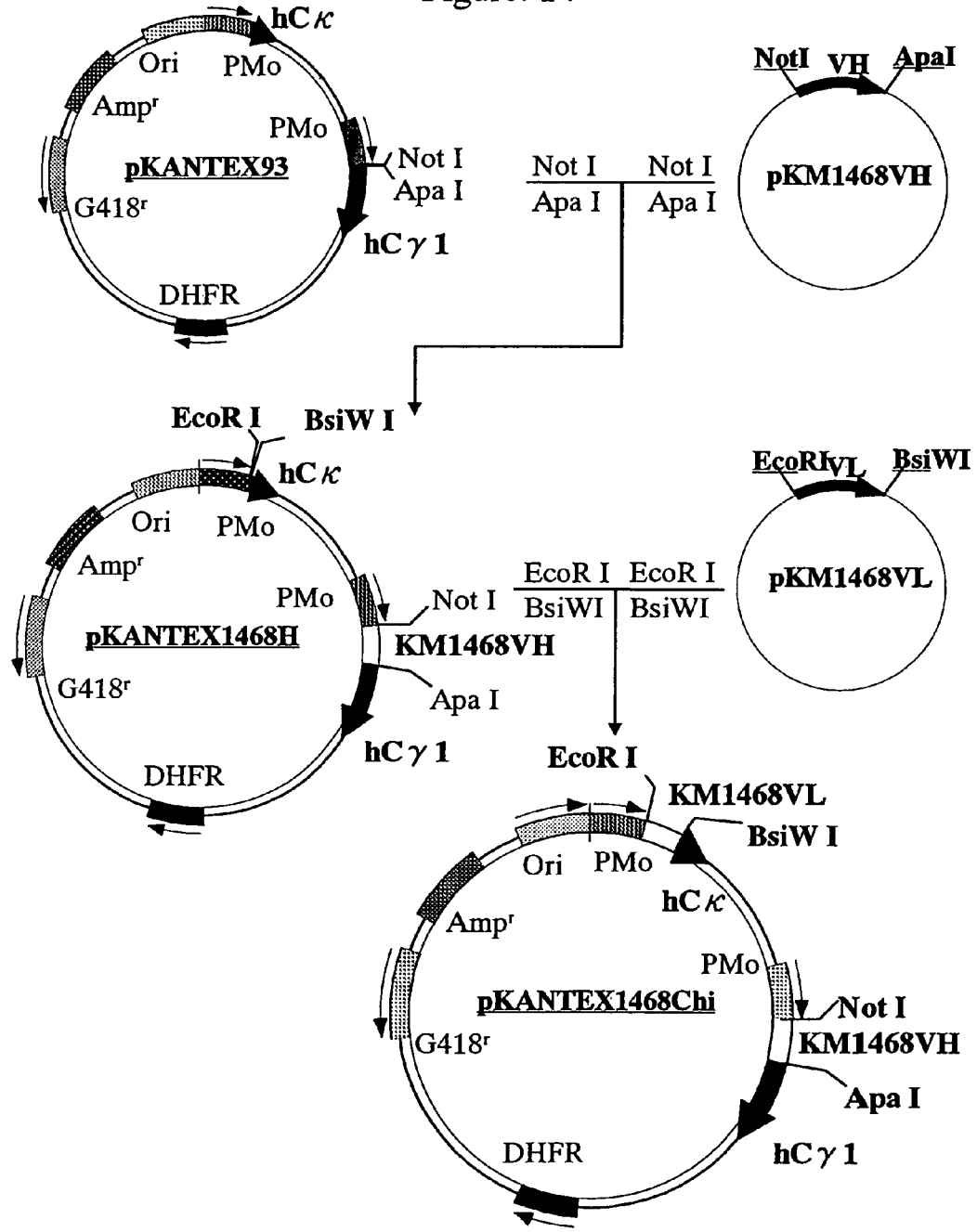

FIG. 14 is a drawing showing construction steps of plasmid pKANTEX1468Chi.

Figure 15:
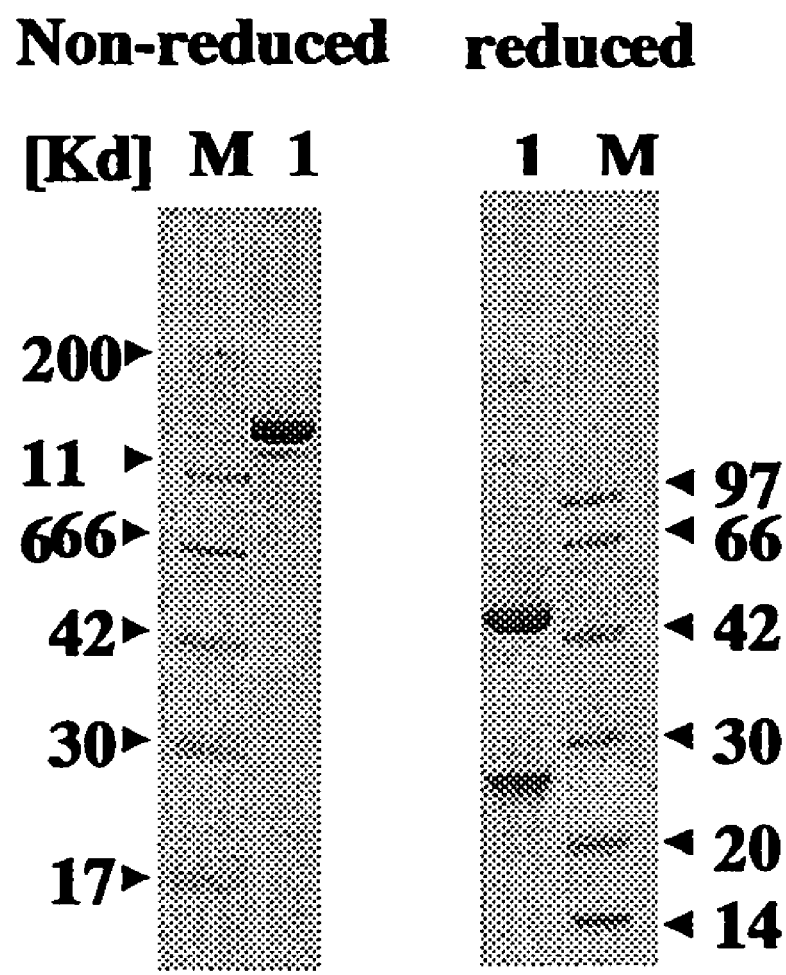

FIG. 15 shows SDS-PAGE (using a 4 to 15% gradient gel) electrophoresis pattern of purified anti-hIGF chimeric antibody KM3002. The left side is the electrophoresis pattern under non-reducing condition, and the right side is the electrophoresis pattern under reducing condition. Lane M shows high molecular weight markers under non-reducing condition or low molecular weight markers under reducing condition, and lane 1 shows electrophoresis pattern of KM3002.

Figure 16:
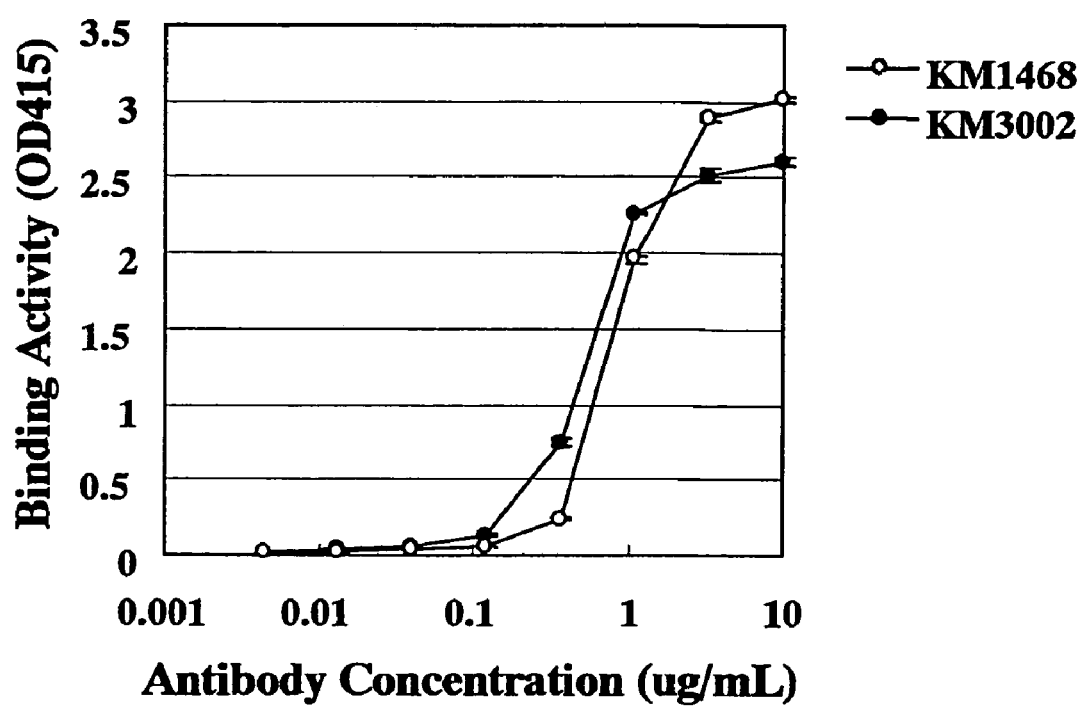

FIG. 16 shows reaction of anti-hIGF rat antibody KM1468 and anti-hIGF chimeric antibody KM3002 upon hIGF-I. The abscissa shows antibody concentration (μg/ml), and the ordinate shows binding activity (OD415). ○ shows reactivity of KM1468, and ● shows reactivity of KM3002.

Figure 17:
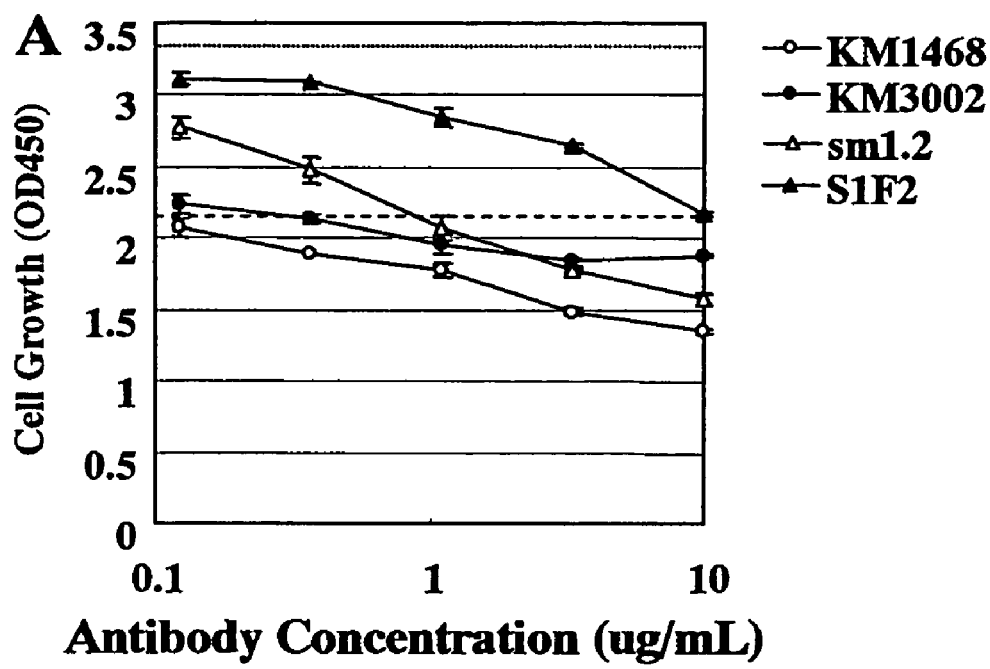
Figure 17:
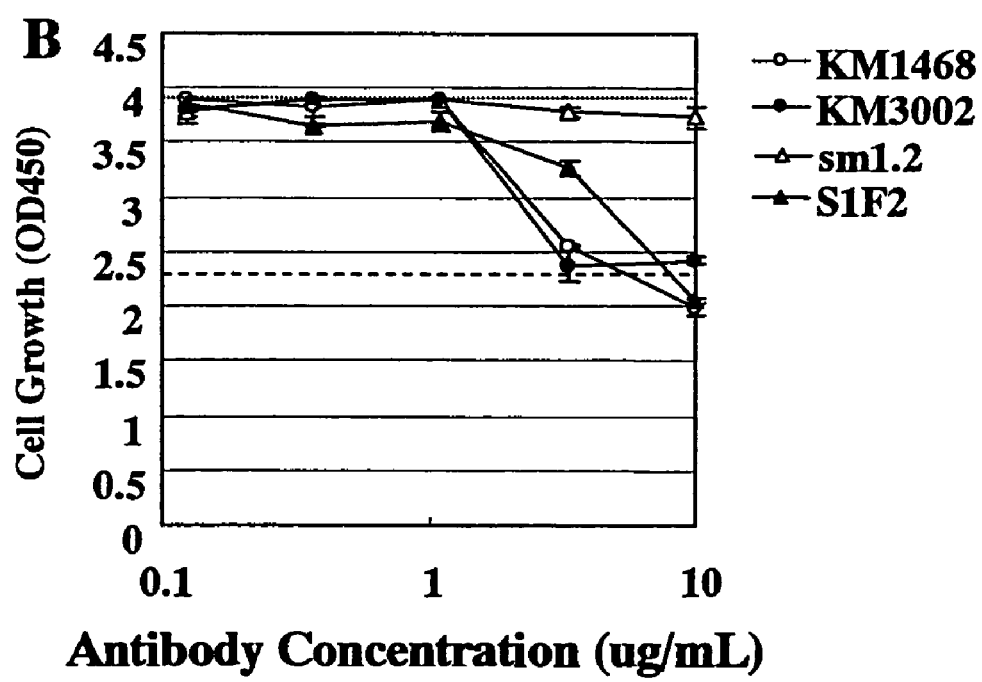

FIG. 17 shows influence of anti-hIGF antibody KM1468, sm1.2, S1F2 and anti-hIGF chimeric antibody KM3002 upon the growth of a human colon cancer cell strain HT-29 by hIGF. A and B show influence of respective antibodies upon growth activity by hIGF-I and by hIGF-II, Δ respectively. The abscissa shows antibody concentration (μg/ml), and the ordinate shows growth (OD450). Fine dotted line shows growth in the absence of antibodies, and dotted line shows growth in the absence of respective factors. ○ shows the activity of KM1468, ● shows the activity of KM3002, Δ shows the activity of sm1.2 and ▲ shows the activity of S1F2.

The present invention will be described below by referring to examples, but the present invention is not limited thereto.

BEST MODE FOR CARRYING OUT THE INVENTION

Example 1

Preparation of Antibody to hIGF-I (1) Immunization of Animal and Preparation of Antibody Producing Cell A recombinant hIGF-I (manufactured by R & D) was conjugated with methylated BSA (manufactured by SIGMA) for the purpose of increasing its immunogenicity, and use as the immunogen. That is, the methylated BSA dissolved in redistilled water was mixed at a ratio of methylated BSA: hIGF-I=1:4 (weight ratio) at 4° C. and stirred for 10 seconds using a Vortex mixer. Thereafter, this was mixed with Freund's complete adjuvant or Freund's incomplete adjuvant at a volume ratio of 1:1 using a syringe equipped with connecting needles and used as the immunogen (hereinafter referred to as methylated BSA-hIGF-I adjuvant).

The methylated BSA-hIGF-I adjuvant prepared as described in the above using Freund's complete adjuvant (equivalent, to 100 μg of hIGF-I) was administered to an SD rat of 5-weeks-old, and the immunogen prepared in the same manner using Freund's incomplete adjuvant was administered starting 2 weeks thereafter once a week for 4 times in total.

A blood sample was collected from the venous plexus of the fundus of the eye, antibody titer in the serum was examined by the binding ELISA shown in Example 1(4), and the spleen was excised from a rat whose serum showed a sufficient antibody titer 3 days after the final immunization.

The spleen was cut into pieces in MEM medium (manufactured by Nissui Pharmaceutical), unbound using a pair of forceps and centrifuged (1,200 rpm, 5 minutes), and then the supernatant was discarded, the resulting precipitate was treated with Tris-ammonium chloride buffer (pH 7.65) for 1 to 2 minutes to eliminate erythrocytes, and the remaining cells were washed three times with MEM and submitted for cell fusion.

(2) Preparation of Mouse Myeloma Cells

An 8-azaguanine-resistant mouse myeloma cell strain P3-U1 was cultured using a normal medium, and $2 \times 10^7$ or more of the cells were prepared for the cell fusion.

(3) Preparation of Hybridoma

The rat spleen cells obtained in Example 1(1) and the myeloma cells obtained in (2) were mixed at a ratio of 10:1 and centrifuged (1,200 rpm, 5 minutes), the supernatant was discarded, and then, while stirring at 37° C., to the precipitated cells were added a fusion medium (a mixture composed of 2 g of PEG-1000, 2 ml of MEM and 0.7 ml of dimethyl sulfoxide) in an amount of 0.2 to 1.0 ml per $1.0 \times 10^2$ rat spleen cells, 1 to 2 ml of MEM-several times at 1- to 2-minute intervals and then a portion of MEM further added thereto to adjust the total volume to 50 ml. After centrifugation (900 rpm, 5 minutes), the supernatant was discarded, and the resulting cells were gently loosened and suspended in 100 ml of HAT medium {a medium prepared by supplementing the normal medium [a medium prepared by adding 1.5 mM glutamine, 50 μM 2-mercaptoethanol, 10 μg/ml gentamicin and 10% fetal calf serum (hereinafter referred to as FCS) to RPMI-1640 medium] with 0.1 mM hypoxanthine, 15 μM thymidine and 0.4 μM aminopterin}.

This suspension was dispensed in 100 μl/well portions into a 96 well culture plate and incubated in a 5% $CO_2$ incubator at 37° C. for a period of from 7 to 14 days. Wells in which the culture supernatants which reacted with the methylated BSA-hIGF-I but did not react with a negative control methylated BSA-BSA [a conjugate prepared by carrying out the same reaction of the above Example 1(1) using BSA] were selected by the binding ELISA as described in Example 1(4), and anti-hIGF-I rat monoclonal antibody producing hybridomas were established by carrying out single cell cloning twice by changing the medium to HT medium (a medium prepared by removing aminopterin from the HAT medium) and the normal medium.

As a result, 6 hybridoma clones KM1468, KM1469, KM1470, KM1471, KM1472 and KM1473 having the reactivity shown in FIG. 1 were obtained. When subclass of the antibody produced by each hybridoma was examined by ELISA using a subclass typing kit, subclass of each antibody was IgG2b.

(4) Selection of Monoclonal Antibody (binding ELISA)

The methylated BSA-hIGF-I prepared in Example 1(1) and the methylated BSA-BSA as a negative control were used as the antigens to be immobilized on the ELISA plate. Each of the antigens was dispensed in 50 μl/well portions as a BSA concentration of 10 μg/ml into a 96 well ELISA plate (manufactured by Greiner) and allowed to stand overnight at 4° C. to effect its immobilized. After washing with PBS, PBS containing 1% BSA (hereinafter referred to as BSA-PBS) was added in 100 μl/well portions and allowed to react at room temperature for 1 hour to carry out blocking of the remaining active groups. After discarding BSA-PBS, immunized rat antiserum, culture supernatant of each anti-hIGF-I monoclonal antibody producing hybridoma or purified anti-hIGF-I rat monoclonal antibody was dispensed in 50 μl/well portions and allowed to react at room temperature for 2 hours. After the reaction, each well was washed with PBS containing 0.05% Tween 20 (hereinafter referred to as Tween-PBS), and then 4,000 times-diluted peroxidase-labeled rabbit anti-rat Ig antibody (manufactured by DAKO) was added as the secondary antibody in 50 μl/well portions and allowed to react at room temperature for 1 hour. After the reaction and subsequent washing with Tween-PBS, an ABTS substrate solution [a solution prepared by dissolving 0.55 g of 2,2'-azinobis(3-ethylbenzothiazoline-6-sulfonic acid) ammonium salt in 1 liter of 0.1 M citrate buffer (pH 4.2), and further adding thereto 1 μl/ml of hydrogen peroxide just before use] was added in 50 μl/well portions to effect color development, and then absorbance at 415 nm (hereinafter referred to as OD415) was measured using a plate reader Emax (manufactured by Molecular Devices).

(5) Purification of Monoclonal Antibody

Each of the hybridoma-clones obtained in Example 1(3) was intraperitoneally injected into 8-week-old female Balb/c nude mice which had been treated with pristane, at a dose of to 20×10$^6$ cells per animal. After 10 to 21 days, the ascitic fluid was collected (1 to 8 ml/animal) from the mice in which the hybridoma change into ascites tumor and then centrifuged (3,000 rpm, 5 minutes) to remove solid. Thereafter, the IgG fraction was purified by the caprylic acid precipitation method (Antibodies, A Laboratory Manual, Cold Spring Harbor Laboratory, 1988) and used as a purified monoclonal antibody.

Example 2

Examination of Reactivity of Anti-hIGF-I Rat Monoclonal Antibody (1) Reactivity to Natural Three-Dimensional Structure of hIGF-I Reactivity of the anti-hIGF-I rat monoclonal antibodies selected in Example 1(3) with hIGF-I which maintains natural three-dimensional structure in a liquid phase system was examined by a competitive ELISA shown below.

Each of 5-fold serial dilutions of hIGF-I starting from 20 μg/ml was dispensed in 50 μg/well portions into the plate shown in Example 1(4) in which the methylated BSA-hIGF-I prepared in Example 1(1) had been immobilized, and then each of the solutions prepared by diluting purified antibodies of the anti-hIGF-I rat monoclonal antibodies (KM1468: 6.0 μg/ml, KM1470: 1.0 μg/ml, KM1471: 0.16 μg/ml, KM1472: 7.0 μg/ml, KM1473: 1.2 μg/ml) was dispensed in 50 μl/well portions, mixed and allowed to react at room temperature for 2 hours. After the reaction and subsequent washing with Tween-PBS, 4,000 times-diluted peroxidase-labeled rabbit anti-rat Ig antibody (manufactured by DAKO) was added in 50 μl/well portions and allowed to react at room temperature for 1 hour. After the reaction and subsequent washing with Tween-PBS, the ABTS substrate solution [a solution prepared by dissolving 0.55 g of 2,2'-azinobis(3-ethylbenzothiazoline-6-sulfonic acid) ammonium salt in 1 liter of 0.1 M citrate buffer (pH 4.2), and further adding thereto 1 μl/ml of hydrogen peroxide just before use] was added in 50 μl/well portions to effect color development, and then OD415 was measured using a plate reader Emax (manufactured by Molecular Devices).

Figure 2:
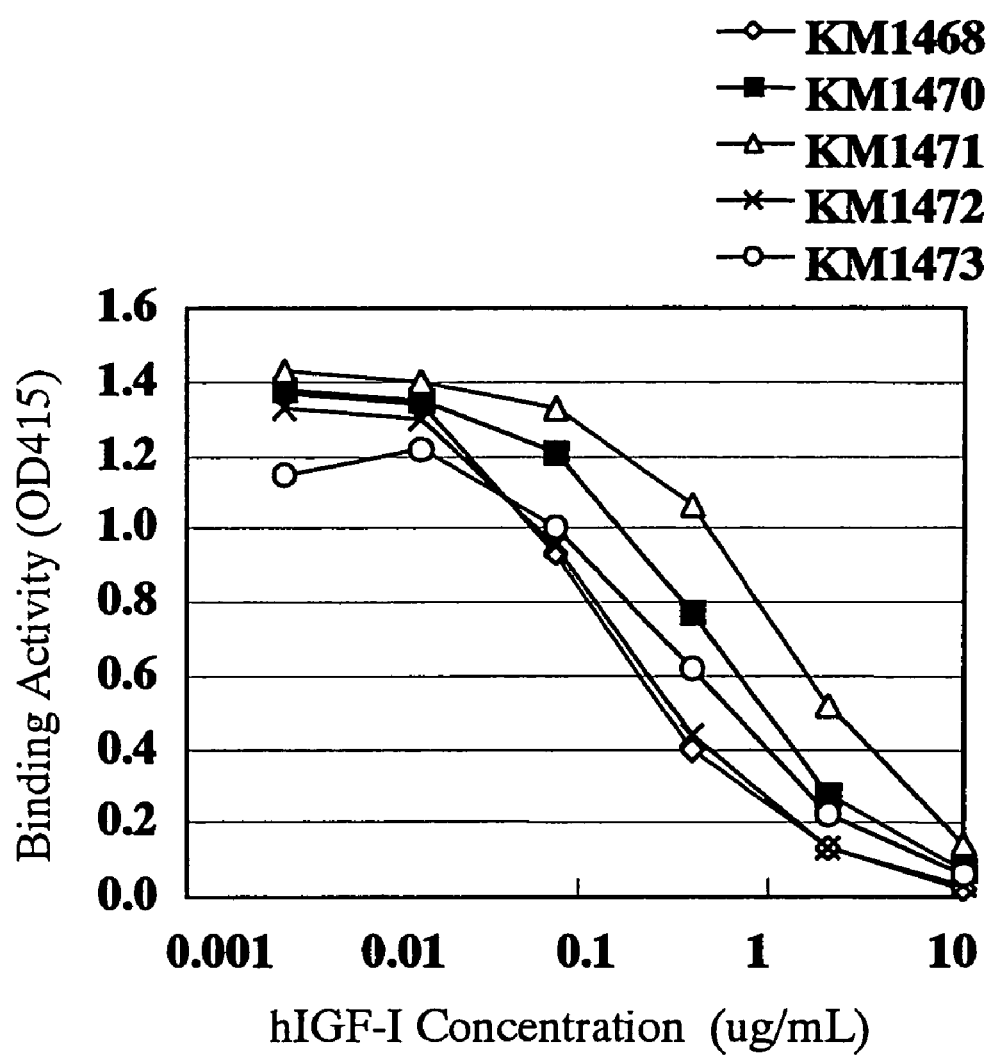
FIG. 2 shows reactivity of anti-hIGF rat monoclonal antibody for hIGF-I having natural three-dimensional structure in a liquid system (competitive ELISA).

As shown in FIG. 2, each of the anti-hIGF-I rat monoclonal antibodies showed the reactivity with natural three-dimensional structure of hIGF-I in the liquid phase. In addition, in the case of KM1468 which showed the highest sensitivity, it was able to detect the hIGF-I having natural three-dimensional structure contained in the liquid phase system, up to a concentration of 16 ng/ml.

(2) Reactivity of Anti-hIGF Antibody KM1468 with hIGF-I by Competitive ELISA

A possibility was suggested in Example 2(1) that the anti-hIGF antibody KM1468 recognizes three-dimensional structure of hIGF-I. However, since there is also a possibility that KM1468 recognizes amino acid primary sequence, its reactivity with hIGF-I partial peptides was analyzed.

(2-1) Synthesis of hIGF-I Partial Peptides

Partial peptides of hIGF-I were synthesized in accordance with the method described in WO 01/64754. The synthesized peptides were peptides corresponding to a sequence of 1st to 18th positions of hIGF-I (SEQ ID NO: 17, hereinafter referred to as p1-18), 14th to 30th positions thereof (SEQ ID NO: 18, hereinafter referred to as p14-30), 24th to 35th positions thereof (SEQ ID NO: 19, hereinafter referred to as p24-35), 29th to 41st positions thereof (SEQ ID NO: 20, hereinafter referred to as p29-41), 36th to 47th positions thereof (SEQ ID NO: 21, hereinafter referred to as p36-47), 41st to 56th positions thereof (SEQ ID NO: 22, hereinafter referred to as p41-56), 52nd to 70th positions thereof (SEQ ID NO: 23, hereinafter referred to as p52-70), 53rd to 61st positions thereof (SEQ ID NO: 24, hereinafter referred to as p53-61) and 61st to 70th positions thereof (SEQ ID NO: 25, hereinafter referred to as p61-70), and they were designed such that they covered full length of hIGF-I. Regarding Cys existing in inner part of these peptides, sequences in which it was replaced by Ser or Ala were synthesized. In addition, regarding the sequence corresponding to 41st to 56th positions, a sequence having Cys inside therein (SEQ ID NO: 26, hereinafter referred to as p41-56C) was also synthesized.

(2-2) Analysis of Antigen Recognition Site of Anti-hIGF Antibody KM1468

Analysis of antigen recognition site of anti-hIGF antibody KM1468 was carried out using the various peptides synthesized in the above (2-1) by a competitive ELISA shown below.

Plates on which antigens were immobilized were prepared as shown in Example 1(4), anti-hIGF antibody KM1468 diluted to 4.0 μg/ml was dispensed therein in 50 μl/well portions, and then solutions of 3-fold serial dilutions of each peptide prepared by starting from 50 μg/ml, alone or in various combinations, or of hIGF-I were dispensed in 50 μl/well portions, mixed and allowed to react at room temperature for 1 hour. After the reaction and subsequent washing with Tween-PBS, 4,000 times-diluted peroxidase-labeled rabbit anti-rat Ig antibody (manufactured by DAKO) was added as the secondary antibody in 50 μl/well portions and allowed to react at room temperature for 1 hour. After the reaction and subsequent washing with Tween-PBS, the ABTS substrate solution [a solution prepared by dissolving 0.55 g of 2,2'-azinobis(3-ethylbenzothiazoline-6-sulfonic acid) ammonium salt in 1 liter of 0.1 M citrate buffer (pH 4.2), and further adding thereto 1 μl/ml of hydrogen peroxide just before use] was added in 50 μl/well portions to effect color development, and then OD415 was measured using a plate reader Emax (manufactured by Molecular Devices). The results are expressed by relative values (%) wherein OD415 when an antibody alone is added is defined as 100.

Figure 3:
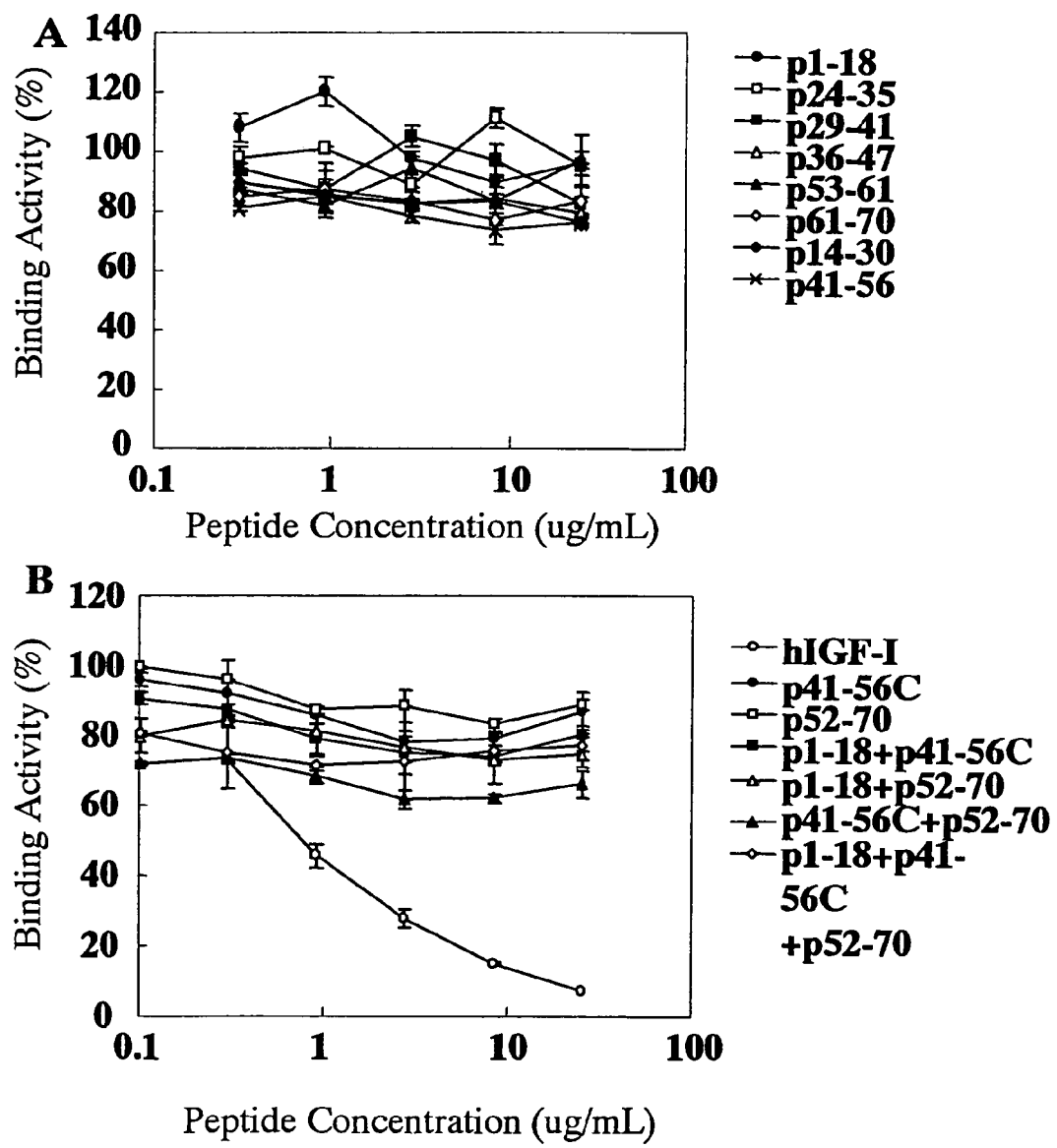
FIG. 3 shows activity of various peptides to inhibit binding of anti-hIGF rat monoclonal antibody KM1468 to hIGF-I.

As shown in FIG. 3, binding of the anti-hIGF antibody KM1468 to hIGF-I was inhibited by hIGF-I in a concentration-dependent manner, but the inhibitory activity was not observed in these peptides regardless of using alone or combination. The above results strongly suggest that KM1468 does not merely recognaize an amino acid primary sequence of hIGF-I but recognizes three-dimensional structure of hIGF-I.

(3) Verification of Cross Reactivity of Anti-hIGF Antibody KM1468 by Competitive ELISA Cross reactivity of the purified anti-hIGF antibody KM1468 with hIGF-II and human insulin was examined by the competitive ELISA shown below. As the antigens, hIGF-I (manufactured by Pepro Tech), hIGF-II (manufactured by Pepro Tech) and human insulin (manufactured Wako Pure Chemical Industries) were used.

The methylated BSA-hIGF-I antigen prepared in Example 1(1) or a methylated BSA-hIGF-II antigen prepared in the same manner as in Example 1(1) was immobilized on a plate in accordance with the method shown in Example 1(4), at a concentration of 0.1 μg/ml in the case of the methylated BSA-hIGF-I antigen, or at a concentration of 1.0 μg/ml in the case of the methylated BSA-hIGF-II antigen, KM1468 diluted to 0.6 μg/ml was dispensed therein in 25 μl/well portions, and then each of 4-fold serial dilutions of hIGF-I, hIGF-II or human insulin prepared by starting from 20 μg/ml was dispensed in 25 μl/well portions, mixed and allowed to react at room temperature for 1 hour. After the reaction and subsequent washing with Tween-PBS, 1,000 times-diluted peroxidase-labeled rabbit anti-rat Ig antibody (manufactured by DAKO) was added in 50 μl/well portions as the secondary antibody in the case of the anti-hIGF antibody KM1468. After the reaction and subsequent washing with Tween-PBS, the ABTS substrate solution [a solution prepared by dissolving 0.55 g of 2,2'-azinobis(3-ethylbenzothiazoline-6-sulfonic acid) ammonium salt in 1 liter of 0.1 M citrate buffer (pH 4.2), and further adding thereto 1 μl/ml of hydrogen peroxide just before use] was added in 50 μl/well portions to effect color development, and then OD415 was measured using a plate reader Emax (manufactured by Molecular Devices). The results are represented by relative values (%) wherein OD415 when an antibody alone is added is defined as 100.

The results are shown in FIG. 4. As shown in FIG. 4A, binding of the anti-hIGF antibody KM1468 to hIGF-I was strongly inhibited by hIGF-I and hIGF-II. In the same manner, as shown in FIG. 4B, binding of the anti-hIGF antibody KM1468 to hIGF-II was strongly inhibited by hIGF-I and hIGF-II. In addition, these inhibitions by hIGF-I and hIGF-II were the same degree. That is, it is shown that the anti-hIGF antibody KM1468 can react with both of hIGF-I and hIGF-II by almost the same strength. On the other hand, binding of the anti-hIGF antibody KM1468 to hIGF-I or hIGF-II was not inhibited by human insulin.

Example 3

Verification of Reactivity of Anti-hIGF Antibody with IGF

Comparison of the reactivity of KM1468 and two commercially available anti-hIGF antibodies with antigens was carried out in the following manner. As the antibodies, the anti-hIGF antibody KM1468, sm1.2 as a commercially available anti-hIGF-I antibody (manufactured by Upstate Biotechnology) and S1F2 as a commercially available anti-hIGF-II antibody (manufactured by Upstate Biotechnology) were used. As the antigens, hIGF-I (manufactured by Pepro Tech), hIGF-II (manufactured by Pepro Tech) and human insulin (manufactured by Wako Pure Chemical Industries) were used.

(1) Measurement of Binding Strength Using Surface Plasmon Resonance

In order to analyze binding activity of the anti-hIGF antibody KM1468 to an antigen hIGF-I or hIGF-II, binding strengths of the anti-hIGF antibody KM1468, a commercially available anti-hIGF-I antibody sm1.2 and a commercially available anti-hIGF-II antibody S1F2 to hIGF-I and hIGF-II were measured in the following manner using the biosensor Biacore 2000 (manufactured by BIACORE) use of a surface plasmon resonance. HBS-EP (10 mM HEPES, 150 mM NaCl, 3 mM EDTA, 0.005% Tween 20, pH 7.4) (manufactured by BIACORE) was used for the dilution of analytes and as the reaction buffer.

Using an amine coupling (manufactured by BIACORE) in a sensor tip CM-5 (manufactured by BIACORE), hIGF-I was immobilized in 36.0 pg/mm$^2$, or hIGF-II was immobilized in 41.7 pg/mm$^2$, three antibodies diluted 6 steps by 2-fold dilution starting from 20 μg/ml were added thereto as the analytes at a flow rate of 20 μl/minute for 2 minutes, and then dissociation of the analytes was observed for 5 minutes. The reaction was carried out at 25° C. Association rate constant Kass and dissociation constant Kdiss were calculated from the binding reaction curves at respective concentrations, and the binding constant $K_A$ ($M^{-1}$) of each of these antibodies was calculated. The binding constant $K_A$ is calculated by $K_A$=Kass/Kdiss.

TABLE 1

|  | KM1468 | sm1.2 | S1F2 |
| --- | --- | --- | --- |
| $K_A$ (hIGF-I) | $7.86 \times 10^9$ | $1.86 \times 10^8$ | $4.62 \times 10^8$ |
| $K_A$ (hIGF-II) | $8.63 \times 10^9$ | $7.35 \times 10^7$ | $2.40 \times 10^9$ |

The results are shown in Table 1. The $K_A$ value of the anti-hIGF antibody KM1468 to hIGF-I was $7.86 \times 10^9$ $M^{-1}$, and its $K_A$ value to hIGF-II was $8.63 \times 10^9$ $M^{-1}$. Since the $K_A$ ratio of KM1468 to hIGF-I and hIGF-II was almost 1:1, it was shown that KM1468 can bind strongly to both of hIGF-I and hIGF-II with an almost equivalent strength. On the other hand, the $K_A$ value of the commercially available anti-hIGF-I monoclonal antibody sm1.2 to hIGF-I was $1.86 \times 10^8$ $M^{-1}$, and its $K_A$ value to hIGF-II was $7.35 \times 10^7$ $M^{-1}$. The $K_A$ values of the anti-hIGF antibody KM1468 to hIGF-I and hIGF-II were about 42 times higher to hIGF-I and about 120 times higher to hIGF-II, in comparison with the $K_A$ value of the commercially available anti-hIGF-I antibody sm1.2. Also, the $K_A$ value of the commercially available anti-hIGF-II antibody S1F2 to hIGF-I was $4.62 \times 10^8$ $M^{-1}$, and its $K_A$ value to hIGF-II was $2.4 \times 10^9$ $M^{-1}$. The $K_A$ values of the anti-hIGF antibody KM1468 to hIGF-I and hIGF-II were about 18 times higher to hIGF-I and about 3.6 times higher to hIGF-II, in comparison with the $K_A$ value of the commercially available anti-hIGF-II antibody S1F2. That is, it was shown that the anti-hIGF antibody KM1468 has a strong binding activity to each of hIGF-I and hIGF-II, in comparison with the commercially available anti-hIGF-I antibody sm1.2 and the commercially available anti-hIGF-II antibody S1F2.

(2) Influence of Anti-hIGF Antibody upon hIGF-dependent Growth

Each of a human breast cancer cell line MCF7 (ATCC HTB-22), a human colon cancer cell line HT-29 (ATCC HTB-38) or a human osteosarcoma cell line MG-63 (ATCC CRL-1427) was prepared into a TF/BSA medium [a medium prepared by adding 10 μg/ml of human transferrin (manufactured by Gibco BRL) and 200 μg/ml of BSA to D-MEM/F-12 (manufactured by Gibco BRL)] at a density of 0.5 to $1\times10^5$ cells/ml and dispensed in 100 μl/well portions into a 96 well culture plate. Subsequently, each of the factors hIGF-I (manufactured by Pepro Tech), hIGF-II (manufactured by Pepro Tech) and human insulin (manufactured Wako Pure Chemical Industries) diluted to each concentration with the TF/BSA medium was added in 50 μl/well portions thereto, and each of the antibodies diluted to each concentration with the TF/BSA medium in 50 μl/well portions, and cultured at 37° C. for 5 days in a 5% $CO_2$ incubator. After the culturing, a cell proliferation reagent WST-1 (manufactured by Roche) was dispensed in 20 μl/well portions, the cells were further cultured at 37° C. for 2.5 to 4 hours in a 5% $CO_2$ incubator, and then the absorbance at OD450 nm (hereinafter referred to as OD450) was measured using a plate reader Emax (manufactured by Molecular Devices).

Growth curves of the human breast cancer cell line MCF7 by respective factors are shown in FIG. 5A. In addition, growths in the presence of respective antibodies are shown in FIG. 5B in the presence of 40 ng/ml of hIGF-I, in FIG. 5C in the presence of 100 ng/ml of hIGF-II and in FIG. 5D in the presence of 100 ng/ml of human insulin. As shown in FIG. 5, the anti-hIGF antibody KM1468 strongly inhibited the cell growth by hIGF-I and hIGF-II, and the growth inhibitory activity was higher than the commercially available anti-hIGF-I antibody sm1.2 and the commercially available anti-hIGF-II antibody S1F2. On the other hand, each of the antibodies did not exert influence upon the growth by human insulin. The above results correlated well with the binding specificities of respective antibodies observed by the competitive ELISA of Example 3(1) and (2), and distinctly showed that the functions of hIGF-I and hIGF-II are inhibited by the binding of each antibody.

Growth curves of the human colon cancer cell line HT-29 by respective factors are shown in FIG. 6A. In addition, growths in the presence of respective antibodies are shown in FIG. 6B in the presence of 10 ng/ml of hIGF-I, in FIG. 6C in the presence of 10 ng/ml of hIGF-II and in FIG. 6D in the presence of 20 ng/ml of human insulin.

As shown in FIG. 6, the anti-hIGF antibody KM1468 strongly inhibited the cell growth by hIGF-I and hIGF-II to almost the same degree, and the growth inhibitory activity was higher than the commercially available anti-hIGF-I antibody sm1.2 and the commercially available anti-hIGF-II antibody S1F2. On the other hand, each of the antibodies did not exert influence upon the growth by human insulin. The above results correlated well with the binding specificities of respective antibodies observed by the competitive ELISA of Example 3(1) and (2), and distinctly showed that the functions of hIGF-I and hIGF-II are inhibited by the binding of each antibody. In addition, when KM1468 was added to the culturing of HT-29 cell in the presence of the addition of hIGF-I shown in FIG. 6B, and when KM1468 or S1F2 was added to the culturing of HT-29 cell in the presence of hIGF-II shown in FIG. 6C, growth of the cells was inhibited in comparison with the cell growth in the absence of respective antibodies and respective growth factors shown by dotted lines. That is, the HT-29 cell grows by producing hIGF-I or hIGF-II by itself, and the anti-hIGF antibody can inhibit an effect to proliferate cells by a growth factor produced by a cell itself.

Growth curves of the human osteosarcoma cell strain MG-63 by respective factors are shown in FIG. 7A. In addition, growths in the presence of the addition of respective antibodies are shown in FIG. 7B in the presence of 20 ng/ml of hIGF-I, in FIG. 7C in the presence of 20 ng/ml of hIGF-II and in FIG. 7D in the presence of 20 ng/ml of human insulin. As shown in FIG. 7, the anti-hIGF antibody KM1468 strongly inhibited the cell growth by hIGF-I and hIGF-II to almost the same degree, and the growth inhibitory activity was higher than the commercially available anti-hIGF-I antibody sm1.2 and the commercially available anti-hIGF-II antibody S1F2. On the other hand, each of the antibodies did not exert influence upon the growth by human insulin. The above results correlated well with the binding specificities of respective antibodies observed by the competitive ELISA of Example 3(1) and (2), and distinctly showed that the functions of hIGF-I and hIGF-II are inhibited by the binding of each antibody.

The hIGF-I- or hIGF-II-dependent cell growth inhibitory activity in the case of the above three types of cells was observed in any one of the anti-hIGF antibody KM1468, the commercially available anti-hIGF-I antibody sm1.2 and the commercially available anti-hIGF-II antibody S1F2. In the case of the hIGF-1-dependent growth activity, this cell growth inhibitory activity was highest in the anti-hIGF antibody KM1468, followed by the anti-hIGF-I antibody sm1.2 and the anti-hIGF-II antibody S1F2. Also, in the case of the hIGF-II-dependent growth activity, this cell growth inhibitory activity was highest in the anti-hIGF antibody KM1468, followed by the anti-hIGF-II antibody S1F2 and the anti-hIGF-I antibody sm1.2. This result coincides well with the result of binding strengths obtained using the surface plasmon resonance in Example 3(1), and distinctly showed that the anti-hIGF antibody KM1468 is superior to the commercially available antibodies of its binding activity to both of hIGF-I and hIGF-II and its hIGF-1-dependent or hIGF-II-dependent cell growth inhibitory effect.

Example 4

Influence of Anti-hIGF Antibody KM1468 upon Growth of hIGF-I Expressing Cell (1) Construction of hIGF-I Expressing Cell A transformant in which hIGF-I gene was transferred into a human lung cancer cell line A549 (ATCC CCL-185) was prepared in the following manner.

(1-1) Cloning of hIGF-I Gene and Preparation of Expression Vector

A 45.6 μg portion of total RNA was prepared from $1\times10^7$ cells of a human lung cancer cell strain PC-9 (*British Journal of Cancer,* 39, 15, 1976) using an RNA preparation kit RNeasy (manufactured by QIAGEN) in accordance with the instructions attached thereto. Using a 5 μg portion of the prepared total RNA, cDNA was synthesized using Superscript II (manufactured by GIBCO-BRL) in accordance with the instructions attached thereto.

Using the synthesized cDNA as the template, the hIGF-I gene was cloned by PCR. As primers for hIGF-I gene amplification, synthetic DNAs respectively having the nucleotide sequences shown in SEQ ID NOS: 27 and 28 were designed. Each synthetic DNAs contains a restriction enzyme recognizing sequence in its 5'-terminal for cloning it into plasmids pBluescript II SK(−) (manufactured by Stratagene) and pKANTEX93 (WO 97/10354). Specifically, 20 ng of the cDNA synthesized from the human lung cancer cell line PC-9, obtained in the above, was added to a buffer solution containing 50 μl of KOD(+) DNA Polymerase-attached KOD (+) Buffer #1 (manufactured by TOYOBO), 0.2 mM dNTPs, 2 mM magnesium chloride and 1 μM of the synthetic DNA respectively having the nucleotide sequences shown in SEQ ID NOS: 27 and 28, and using a DNA thermal cycler Gene-Amp PCR System 9600 (manufactured by PERKIN ELMER), the mixture was heated at 94° C. for 1 minute, and then, by adding 2.5 units of KOD DNA Polymerase (manufactured by TOYOBO), a cycle of 30 seconds at 94° C., 30 seconds at 62° C. and 30 seconds at 72° C. was repeated 30 cycles. A 50 µl portion of each reaction solution was digested with restriction enzymes EcoRI (manufactured by Takara Shuzo) and SalI (manufactured by Takara Shuzo) and then subjected to an agarose gel electrophoresis, and a PCR product of a gene coding for hIGF-I of about 0.5 kb was recovered using QIAquick Gel Extraction Kit (manufactured By QIAGEN).

Next, 0.1 µg of DNA obtained by digesting the plasmid pBluescript II SK(-) (manufactured by Stratagene) with the restriction enzymes EcoRI and SalI and then dephosphorylating the termini with Calf Intestine Alkaline Phosphatase (manufactured By Takara Shuzo, hereinafter referred to as CIAP) and 0.1 µg of each PCR product obtained in the above were prepared into 7.5 µl by adding sterile water and then allowed to react at 16° C. overnight by adding 7.5 µl of Ligation High (manufactured by TOYOBO). Using the recombinant plasmid DNA solution obtained in this manner, an *Escherichia coli* DH5α strain (manufactured by TOYOBO) was transformed. Each plasmid DNA was prepared from the transformant, which subjected to the reaction using BigDye Terminator Cycle Sequencing FS Ready Reaction Kit (manufactured by Applied Biosystems) in accordance with the instructions attached thereto, and its nucleotide sequence was determined using a nucleotide sequence automatic analyzer ABI PRISM 377 (manufactured by Applied Biosystems). As a result, the plasmid of interest pBS(II)SK(-)/hIGF-I having a gene sequence coding for hIGF-I shown in FIG. 8 was obtained.

Next, the restriction enzyme fragment (EcoRI-KpnI) of the pBS(II) SK(-)/hIGF-I obtained in the above coding for hIGF-I ligated with the EcoRI-KpnI fragment of pKANTEX93, and a plasmid pKANTEX93/hIGF-I shown in FIG. 8 was constructed. Nucleotide sequence of the plasmid pKANTEX93/hIGF-I was determined in the same manner as described above using the nucleotide sequence automatic analyzer ABI PRISM 377. As a result, the plasmid of interest pKANTEX93/hIGF-I containing a gene coding for hIGF-I was obtained.

(1-2) Preparation of hIGF-I Transformant

An hIGF-I expressing cell was prepared in the following manner by introducing the plasmid pKANTEX93/hIGF-I obtained in Example 1(1-1) into an animal cell.

The plasmid pKANTEX93/hIGF-I was digested with a restriction enzyme AatII (manufactured by TOYOBO) to linearize, and an 8 µg portion thereof was introduced into 4×10$^6$ cells of the human lung cancer cell line A 549 (ATCC CCL-185) by the electroporation method (*Cytotechnology*, 3, 133-140, 1990), and then the cells were suspended in 15 ml of RPMI medium [RPMI 1640 medium (manufactured by Invitrogen) containing 10% FCS and 50 µg/ml gentamicin (manufactured by Nakalai Tesque)] and transferred into a T75 flask (manufactured by Sumilon). After 24 hours of culturing at 37° C. in a 5% CO$_2$ incubator, G418 was added thereto to a concentration of 0.2 mg/ml and further cultured for 1 to 2 weeks. An A549/hIGF-I transformant having G418 resistance (hereinafter referred to as A549/hIGF-I) was obtained.

(1-3) Determination of hIGF-I Produced in a Culture Supernatant of A549/hIGF-I Cell The following test was carried out in order to verify whether the introduced hIGF-I gene is expressed in the A549/hIGF-I cell prepared in Example 3(1-1) and said cell is producing hIGF-I.

The A549/hIGF-I cell or A549 cell was cultured in the RPMI medium, and then the culture supernatant was recovered to measure the amount of hIGF-I contained in the culture supernatant by ELISA method as follows.

The methylated BSA-hIGF-I-immobilized plate shown in Example 1(4) was prepared, an hIGF-I solution prepared by 5-fold serial dilution starting from 2 µg/ml as the positive sample, or a culture supernatant of A549/hIGF-I or A549 cell, was dispensed in 25 µl/well portions, and then purified antibody of the anti-hIGF antibody KM1468 diluted to 0.6 µg/ml was dispensed, mixed and allowed to react at room temperature for 2 hours. After the reaction and subsequent washing with Tween-PBS, 1,000 times-diluted peroxidase-labeled rabbit anti-rat Ig antibody (manufactured by DAKO) was dispensed in 50 µl/well portions and allowed to react at room temperature for 1 hour. After the reaction and subsequent washing with Tween-PBS, 1,000 times-diluted anti-rat IgG-HRP (manufactured by DAKO) was dispensed in 50 µl/well portions and allowed to react at room temperature for 1 hour. After the reaction and subsequent 5 times of washing with Tween-PBS, an ABTS substrate solution [a solution prepared by dissolving 0.55 g of 2,2'-azinobis(3-ethylbenzothiazoline-6-sulfonic acid) ammonium salt in 1 liter of 0.1 M citrate buffer (pH 4.2), and further adding thereto 1 µl/ml of hydrogen peroxide just before use] was added in 50 µl/well portions to effect color development, and then OD415 was measured using the plate reader Emax.

The results are shown in FIG. 9. As shown in FIG. 9A, in comparison with the culture supernatant of A549 cell to which with the hIGF-I gene was not introduced, the binding activity was distinctively reduced in the culture supernatant of A549/hIGF-I cell to which the hIGF-I gene was introduced, thus showing that the A549/hIGF-I cell expresses hIGF-I.

(1-4) Influence of Anti-hIGF Antibody KM1468 upon Growth of hIGF-I Expressing Cell Whether the KM1468 can inhibit a cell growth dependent on hIGF-I produced by the cell itself (hereinafter referred to as autocrine cell growth) was examined using the hIGF-I gene-introduced cell A549/hIGF-I cell prepared in Example 3(1-1).

The A549/hIGF-I cell or A549 cell was cultured using RPMI 1640 medium (manufactured by Invitrogen) containing 10% FCS and 50 µg/ml gentamicin (manufactured by Nakalai Tesque) (hereinafter referred to as RPMI medium), and then respectively suspended in DMEM/F12 medium (-FCS, -Phenol red) (manufactured by Invitrogen) containing 10 µg/ml human transferrin (manufactured by GIBCO) and 200 µg/ml BSA (manufactured by Invitrogen) (to be referred to as serum-free medium hereinafter) to a cell density of 2×10$^5$ cells/ml.

Cell suspension of the A549/hIGF-I cell or A549 cell was dispensed in 100 µl/well portions into a 96 well plate (manufactured by Sumilon), the anti-hIGF antibody KM1468 serially diluted with the serum-free medium by 5-fold dilution starting from 200 µg/ml was added in 100 µl/well portions to each well, and then the cells were cultured at 37° C. for 5 days in a 5% CO$_2$ incubator. After the culturing, a cell proliferation reagent WST-1 (manufactured by Roche) was dispensed in 200 µl/well portions, the cells were further cultured at 37° C. for 4 hours in the 5% CO$_2$ incubator, and then the absorbance at OD450 nm (hereinafter referred to as OD450) was measured using a plate reader Emax (manufactured by Molecular Devices).

The results are shown in FIG. 10. The abscissa shows concentration of the anti-hIGF antibody KM1468 in each well at the time of the culturing. Growth of the A549/hIGF-I cell in the absence of the anti-hIGF antibody KM1468 shown by broken line was evidently increased in comparison with the growth of A549 cell shown by solid line which does not produce hIGF-I. This shows an autocrine growth in which the A549/hIGF-I cell prompts growth of the A549/hIGF-I cell itself by the self-produced hIGF-I. Such an autocrine growth shown in FIG. 10 was dose-dependently inhibited when the antibody KM1468 was added at the time of the culturing of A549/hIGF-I cell. On the other hand, the antibody KM1468 did not exert influence upon the growth of A549 cell. That is, it was shown that the anti-hIGF antibody KM1468 can inhibit the autocrine cell growth by the hIGF-I produced by the cell itself.

(1-5) Influence of Anti-hIGF Antibody KM1468 upon Anchorage Independent Growth of hIGF-I Expressing Cell Cells after malignant alteration have the ability to perform anchorage independent growth in which they can grow regardless of a suspended condition with no cell engraftment, such as in a soft agar. The ability to perform anchorage independent growth is very closely related to the tumorigenicity of cells, and it is considered that hIGF-I is concerned therein. Whether the KM1468 can inhibit anchorage independent growth of a cell was examined in the following manner using the A549/hIGF-I cell prepared in Example 3(1-1).

RPMI medium containing warmed 0.3% agar noble (manufactured by Difco) (hereinafter referred to as agar-RPMI medium) was dispensed in 1 ml/well portions into a 12 well plate (manufactured by Costar), and allowing the medium to stand at room temperature for scores of minutes to effect gelation. After culturing the A549/hIGF-I cell or A549 cell using the RPMI medium, the resulting cells were suspended in warmed agar-RPMI medium to a cell density of $1 \times 10^3$ cells/ml.

The cell suspension of A549/hIGF-I cell or A549 cell was overlaid on each well in an amount of 1 ml/well. After allowing to stand at room temperature for several minutes to effect gelation, the cells were cultured at 37° C. for 4 weeks in a 5% $CO_2$ incubator. After the culturing, the number of colonies formed in each well was counted under a microscope.

The results are shown in FIG. 11. As shown in FIG. 11, the anchorage independent cell growth of the A549/hIGF-I cell producing hIGF-1 was increased in comparison with the anchorage independent cell growth of the A549 cell. In addition, when 10 μg/ml of the anti-hIGF antibody KM1468 was added during culturing of A549/hIGF-I cell in the soft agar, the anchorage independent cell growth was completely inhibited by the addition of KM1468. That is, it was shown that hIGF-I is concerned in the anchorage independent cell growth, and the hIGF-dependent anchorage independent cell growth is inhibited by the anti-hIGF antibody KM1468.

(1-6) Tumor Growth Inhibitory Effect of Anti-hIGF Antibody KM1468 upon hIGF-I Expressing Cell Using the A549/hIGF-I cell prepared in Example 3(1-1), tumor growth inhibitory effect of the anti-hIGF antibody KM1468 was examined in the in vivo tumor formation in which hIGF-I takes a role according to the following manner.

The A549/hIGF-I cell or A549 cell was cultured using the RPMI medium and then respectively suspended in PBS to a cell density of $1 \times 10^6$ cells/ml.

A 100 μl portion of the cell suspension of A549/hIGF-I cell or A549 cell was subcutaneously transplanted into the right thoracic region of each nude mouse Balb/c Ajc-1 nu (female) of 6-weeks-old. The number of transplanted cells per one mouse becomes $1 \times 10^7$ cells. Starting just after the transplantation, 500 μg per one mouse of the anti-hIGF antibody KM1468 was administered through the tail vein twice a week, 8 times in total. As a negative control, PBS was simultaneously administered to on the same subcutaneous tumor transplantation mouse. Five days after the cell transplantation, tumor volume was measured. The tumor volume ($mm^3$) was calculated from the length, breadth and height of the tumor using a formula of length×breadth×height×0.5236.

The results are shown in FIG. 12. When growth of the subcutaneous tumor in the mouse transplanted with the A549 cell which does not produce hIGF-I was compared with that of the mouse transplanted with the A549/hIGF-I cell which produces hIGF-I, growth of the tumor was increased in the case of the subcutaneous tumor in the mouse transplanted with the A549/hIGF-I cell. In addition, in the mouse transplanted with the A549/hIGF-I cell, growth of the subcutaneous tumor was significantly inhibited when the anti-hIGF antibody KM1468 was administered. This result distinctively shows that the anti-hIGF antibody KM1468 inhibits growth of tumor also in vivo due to inhibition of hIGF-I.

Example 5

Preparation of Anti-hIGF-I Chimeric Antibody (1) Isolation and Analysis of cDNA Coding for the V Region of Anti-hIGF Antibody KM1468

(1-1) Preparation of mRNA from Anti-hIGF Antibody KM1468 Producing Hybridoma

A 27 μg portion of KM1468-derived mRNA was prepared from $5 \times 10^7$ cells of an anti-hIGF antibody KM1468 producing hybridoma KM1468 (FERM BP 7978) using an mRNA preparation kit Fast Track mRNA Isolation Kit (manufactured by Invitrogen) in accordance with the instructions attached thereto.

(1-2) Preparation of H Chain and L Chain cDNA Libraries of Anti-hIGF Antibody KM1468

A cDNA having an EcoRI-NotI adapter sequence on both termini was synthesized from 5 μg of the KM1468 mRNA prepared in Example 5(1-1) using TimeSaver cDNA Synthesis Kit (manufactured by Amersham Pharmacia) in accordance with the instructions attached thereto. Total amount of the synthesized cDNA was dissolved in 20 μl of sterile water and then fractionated by an agarose gel electrophoresis, and a cDNA fragment of about 1.5 kb corresponding to the H chain of an IgG class antibody and cDNA fragment of about 1.0 kb corresponding to the L chain of a κ class were recovered in an amount of about 1.0 μl respectively using QIAquick Gel Extraction Kit (manufactured by QIAGEN). Next, using λZAPII Predigested EcoRI/CIAP-Treated Vector Kit (manufactured by Stratagene), each of 0.1 μg of the cDNA fragment of about 1.5 kb and 0.1 μg of the cDNA fragment of about 1.0 kb was ligated to 1 μg of λZAPII vector whose termini had been dephosphorylated with Calf Intestine Alkaline Phosphatase after digestion with a restriction enzyme EcoRI attached to the kit, in accordance with the instructions attached thereto. After the ligation, a 2.5 μl of each reaction solution was packaged into λ phage using Gigapack III Gold Packaging Extracts (manufactured by Stratagene) in accordance with the instructions attached thereto to thereby obtaining $5.0 \times 10^4$ phage clones as an H chain cDNA library of KM1468, and $4.0 \times 10^4$ phage clones as an L chain cDNA library. Next, each phage was immobilized on a nylon membrane filter Hybond-$N^+$ (manufactured by Amersham Pharmacia) in accordance with a conventional method (Molecular Cloning: A Laboratory Manual, Cold Spring Harbor Lab. Press New York, 1989).

(1-3) Cloning of H Chain and L Chain cDNA of Anti-hIGF Antibody KM1468

The nylon membrane filters of H chain cDNA library and L chain cDNA library of KM1468 prepared in Example 5 (1-2) were detected using a cDNA of the C region of a mouse antibody [H chain is a fragment of mouse Cγ2b cDNA (*Nature*, 283, 786-789, 1980), and L chain is a fragment of mouse Cκ cDNA (*Cell*, 22, 197-207, 1980)] as the probe using ECL Direct Nucleic Acid Labeling and Detection Systems (manufactured by Amersham Pharmacia) in accordance with the instructions attached thereto, and each 10 phage clones strongly hybridized to the probe were obtained for each of the H chain and L chain. Next, each phage clone was converted into plasmid by the in vivo excision method in accordance with the instructions of λZAPII Predigested EcoRI/CIAP-Treated Vector Kit (manufactured by Stratagene). Nucleotide sequence of cDNA contained in the obtained plasmid was determined by carrying out the reaction using BigDye Terminator Cycle Sequencing FS Ready Reaction Kit (manufactured by Applied Biosystems) in accordance with the instructions attached thereto, and using a nucleotide sequence automatic analyzer ABI PRISM 377 (manufactured by Applied Biosystems). As a result, a plasmid pKM1468H5-2 containing the full length of functional H chain cDNA and a plasmid pKM1468L5-1 containing the full length of functional L chain cDNA, in which an ATG sequence considered to be the initiation codon is present in the 5'-terminus of respective cDNA, were obtained.

(1-4) Analysis of V Region Amino Acid Sequences of Anti-hIGF Antibody KM1468

The full length nucleotide sequence of VH of KM1468 contained in the plasmid pKM1468H5-2 is shown in SEQ ID NO: 1 and full length amino acid sequence of VH of KM1468 deduced therefrom is shown in SEQ ID NO: 2, and full length nucleotide sequence of VL of KM1468 contained in the plasmid pKM1468L5-1 is shown in SEQ ID NO: 3 and full length amino acid sequence of VL of KM1468 deduced therefrom is shown in SEQ ID NO: 4, respectively. In this connection, there are a large number of nucleotide sequences respectively corresponding to the amino acid sequences shown by SEQ ID NOS: 2 and 4, other than those shown by SEQ ID NOS: 1 and 3, and all of them are included in the scope of the present invention. Based on the comparison with known sequence data of antibodies (Sequences of Proteins of Immunological Interest, US Dept. Health and Human Services, 1991) and or the comparison with results of the analysis of N-terminal amino acid sequences of VH and VL of the purified anti-hIGF antibody KM1468 using a protein sequencer PPSQ-10 (manufactured by Shimadzu), it was revealed that the isolated respective cDNA is a secretion signal sequence-containing full length cDNA coding for the H chain or L chain of the anti-hIGF antibody KM1468, and a sequence of from the -19th to -1st positions of the amino acid sequence shown by SEQ ID NO: 2 is the secretion signal sequence of VH, and a sequence of from the -22nd to -1st positions of the amino acid sequence shown by SEQ ID NO: 4 is the secration signal sequense of VL.

Next, novelty of the VH and VL amino acid sequences of the anti-hIGF antibody KM1468 was examined. Using GCG Package (version 10.0, manufactured by Genetics Computer Group) as a sequence analyzing system, the existing protein amino acid sequence data bases [SWISS-PROT (Release 39.0), PIR-Protein (Release 65.0)] were searched by the BLAST method (*Journal of Molecular Biology*, 215,403-410, 1990). As a result, completely coincided sequences were not found for both VH and VL, and it was confirmed that the VH and VL of the anti-hIGF antibody KM1468 are novel amino acid sequences.

In addition, CDRs of the VH and VL of the anti-hIGF antibody KM1468 were identified by comparing with amino acid sequences of known antibodies. Amino acid sequences of CDR1, 2 and 3 of the VH of KM1468 are shown in SEQ ID NOS: 5, 6 and 7, and amino acid sequences of CDR1, 2 and 3 of the VL in SEQ ID NOS: 8, 9 and 10, respectively.

(2) Construction of Human Chimeric Antibody Expression Vector

An anti-hIGF-I chimeric antibody expression vector derived from the anti-hIGF antibody KM1468 was constructed in the following manner using the vector for expression of humanized antibody pKANTEX93 described in WO 97/10354 which can express the human IgG1, κ class antibodies and the plasmids obtained in Example 5(1-3) containing cDNAs for the H chain and L chain of KM1468.

Firstly, in order to insert the cDNAs for the VH and VL of KM1468 into the expression vector pKANTEX93 such that the amino acid sequences are not changed, cDNAs for the VH and VL of KM1468 were reconstructed by PCR. As the primers, synthetic DNAs respectively having the nucleotide sequences of SEQ ID NOS: 11 and 12 were designed for the VH cDNA, and synthetic DNAs respectively having the nucleotide sequences of SEQ ID NOS: 13 and 14 were designed for the VL cDNA. Each of the synthetic DNAs contains a restriction enzyme recognizing sequence in the 5'-terminus for its cloning into pKANTEX93. Specifically, 20 ng of the plasmid pKM1468H5-2 obtained in Example 5(1-3) was added to a buffer solution containing 50 μl of KOD DNA Polymerase-attached PCR Buffer #1 (manufactured by TOYOBO), 0.2 mM dNTPs, 1 mM magnesium chloride and 0.5 μM of the synthetic DNAs having the nucleotide sequences shown in SEQ ID NOS: 11 and 12, and using a DNA thermal cycler GeneAmp PCR System 9600 (manufactured by PERKIN ELMER), the mixture was heated at 94° C. for 3 minutes, to which 2.5 units of KOD DNA Polymerase (manufactured by TOYOBO) was added, and a cycle of 15 seconds at 98° C., 2 seconds at 65° C. and 30 seconds at 74° C. was repeated 25 cycles. In the same manner, another PCR was carried out by the same method described in the above, by adding 20 ng of the plasmid pKM1468L5-1 obtained in Example 5(1-3) to a buffer solution containing 50 μl of KOD DNA Polymerase-attached PCR Buffer #1 (manufactured by TOYOBO), 0.2 mM dNTPs, 1 mM magnesium chloride and 0.5 μM of the synthetic DNA fragments having the nucleotide sequences shown in SEQ ID NOS: 13 and 14. A 10 μl portion of each reaction solution was subjected to an agarose gel electrophoresis, and then a PCR product of about 0.5 kb for VH or a PCR product of about 0.43 kb for VL was recovered using QIAquick Gel Extraction Kit (manufactured By QIAGEN).

Next, 0.1 μl of DNA obtained by digesting the plasmid pBluescript II SK(-) (manufactured by Stratagene) with the restriction enzyme SmaI (manufactured by Takara Shuzo) and then dephosphorylating the termini with Calf Intestine Alkaline Phosphatase (hereinafter referred to as CIAP hereinafter; manufactured by Takara Shuzo) and 0.1 μl of each PCR product obtained in the above were prepared into 7.5 μl by adding sterile water and then allowed to react at 22° C. overnight after adding 7.5 μl of the solution I of TaKaRa DNA Ligation Kit Ver. 2 (manufactured by Takara Shuzo) and 0.3 μl of the restriction enzyme SmaI (manufactured by Takara Shuzo). Using the recombinant plasmid DNA solution obtained in this manner, an *Escherichia coli* DH5α strain (manufactured by TOYOBO) was transformed. Each plasmid DNA was prepared from the transformant, its nucleotide sequence was determined by carrying out the reaction using BigDye Terminator Cycle Sequencing FS Ready Reaction Kit (manufactured by Applied Biosystems) in accordance with the instructions attached thereto and using a nucleotide sequence automatic analyzer ABI PRISM377 (manufactured by Applied Biosystems). In this manner, plasmids pKM1468VH and pKM1468VL having the nucleotide sequences of interest shown in FIG. 13 were obtained.

Next, a plasmid pKANTEX1468H shown in FIG. 14 was constructed by inserting the restriction enzyme fragment (NotI-ApaI) containing the VH cDNA of pKM1468VH obtained in the above into the NotI-ApaI site of the vector pKANTEX93 for expression of humanized antibody. Also, a plasmid pKANTEX1468Chi shown in FIG. 14 was constructed by inserting the restriction enzyme fragment (EcoRI-BsiWI) containing the VL cDNA of pKM1468VL obtained in the above into the EcoRI-BsiWI site of the plasmid pKANTEX1468H. Using the plasmid pKANTEX1468Chi, nucleotide sequences of the VH and VL cDNA molecules were determined by carrying out the reaction using BigDye Terminator Cycle Sequencing FS Ready Reaction Kit (manufactured by Applied Biosystems) in accordance with the instructions attached thereto and using the nucleotide sequence automatic analyzer ABI PRISM 377 (manufactured by Applied Biosystems), and it was confirmed as a result that plasmids cloned with the VH and VL cDNAs of interest were obtained.

(3) Stable Expression of Anti-hIGF Chimeric Antibody Using Animal Cell

Using the anti-hIGF chimeric antibody expression vector pKANTEX1468Chi obtained in Example 5(2-1), expression of the anti-hIGF chimeric antibody in an animal cell was carried out in the following manner.

The plasmid pKANTEX1468Chi was digested with a restriction enzyme AatII (manufactured by TOYOBO) to linearize, a 10 μl portion thereof was introduced into $4 \times 10^6$ cells of a rat myeloma cell line YB2/0 (ATCC CRL 1581) by the electroporation method (*Cytotechnology*, 3, 133-140, 1990), and then the cells were suspended in 40 ml of H-SFM (5) medium [H-SFM medium (manufactured by Gibco BRL) containing 5% FCS] and dispensed in 200 μl/well portions into a 96 well culture plate (manufactured by Sumitomo Bakelite). After 24 hours of culturing at 37° C. in a 5% $CO_2$ incubator, G418 was added thereto to a concentration of 0.5 mg/ml and further cultured for 1 to 2 weeks. Culture supernatants were recovered from the wells in which transformant colonies showing G418-resistance were formed and became confluent, and concentration of the anti-hIGF chimeric antibody in the supernatants was measured by the binding ELISA shown in Example 6(1).

Regarding each of the transformants in wells in which expression of the anti-hIGF chimeric antibody was found in the culture supernatants, in order to increase antigen expression using of a dhfr gene amplification system, each of the transformants was suspended to a density of 1 to $2 \times 10^5$ cells/ml in H-SFM(5) containing 0.5 mg/ml of G418 and 50 nM of methotrexate (hereinafter referred to as MTX, manufactured by SIGMA) which is an inhibitor of a dhfr gene product dihydrofolate reductase (to be referred to as DHFR hereinafter), and the suspension was dispensed in 1 ml portions into a 24 well culture plate (manufactured by Greiner). By culturing at 37° C. for 1 to 2 weeks in a 5% $CO_2$ incubator, transformants showing a resistance to 50 M MTX were induced. When the transformants became confluent in wells, concentration of the anti-hIGF chimeric antibody in the culture supernatants was measured by the binding ELISA shown in Example 6(1). The transformants in wells in which expression of the anti-hIGF chimeric antibody was found in the culture supernatants were then cultured in a medium containing 100 nM MTX by the same method described in the above, and the transformants obtained in the same manner were further cultured in a medium containing 200 nM to thereby finally obtain a transformant which can grow in the H-SFM (5) containing 0.5 mg/ml of G418 and 200 nM of MTX and can highly express the anti-hIGF chimeric antibody. By subjecting the transformant thus obtained to single cell cloning by limiting dilution method twice, a transformant having the highest expression of the anti-hIGF chimeric antibody was obtained. As the transformant producing the anti-hIGF chimeric antibody derived from KM1468, KM3002 can be cited. The transformant KM3002 was deposited on Apr. 2, 2002, as FERM BP-7996 in International Patent Organism Depositary, National Institute of Advanced Industrial Science and Technology (postal code 305-8566; Central 6, 1-1-1 Higashi, Tsukuba, Ibaraki, Japan).

(4) Purification of Anti-hIGF Chimeric Antibody from Culture Supernatant

The transformant KM3002 obtained in Example 5(3) which expresses the anti-hIGF chimeric antibody was suspended in the H-SFM containing 0.5 mg/ml of G418, 200 nM of MTX and 5% of Daigo's GF21 (manufactured by Wako Pure Chemical Industries) to a density of 1 to $2 \times 10^5$ cells/ml, and dispensed in 100 ml portions into 175 $cm^2$ flasks (manufactured by Greiner). The cells were cultured at 37° C. for 5 to 7 days in a 5% $CO_2$ incubator, and the culture supernatant was recovered when they became confluent. By purifying the anti-hIGF chimeric antibody KM3002 from about 1 liter of the culture supernatant using Prosep-A (manufactured by Bioprocessing) column in accordance with the instructions attached thereto, about 10.2 mg of purified protein was obtained. About 4 μg of the obtained anti-hIGF chimeric antibody KM3002 was subjected to an electrophoresis in accordance with a known method (*Nature*, 227, 680-685, 1970) to examine its molecular weight and purification degree. The results are shown in FIG. 15. From the purified anti-hIGF chimeric antibody KM3002, one band corresponding to a molecular weight of about 150 kilodaltons (hereinafter referred to as Kd) was observed under non-reducing condition, and two bands corresponding to about 50 Kd and about 25 Kd was obtained under reducing condition. These molecular weights coincided with the reports that the IgG class antibody has a molecular weight of about 150 Kd under non-reducing condition, and is degraded into the H chain having a molecular weight of about 50 Kd and the L chain having a molecular weight of about 25 Kd under reducing condition due to cutting of the intramolecular S—S bond (*Antibodies: A Laboratory Manual*, Cold Spring Harbor Laboratory, Chapter 14, 1988; *Monoclonal Antibodies: Principles and Practice*, Academic Press Limited, 1996), thus confirming that the anti-hIGF chimeric antibody KM3002 is expressed as an antibody molecule having proper structure. In addition, as a result of the analysis of N-terminal amino acid sequences of the H chain and L chain of the purified anti-hIGF chimeric antibody KM3002 using a protein sequencer PPSQ-10 (manufactured by Shimadzu), it was confirmed that they coincide with the N-terminal amino acid sequences of the H chain and L chain of the anti-hIGF antibody KM1468.

Example 6

Examination of Reactivity of Anti-hIGF Chimeric Antibody KM3002

(1) Reactivity of Anti-hIGF Chimeric Antibody KM3002 to hIGF

Reactivity of the anti-hIGF rat antibody KM1468 and the anti-hIGF chimeric antibody KM3002 purified in Example 5(2-3) with hIGF-I was examined by the ELISA shown in Example 1(4). In this case, however, concentration of the methylated BSA-hIGF-I immobilized on the ELISA plate was changed to 0.5 μg/ml, and 4,000 times-diluted peroxidase-labeled rabbit anti-rat Ig antibody (manufactured by DAKO) was used as the secondary antibody in the case of the rat antibody, and 1,000 times-diluted peroxidase-labeled mouse anti-human IgG1 antibody (manufactured by Southern Biotechnology) in the case of the chimeric antibody. As shown in FIG. 16, the anti-hIGF chimeric antibody KM3002 showed an antibody concentration-dependent binding activity to hIGF-I. In addition, it was suggested that its activity is equivalent to the anti-hIGF rat antibody KM1468, though it is difficult to compare directly because of the different secondary antibodies.

(2) Influence of Anti-hIGF Chimeric Antibody KM3002 upon hIGF-Dependent Cell Growth Influence of the anti-hIGF rat antibody KM1468, the anti-hIGF chimeric antibody KM3002 purified in Example 5(2-3), a commercially available anti-hIGF-I antibody sm1.2 (manufactured by Upstate Biotechnology) and a commercially available anti-hIGF-II antibody S1F2 (manufactured by Upstate Biotechnology) upon hIGF-dependent cell growth was examined by the same method of Example 3(4). A colon cancer cell line HT-29 (ATCC HTB-38) was used as the human cancer cell line.

Growth of cells with the addition of respective antibodies are shown in FIG. 17A in the presence of 2 ng/ml of hIGF-I, and in FIG. 17B in the presence of 10 ng/ml of hIGF-II. As shown in FIG. 17, similar to the case of KM1468, KM3002 strongly inhibited cell growth by hIGF-I and hIGF-II, and the activity was higher than those of the commercially available anti-hIGF-I antibody sm1.2 and commercially available anti-hIGF-II antibody S1F2. In addition, the anti-hIGF antibody KM1468 having the same variable region of the chimeric antibody KM3002 showed almost the same growth inhibitory activity. The above results show that the anti-hIGF chimeric antibody KM3002 derived from KM1468 maintains equivalent antigen binding activity and antigen binding specificity to those of the original rat antibody KM1468 after the chimerization.

Example 7

Preparation of Anti-hIGF CDR-Grafted Antibody (1) Construction of cDNAs Coding for VH and VL of Anti-hIGF CDR-Grafted Antibody (1-1) Design of Amino Acid Sequences of the VH and VL Amino Acid Sequences of Anti-hIGF CDR-Grafted Antibody Firstly, amino acid sequence of the VH of anti-hIGF CDR-grafted antibody was designed as follows. An FR amino acid sequence of the VH of a human antibody was selected for grafting the CDR amino acid sequence of the VH of the anti-hIGF antibody KM1468 identified in Example 5(1-4). When a human antibody FR having the highest homology with the VH FR of the anti-hIGF antibody KM1468 was searched from an official data base, CAM (*Proceedings of the National Academy of Sciences of United States of America*, 77, 3239-3243, 1980) showed the highest homology (81.6%). Accordingly, the VH of anti-hIGF CDR-grafted antibody was designed based on the FR of CAM. In the FR of CAM, there were four positions where the amino acid sequence is not univocally determined (13th position, 74th position, 77th position and 90th position), and amino acid residues which are not common in the human antibody sequences were recognized in the 3rd position and 40th position. In order to reduce immunogenicity, these amino acid residues were changed into amino acid residues which are found in human antibodies with a high frequency (Sequences of Proteins of Immunological Interest, US Dept. Health and Human Services, 1991). By grafting the VH CDR amino acid sequence of the anti-hIGF antibody KM1468 to an appropriate position of the designed CAM-derived FR amino acid sequence, the VH amino acid sequence HV.0 of the anti-hIGF CDR-grafted antibody described in SEQ ID NO: 15 was designed.

Next, amino acid sequence of the VL of anti-hIGF CDR-grafted antibody was designed as follows. An FR amino acid sequence of the VL of a human antibody was selected for grafting the CDR amino acid sequence of the VL of the anti-hIGF antibody KM1468 identified in Example 5(1-4). Cabat et al. have classified known various VL regions of human antibodies into 4 subgroups based on the homology of their amino acid sequences (HSG I to IV), and reported on consensus sequences for respective subgroups (Sequences of Proteins of Immunological Interest, US Dept. Health and Human Services, 1991). Since there is a possibility that these consensus sequences have low immunogenicity in human, it was decided to design the VL amino acid sequence of anti-hIGF CDR-grafted antibody based on these consensus sequences. In order to prepare an anti-hIGF CDR-grafted antibody having a higher activity, among the FR amino acid sequences of the consensus sequences of four VL subgroups of human antibodies, an FR amino acid sequence having the highest homology with the FR amino acid sequence of the VL of KM1468 was selected. Results of the homology search are shown in Table 2. As shown in Table 2, the FR amino acid sequence of the VL region of KM1468 showed the highest homology with the subgroup IV.

TABLE 2

| HSG I | HSG II | HSG III | HSG IV |
| --- | --- | --- | --- |
| 66.3% | 61.3% | 66.3% | 67.5% |

Based on the above results, the VL amino acid sequence LV.0 of the anti-hIGF CDR-grafted antibody shown in SEQ ID NO: 16 was designed by grafting the VL CDR amino acid sequence of the anti-hIGF antibody KM1468 to an appropriate position of the FR amino acid sequence of the consensus sequence of subgroup IV of the human antibody VL.

The VH amino acid sequence HV.0 and VL amino acid sequence LV.0 of the anti-hIGF CDR-grafted antibody are sequences in which only the CDR amino acid sequences of the anti-hIGF antibody KM1468 were grafted to the selected FR amino acid sequences of a human antibody. Generally, in the case of human CDR-grafted antibodies, their activities are reduced in many cases when CDR amino acid sequences of an antibody of a non-human animal is grafted alone. In order to avoid this problem, among FR amino acid residues different between a human antibody and an antibody of a non-human animal, certain amino acid residues considered to exert influence upon the activity are grafted together with the CDR amino acid sequences. Accordingly, an examination was carried out on the identification of the FR amino acid residues considered to exert influence upon the activity. Firstly, a three-dimensional structure of an antibody V region (HV0LV0) comprising the VH amino acid sequence HV.0 and VL amino acid sequence LV.0 of the anti-hIGF CDR-grafted antibody designed above was constructed using a computer modeling technique. Three-dimensional structure coordinate system was using a software AbM (manufactured by Oxford Molecular), and the three-dimensional structure was displayed using a software Pro-Explore (manufactured by Oxford Molecular) or RasMo1 (manufactured by Glaxo), in accordance with the respective instructions attached thereto. Also, a computer model of the three-dimensional structure of the V region of the anti-hIGF antibody KM1468 was constructed in the same manner. In addition, a three-dimensional structure model which comprises amino acid sequences in which amino acid residues in the FR amino acid sequences of VH and VL of HV0LV0, which are different from those in the anti-hIGF antibody KM1468, were changed in order into the residues positioned in the corresponding positions of the anti-hIGF antibody KM1468 was constructed in the same manner, and V region three-dimensional structures of the anti-hIGF antibody KM1468, HV0LV0 and modified HV0LV0 were compared. As a result, as the residues considered to be exerting influence upon the antibody activity by changing three-dimensional structure of the antigen binding region, among amino acid residues of the FR of HV0LV0, the 1st position Gln, the 77th position Asn, the 84th position Asn, the 93rd position Val, the 97th position Ala and the 98th position Arg were selected regarding the HV.0, and the 1st position Asp, the 9th position Asp, the 10th position Ser, the 11th position Leu, the 22nd position Asn, the 35th position Tyr, the 39th position Pro, the 42nd position Pro, the 45th position Leu, the 46th position Leu, the 69th position Asp, the 70th position Phe, the 71st position Thr, the 82nd position Val and the 84th position Val regarding the LV.0. Among these selected amino acid residues, at least one or more thereof were changed into the amino acid residues found in the rat antibody KM1468 to thereby design VH and VL of the human CDR-grafted antibody having various modifications.

(1-2) Construction of cDNA Coding for VH of Anti-hIGF CDR-Grafted Antibody

A cDNA coding for the VH amino acid sequence of the anti-hIGF CDR-grafted antibody HV.0 designed in Example 6(1-1) was constructed using PCR in the following manner.

Firstly, the designed amino acid sequence was connected to the secretion signal sequence of the H chain of the anti-hIGF antibody KM1468 shown in SEQ ID NO: 2 to make the full length antibody amino acid sequence. Next, said amino acid sequence was converted into gene codons. When two or more gene codons were present for one amino, acid residue, corresponding gene codon was determined by taking the codon usage found in nucleotide sequences of antibody genes into consideration (Sequences of Proteins of Immunological Interest, US Dept. Health and Human Services, 1991). By connecting the determined gene codons, nucleotide sequence of a cDNA coding for full length antibody V region amino acid sequence was designed, and nucleotide sequences for the binding of primers for amplification for PCR (include a restriction enzyme recognizing sequence for cloning into a vector for expression of humanized antibody) were added to the 5'-terminus and 3'-terminus. The nucleotide sequence thus designed was divided into a total of six fragments, each comprising about 100 bases, starting from the 5'-terminal side (in such a manner that adjoining nucleotide sequences have an overlapping sequence of about 20 bases on the termini), and synthetic oligonucleotides were synthesized based on them in an alternate order of sense chain and antisense chain (manufactured by GENSET).

Each oligonucleotides was added to 50 μl of the reaction solution to a final concentration of 0.1 μM, and PCR was carried out using 0.5 μM of M13 primer RV (manufactured by Takara Shuzo), 0.5 μM of M13 primer M4 (manufactured by Takara Shuzo) and 1 unit of KOD polymerase (manufactured by TOYOBO) in accordance with the instructions attached to the KOD polymerase. Regarding the reaction conditions in this case, the reaction was carried out in accordance with the conditions described in the instructions (30 cycles of a cycle comprising 94° C. for 30 seconds, 50° C. for 30 seconds and 74° C. for 60 seconds). The reaction solution was subjected to ethanol precipitation, the precipitate was dissolved in sterile water, which was subjected to an appropriate restriction enzyme treatment and then connected to a plasmid pBluescript II SK(−) (manufactured by Stratagene). Using the recombinant plasmid DNA solution obtained in this manner, an *Escherichia coli* DH5α strain was transformed and plasmid DNA samples were prepared from the resulting transformants. Their nucleotide sequences of the obtained plasmid DNA samples were analyzed using BigDye Terminator Cycle Sequencing FS Ready Reaction Kit (manufactured by Applied Biosystems), and it was confirmed that a plasmid having the nucleotide sequence of interest was obtained.

Next, the FR amino acid residues designed in Example 6(1-1) was modified by preparing a synthetic oligonucleotides having mutations and carrying out the aforementioned PCR, or by carrying out the PCR using a plasmid DNA containing a cDNA coding for the HV.0 prepared in the above as the template and a synthetic DNA having a mutation as a primer and isolating an amplified fragment. The modification was carried out in such a manner that gene codons of the amino acid residues after the modification became the gene codons found in the rat antibody KM1468.

(1-3) Construction of cDNA Coding for VL of Anti-hIGF CDR-Grafted Antibody

A cDNA coding for the VH amino acid sequence of the anti-hIGF CDR-grafted antibody LV.0 designed in Example 6(1-1) was constructed using PCR in the following manner.

Firstly, the designed amino acid sequence was connected to the secretion signal sequence of the L chain of the anti-hIGF antibody KM1468 shown in SEQ ID NO: 4 to make the full length antibody amino acid sequence. Next, said amino acid sequence was converted into gene codons. When two or more gene codons were present for one amino acid residue, corresponding gene codon was determined by taking the codon usage found in nucleotide sequences of antibody genes into consideration (Sequences of Proteins of Immunological Interest, US Dept. Health and Human Services, 1991). By connecting the determined gene codons, nucleotide sequence of a cDNA coding for full length antibody V region amino acid sequence was designed, and nucleotide sequences for the binding of primers for amplification for PCR (including a restriction enzyme recognizing sequence for cloning into a vector for humanized antibody expression use) were added to the 5'-terminus and 3'-terminus. The nucleotide sequence thus designed was divided into a total of six fragments, each comprising about 100 bases, starting from the 5'-terminal side (in such a manner that adjoining nucleotide sequences have an overlapping sequence of about 20 bases on the termini), and synthetic oligonucleotides were synthesized based on them in an alternate order of sense chain and antisense chain (manufactured by GENSET).

Each oligonucleotide was added to 50 μl of the reaction solution to a final concentration of 0.1 μM, and PCR was carried out using 0.5 µM of M13 primer RV (manufactured. by Takara Shuzo), 0.5 µM of M13 primer M4 (manufactured by Takara Shuzo) and 1 unit of KOD polymerase (manufactured by TOYOBO) in accordance with the instructions attached to the KOD polymerase. Regarding the reaction conditions, the reaction was carried out in accordance with the conditions described in the instructions (30 cycles of a cycle comprising 94° C. for 30 seconds, 50° C. for 30 seconds and 74° C. for 60 seconds). The reaction solution was subjected to ethanol precipitation, the precipitate was dissolved in sterile water, subjected to an appropriate restriction enzyme treatment and then connected to the plasmid pBluescript II SK(−) (manufactured by Stratagene). Using the recombinant plasmid DNA solution obtained in this manner, the *Escherichia coli* DH5α strain was transformed and plasmid DNA samples were prepared from the resulting transformants. The nucleotide sequences of the plasmid DNA samples were analyzed using BigDye Terminator Cycle Sequencing FS Ready Reaction Kit (manufactured by Applied Biosystems), and it was confirmed that a plasmid having the nucleotide sequence of interest was obtained.

Next, the FR amino acid residues designed in Example 6 (1-1) was modified by preparing a synthetic oligonucleotide having mutations and carrying out the aforementioned PCR, or by carrying out the PCR using a plasmid DNA containing a cDNA coding for the LV.0 prepared in the above as the template and a synthetic DNA having a mutation as a primer, and isolating an amplified fragment. The modification was carried out in such a manner that gene codons of the amino acid residues after the modification became the gene codons found in the anti-hIGF antibody KM1468.

(2) Construction of Anti-hIGF CDR-Grafted Antibody Expression Vectors

Various anti-hIGF CDR-grafted antibody expression vectors were constructed by inserting the HV.0 and LV.0-encoding cDNAs obtained in Example 6(1-2) and Example (1-3) and cDNAs coding for modified products thereof into an appropriate position of the vector pKANTEX93 for expression of humanized antibody described in WO 97/10354.

(3) Stable Expression of Anti-hIGF CDR-Grafted Antibody Using Animal Cell

Stable expression of anti-hIGF CDR-grafted antibody using an animal cell and purification of the antibody from a culture supernatant were carried out in accordance with the aforementioned method described in Example 5(3).

INDUSTRIAL APPLICABILITY

An object of the present invention is to provide an antibody which specifically binds to human IGF-I and human IGF-II to inhibit functions of human IGF-I and human IGF-II and has the binding activity with a binding constant of $5 \times 10^9$ $M^{-1}$ or more measured with a biosensor BIACORE. Another object of the invention is to provide a diagnostic drug, a preventive drug and a therapeutic drug for a human IGF-mediated disease or a disease wherein its morbid state progresses by abnormal acceleration of human IGF production, using said antibody.

The invention claimed is:

1. An antibody or an antibody fragment thereof, which (i) specifically binds to IGF-I and IGF-II to inhibit both human IGF-I and human IGF-II, and (ii) binds to both human IGF-I and human IGF-II with almost equivalent strength of affinity and with a binding constant of $5 \times 10^9 M^{-1}$ or more measured with a biosensor BIACORE™, the CDR1, CDR2 and CDR3 of the VH chain of said antibody or said antibody fragment thereof comprising SEQ ID NOS:5, 6 and 7 respectively, and/or CDR1, CDR2 and CDR3 of the VL chain of said antibody or said antibody fragment comprising SEQ ID NOS: 8, 9 and 10 respectively.

2. The antibody or the antibody fragment thereof according to claim 1, wherein the antibody is a non-human animal antibody or a recombinant antibody.

3. The antibody or the antibody fragment thereof according to claim 2, which is a recombinant antibody selected from the group consisting of a human chimeric antibody, a human CDR-grafted antibody.

4. An isolated antibody or an antibody fragment thereof, which (i) specifically binds to IGF-I and IGF-II to inhibit both human IGF-I and human IGF-II, and (ii) binds to both human IGF-I and human IGF-II with almost equivalent strength of affinity and with a binding constant of $5 \times 10^9 M^{-1}$ or more measured with a surface plasmon resonance biosensor, wherein the VH chain of the antibody or antibody fragment thereof comprises SEQ ID NO: 2 and/or the VL chain of the antibody or antibody fragment thereof comprises SEQ ID NO: 4.

5. The antibody or the antibody fragment thereof according to claim 4, wherein the antibody of a non-human animal is produced by hybridoma KM1468 (FERM BP-7978).

6. The antibody or the antibody fragment thereof according to claim 3, wherein the VH chain of the human chimeric antibody comprises SEQ ID NO: 2, and/or the VL chain of the human chimeric antibody comprises SEQ ID NO: 4.

7. The antibody or the antibody fragment thereof according to claim 6, wherein the human chimeric antibody comprises the VH chain and/or the VL chain of the antibody produced by KM1468 (FERM BP-7978).

8. The antibody or the antibody fragment thereof according to claim 3, wherein the human chimeric antibody comprises a constant region of a human antibody.

9. The antibody or the antibody fragment thereof according to claim 8, wherein the constant region of a human antibody comprises the constant region of an IgG1 class and/or K class human antibody.

10. The antibody or the antibody fragment thereof according to claim 9, wherein the human chimeric antibody is produced by transformant KM3002 (FERM BP-7996).

11. The antibody or the antibody fragment thereof according to claim 3, wherein the human CDR-grafted antibody comprises a constant region of a human antibody.

12. The antibody fragment according to claim 11, wherein the antibody fragment is selected from the group consisting of Fab, Fab', F(ab')$_2$, single chain antibody (scFv), dimerized V region (diabody), disulfide-stabilized V region (dsFv) and a CDR-containing peptide.

13. A method for producing isolated an antibody or the antibody fragment thereof according to claim 2, which comprises culturing a transformant obtained by introducing into a host cell a recombinant vector containing DNA encoding said antibody or antibody fragment thereof in a medium to produce and accumulate the antibody or the antibody fragment thereof, and recovering the antibody or the antibody fragment thereof from the culture.

* * * * *

UNITED STATES PATENT AND TRADEMARK OFFICE
CERTIFICATE OF CORRECTION

PATENT NO.         : 7,438,911 B2
APPLICATION NO.    : 10/513148
DATED              : October 21, 2008
INVENTOR(S)        : Kenya Shitara et al.

It is certified that error appears in the above-identified patent and that said Letters Patent is hereby corrected as shown below:

TITLE PAGE [56] REFERENCES CITED:

Other Publications, "Laubli et al., FEBS Letters. Nov. 1982; 149(1)109-112 (previously cited in the Office Action of Mar. 29, 2007).*" should be deleted.

TITLE PAGE [56] REFERENCES CITED:

Other Publications, "Laubli et al., FEBS Letters. Nov. 1982 149(1):109-112*" should read --Laubli et al., FEBS Letters, Vol. 149, No. 1 (1982) 109-12*--; and "Nissley et al., (C.H. Li. Ed) Hormonal Proteins & Peptides, vol. XII. NewYOrk: Academic. Press. 1984. pp. 127-203.*" should read --Nissley et al., Hormonal Proteins & Peptides, Vol. XII (C.H. Li, ed.), Acad. Press (1984) 127-203*--.

COLUMN 1:

Line 35, "three" should read --, two--.

COLUMN 4:

Line 24, "times-higher" should read --times higher--.

COLUMN 5:

Line 19, "receptor-or" should read --receptor or--; and
Line 61, "dose" should read --does--.

COLUMN 6:

Line 6, "2389-92." should read --2389-92).--; and
Line 14, "2961-70." should read --2961-70).--.

COLUMN 12:

Line 66, "existed" should read --existing--.

UNITED STATES PATENT AND TRADEMARK OFFICE
CERTIFICATE OF CORRECTION

PATENT NO. : 7,438,911 B2
APPLICATION NO. : 10/513148
DATED : October 21, 2008
INVENTOR(S) : Kenya Shitara et al.

It is certified that error appears in the above-identified patent and that said Letters Patent is hereby corrected as shown below:

COLUMN 13:

Line 4, "existed" should read --existing--.

COLUMN 17:

Line 40, "ant" should read --and--.

COLUMN 19:

Line 46, "exam-" should read --exem- --.

COLUMN 20:

Line 39, "Vivo" should read --vivo--.

COLUMN 21:

Line 57, "easiness for" should read --ease of--;
Line 58, "tion" should read --tion of--; and "easiness for" should read --ease of--; and
Line 59, "easiness of" should read --ease of--; and "introducion" should read --introduction--.

COLUMN 22:

Line 20, "animals" should read --the following animals are--.

COLUMN 23:

Line 36, "alarified" should read --clarified--; and
Line 40, "CDRs" should read --CDR--.

COLUMN 24:

Line 12, "suatable" should read --suitable--; and
Line 45, "prefarable" should read --preferable--.

UNITED STATES PATENT AND TRADEMARK OFFICE
CERTIFICATE OF CORRECTION

| | |
|---|---|
| PATENT NO. | : 7,438,911 B2 |
| APPLICATION NO. | : 10/513148 |
| DATED | : October 21, 2008 |
| INVENTOR(S) | : Kenya Shitara et al. |

It is certified that error appears in the above-identified patent and that said Letters Patent is hereby corrected as shown below:

COLUMN 25:

Line 27, "have" should read --has--; and "many" should read --much--;
    Line 32, "try" should read --trial--.

COLUMN 27:

Line 15, "Vivo" should read --vivo--;
    Line 19, "2." should read --2--; and
    Line 20-21, "techniques based." should read --based techniques.--.

COLUMN 28:

Line 20, "intergra-" should read --integra- --;
    Line 23, "examplified." should read --exemplified.--;
    Line 43, "intergration" should read --integration--; and
    Line 46, "examplified" should read --exemplified--.

COLUMN 29:

Line 6, "intergration" should read --integration--;
    Line 7, "manufactured." should read --manufactured--;
    Line 9, "examplified." should read --exemplified.--;
    Line 29, "DNA" should read --DNAs--;
    Line 30, "AS" should read --As--;
    Line 34, "examplified." should read --exemplified.--; and
    Line 53, "examplified." should read --exemplified.--.

COLUMN 32:

Line 40, "open square" should read --□--; and
    Line 66, "like" should read --line--.

COLUMN 35:

Line 2, "immobilized." should read --immobilization.--.

UNITED STATES PATENT AND TRADEMARK OFFICE
CERTIFICATE OF CORRECTION

| | |
|---|---|
| PATENT NO. | : 7,438,911 B2 |
| APPLICATION NO. | : 10/513148 |
| DATED | : October 21, 2008 |
| INVENTOR(S) | : Kenya Shitara et al. |

It is certified that error appears in the above-identified patent and that said Letters Patent is hereby corrected as shown below:

COLUMN 37:

Line 6, "or" should read --or in--.

COLUMN 41:

Line 13, "By" should read --by--.

COLUMN 44:

Line 7, "to on" should read --to--.

COLUMN 45:

Line 42, "are" should read --is--; and
Line 48, "and or" should read --and/or--.

COLUMN 48:

Line 49, "was" should read --were--.

COLUMN 50:

Line 61, "is" should read --are--.

COLUMN 52:

Line 28, "was" should read --were--.

COLUMN 65:

Line 57, "antibody or an antibody" should read --isolated antibody, or an isolated antibody--;
Line 62, "biosensor BIACORE™," should read --surface plasmon resonance biosensor, wherein--;
Line 63, "antibody" should read --isolated antibody or isolated antibody--;
Line 64, "comprising" should read --comprises--; and "respectively," should read --respectively--; and
Line 65, "and/or" should read --and--.

UNITED STATES PATENT AND TRADEMARK OFFICE
CERTIFICATE OF CORRECTION

PATENT NO.        : 7,438,911 B2
APPLICATION NO.   : 10/513148
DATED             : October 21, 2008
INVENTOR(S)       : Kenya Shitara et al.

It is certified that error appears in the above-identified patent and that said Letters Patent is hereby corrected as shown below:

<u>COLUMN 66</u>:

Line 61, "antibody," should read --antibody and--; and "isolated an" should read --an isolated--.

Signed and Sealed this

Seventeenth Day of March, 2009

JOHN DOLL
*Acting Director of the United States Patent and Trademark Office*